US009073206B2

(12) United States Patent
Carson et al.

(10) Patent No.: US 9,073,206 B2
(45) Date of Patent: Jul. 7, 2015

(54) METHODS AND APPARATUS FOR AUTOMATED FILLING OF PACKAGINGS WITH MEDICATIONS

(75) Inventors: Bradley E. Carson, Ottawa Hills, OH (US); Joseph T. DeDeo, Mount Laurel, NJ (US); Michael J. Szesko, Freehold, NJ (US); Thomas L. Stocker, Miamisburg, OH (US); Kurtis J. Hoffman, Wauseon, OH (US); Patrick D. Downing, Fayette, OH (US)

(73) Assignee: Omnicare, Inc., Cincinnati, OH (US)

( * ) Notice: Subject to any disclaimer, the term of this patent is extended or adjusted under 35 U.S.C. 154(b) by 489 days.

(21) Appl. No.: 13/529,554

(22) Filed: Jun. 21, 2012

(65) Prior Publication Data

US 2013/0340390 A1   Dec. 26, 2013

(51) Int. Cl.
| | |
|---|---|
| G06F 7/00 | (2006.01) |
| B25J 9/00 | (2006.01) |
| B25J 15/00 | (2006.01) |
| B65B 35/08 | (2006.01) |
| B65B 43/44 | (2006.01) |
| B65B 43/46 | (2006.01) |
| B65B 43/50 | (2006.01) |
| B65B 5/10 | (2006.01) |
| G06F 19/00 | (2011.01) |

(52) U.S. Cl.
CPC ............ *B25J 9/0096* (2013.01); *B25J 15/0052* (2013.01); *B65B 35/08* (2013.01); *B65B 43/44* (2013.01); *B65B 43/46* (2013.01); *B65B 43/50* (2013.01); *B65B 5/103* (2013.01); *G06F 19/3462* (2013.01); *B65B 2220/14* (2013.01); *B65B 2230/02* (2013.01)

(58) Field of Classification Search
None
See application file for complete search history.

(56) References Cited

U.S. PATENT DOCUMENTS

| | | | |
|---|---|---|---|
| 4,655,026 | A | 4/1987 | Wigoda |
| 4,733,362 | A | 3/1988 | Haraguchi |
| 5,081,816 | A | 1/1992 | Cardinali |
| 5,646,912 | A | 7/1997 | Cousin |
| 5,765,606 | A | 6/1998 | Takemasa et al. |
| 5,805,455 | A | 9/1998 | Lipps |
| 5,845,255 | A | 12/1998 | Mayaud |
| 6,006,946 | A | 12/1999 | Williams et al. |
| 6,036,812 | A | 3/2000 | Williams et al. |
| 6,119,737 | A | 9/2000 | Yuyama et al. |
| 6,317,648 | B1 | 11/2001 | Sleep et al. |
| 6,345,487 | B1 | 2/2002 | Luciano et al. |
| 6,370,841 | B1 | 4/2002 | Chudy et al. |
| 6,449,927 | B2 | 9/2002 | Hebron et al. |

(Continued)

OTHER PUBLICATIONS

The International Bureau of WIPO, International Preliminary Report on Patentability in International Application No. PCT/US2012/046227 dated Jan. 14, 2014 (9 pages).

(Continued)

*Primary Examiner* — Yolanda Cumbess

(74) *Attorney, Agent, or Firm* — Wood, Herron & Evans, LLP

(57) ABSTRACT

Methods for filling packagings with at least one medication includes receiving filling instructions for an order and operating an automated packaging station to fill a plurality of packagings making up an order. Operating the automated packaging station includes positioning a plurality of cassettes containing the medications needed for the order onto a feeder base at a single filling location, and moving each of the plurality of packagings to the filling location. The operation also includes actuating at least one of the cassettes at the feeder base simultaneously and according to the filling instructions when each packaging is located at the filling location. Automated packaging stations operable to perform the above filling instructions are also provided.

39 Claims, 56 Drawing Sheets

(56) References Cited

U.S. PATENT DOCUMENTS

| | | |
|---|---|---|
| 6,471,088 B1 | 10/2002 | Uema et al. |
| 6,481,180 B1 | 11/2002 | Takahashi et al. |
| 6,522,945 B2 | 2/2003 | Sleep et al. |
| 6,597,969 B2 | 7/2003 | Greenwald et al. |
| 6,609,047 B1 | 8/2003 | Lipps |
| 6,681,149 B2 | 1/2004 | William et al. |
| 6,690,998 B1 | 2/2004 | Yuyama |
| 6,717,598 B1 | 4/2004 | Melton, Jr. et al. |
| 6,749,085 B2 | 6/2004 | Garrant et al. |
| 6,760,643 B2 | 7/2004 | Lipps |
| 6,775,588 B1 | 8/2004 | Peck |
| 6,775,589 B2 | 8/2004 | William et al. |
| 6,983,579 B2 | 1/2006 | Rice et al. |
| 6,988,634 B2 | 1/2006 | Varis |
| 6,990,383 B2 | 1/2006 | Hoppes et al. |
| 6,993,402 B2 | 1/2006 | Klass et al. |
| 7,006,893 B2 | 2/2006 | Hart et al. |
| 7,016,752 B1 | 3/2006 | Ruben et al. |
| 7,016,766 B2 | 3/2006 | William et al. |
| 7,027,886 B2 | 4/2006 | Hoppes et al. |
| 7,072,840 B1 | 7/2006 | Mayaud |
| 7,182,105 B2 | 2/2007 | Feehan et al. |
| 7,185,476 B1 | 3/2007 | Siegel et al. |
| 7,203,571 B2 | 4/2007 | Kirsch et al. |
| 7,225,131 B1 | 5/2007 | Bangalore et al. |
| 7,225,597 B1 | 6/2007 | Knoth |
| 7,289,879 B2 | 10/2007 | William et al. |
| 7,317,525 B2 | 1/2008 | Rzasa et al. |
| RE40,453 E | 8/2008 | Lasher et al. |
| 7,426,814 B2 | 9/2008 | Knoth |
| 7,454,880 B1 | 11/2008 | Austin et al. |
| 7,471,993 B2 | 12/2008 | Rosenblum |
| 7,496,521 B1 | 2/2009 | Louie et al. |
| 7,555,875 B2 | 7/2009 | Kim |
| 7,574,844 B2 | 8/2009 | Kamineni |
| 7,610,115 B2 | 10/2009 | Rob et al. |
| 7,636,718 B1 | 12/2009 | Steen et al. |
| 7,637,079 B2 | 12/2009 | Klingel et al. |
| 7,668,618 B2 | 2/2010 | Szesko et al. |
| 7,680,554 B2 | 3/2010 | Erickson et al. |
| 7,689,318 B2 | 3/2010 | Draper |
| 7,690,173 B2 | 4/2010 | Luciano, Jr. et al. |
| 7,721,512 B2 | 5/2010 | Siegel et al. |
| 7,747,345 B2 | 6/2010 | Ohmura et al. |
| 7,774,210 B1 | 8/2010 | Sandberg |
| 7,779,614 B1 | 8/2010 | McGonagle et al. |
| 7,783,383 B2 | 8/2010 | Eliuk et al. |
| 7,784,244 B2 | 8/2010 | Siegel |
| 7,805,217 B2 | 9/2010 | Chudy et al. |
| 7,813,880 B2 | 10/2010 | Vaidya et al. |
| 7,818,177 B1 | 10/2010 | Bangalore et al. |
| 7,818,184 B2 | 10/2010 | Penny et al. |
| 7,818,950 B1 | 10/2010 | McGonagle et al. |
| 7,835,924 B1 | 11/2010 | Palazzolo et al. |
| 7,848,846 B2 | 12/2010 | Uema et al. |
| 7,861,495 B2 | 1/2011 | Yuyama et al. |
| 7,882,680 B2 | 2/2011 | Siegel et al. |
| 7,886,506 B2 | 2/2011 | Knoth et al. |
| 7,908,827 B2 | 3/2011 | Knoth |
| 7,922,037 B2 | 4/2011 | Ohmura et al. |
| 7,930,066 B2 | 4/2011 | Eliuk et al. |
| 7,930,869 B2 | 4/2011 | Rozenkranz |
| 7,946,101 B1 | 5/2011 | McGonagle et al. |
| 7,950,206 B2 | 5/2011 | Knoth |
| 2002/0042725 A1 | 4/2002 | Mayaud |
| 2002/0143429 A1 | 10/2002 | Yuyama et al. |
| 2002/0184051 A1 | 12/2002 | Yu et al. |
| 2003/0085235 A1 | 5/2003 | William et al. |
| 2003/0200726 A1* | 10/2003 | Rast ................ 53/443 |
| 2004/0064215 A1 | 4/2004 | Greeven et al. |
| 2004/0134043 A1 | 7/2004 | Uema et al. |
| 2004/0148054 A1 | 7/2004 | Schwartz |
| 2004/0249498 A1 | 12/2004 | William et al. |
| 2004/0261357 A1 | 12/2004 | Takahashi et al. |
| 2005/0139506 A1 | 6/2005 | Lorenzato |
| 2006/0086640 A1 | 4/2006 | Luciano et al. |
| 2006/0107623 A1 | 5/2006 | Rice et al. |
| 2006/0161298 A1 | 7/2006 | DiMaggio |
| 2006/0253346 A1 | 11/2006 | Gomez |
| 2007/0017181 A1 | 1/2007 | Jacobsen et al. |
| 2007/0125046 A1 | 6/2007 | Siegel et al. |
| 2007/0157548 A1 | 7/2007 | Knoth |
| 2007/0157551 A1 | 7/2007 | Yuyama et al. |
| 2007/0162179 A1 | 7/2007 | Freudelsperger |
| 2007/0169439 A1 | 7/2007 | Rice et al. |
| 2007/0173971 A1 | 7/2007 | Richardson et al. |
| 2007/0250346 A1 | 10/2007 | Luciano et al. |
| 2007/0267430 A1 | 11/2007 | Luciano et al. |
| 2007/0270998 A1 | 11/2007 | Luciano et al. |
| 2007/0289258 A1 | 12/2007 | Jung et al. |
| 2008/0071648 A1 | 3/2008 | Kim |
| 2008/0155718 A1 | 6/2008 | Kim |
| 2008/0162188 A1 | 7/2008 | Kripalani et al. |
| 2008/0190076 A1 | 8/2008 | Klingel et al. |
| 2008/0190953 A1 | 8/2008 | Mallett et al. |
| 2008/0195246 A1 | 8/2008 | Tribble et al. |
| 2008/0210701 A1 | 9/2008 | Cooper |
| 2008/0229718 A1 | 9/2008 | Feehan et al. |
| 2008/0300718 A1 | 12/2008 | Austin et al. |
| 2008/0312767 A1 | 12/2008 | Rice et al. |
| 2008/0312957 A1 | 12/2008 | Luciano, Jr. et al. |
| 2009/0012820 A1 | 1/2009 | Bishop et al. |
| 2009/0076338 A1 | 3/2009 | Zdeblick et al. |
| 2009/0076857 A1 | 3/2009 | Eletreby et al. |
| 2009/0120042 A1 | 5/2009 | Zieher |
| 2009/0132083 A1 | 5/2009 | Rice et al. |
| 2009/0133362 A1 | 5/2009 | Bentele et al. |
| 2009/0152291 A1 | 6/2009 | Ohmura et al. |
| 2009/0164042 A1 | 6/2009 | Handfield et al. |
| 2009/0210247 A1 | 8/2009 | Chudy et al. |
| 2009/0277815 A1 | 11/2009 | Kohl |
| 2009/0312855 A1 | 12/2009 | Biehler et al. |
| 2009/0319301 A1 | 12/2009 | Hyde et al. |
| 2009/0321296 A1 | 12/2009 | Luciano, Jr. et al. |
| 2009/0321465 A1 | 12/2009 | Knoth et al. |
| 2009/0321470 A1 | 12/2009 | Knoth |
| 2009/0321472 A1 | 12/2009 | Knoth |
| 2010/0004782 A1 | 1/2010 | Siegel et al. |
| 2010/0017031 A1 | 1/2010 | Rob et al. |
| 2010/0030667 A1 | 2/2010 | Chudy et al. |
| 2010/0031611 A1 | 2/2010 | Ali et al. |
| 2010/0042255 A1 | 2/2010 | Boutin |
| 2010/0069213 A1 | 3/2010 | Luciano, Jr. et al. |
| 2010/0070070 A1 | 3/2010 | Stemmle |
| 2010/0071320 A1 | 3/2010 | Ali et al. |
| 2010/0087935 A1 | 4/2010 | Pettus et al. |
| 2010/0089997 A1 | 4/2010 | Carson et al. |
| 2010/0100391 A1 | 4/2010 | Daya et al. |
| 2010/0106515 A1 | 4/2010 | McCoy |
| 2010/0121486 A1 | 5/2010 | Yuyama et al. |
| 2010/0145500 A1 | 6/2010 | Luciano, Jr. et al. |
| 2010/0147734 A1 | 6/2010 | Luciano, Jr. et al. |
| 2010/0152884 A1 | 6/2010 | Rice et al. |
| 2010/0153129 A1 | 6/2010 | Luciano, Jr. et al. |
| 2010/0153130 A1 | 6/2010 | Luciano, Jr. et al. |
| 2010/0161353 A1 | 6/2010 | Mayaud |
| 2010/0168904 A1 | 7/2010 | Henderson et al. |
| 2010/0172724 A1 | 7/2010 | Hawkes et al. |
| 2010/0174552 A1 | 7/2010 | Hawkes et al. |
| 2010/0176145 A1 | 7/2010 | Hawkes et al. |
| 2010/0198392 A1 | 8/2010 | Eliuk et al. |
| 2010/0228562 A1 | 9/2010 | Luciano, Jr. et al. |
| 2010/0230005 A1 | 9/2010 | Siegel et al. |
| 2010/0234982 A1 | 9/2010 | Sankaran et al. |
| 2010/0241270 A1 | 9/2010 | Eliuk et al. |
| 2010/0275552 A1 | 11/2010 | Siegel |
| 2010/0305975 A1 | 12/2010 | Daya et al. |
| 2011/0000170 A1 | 1/2011 | Burg et al. |
| 2011/0011034 A1 | 1/2011 | Mahar |
| 2011/0014351 A1 | 1/2011 | Reider et al. |
| 2011/0015782 A1 | 1/2011 | Chudy et al. |
| 2011/0060448 A1 | 3/2011 | Gotou et al. |
| 2011/0071667 A1 | 3/2011 | Spano, Jr. et al. |

(56) References Cited

U.S. PATENT DOCUMENTS

2011/0100863 A1 5/2011 Luciano
2011/0112686 A1 5/2011 Nolan et al.
2011/0113727 A1 5/2011 Bonner

OTHER PUBLICATIONS

United States Patent Office, Advisory Action issued in corresponding U.S. Appl. No. 13/546,035 (Jul. 28, 2014) (3 pages).

United States Patent Office, Notice of Allowance issued in corresponding U.S. Appl. No. 13/546,035 (Aug. 29, 2014) (6 pages).

USPTO, Office Action issued in U.S. Appl. No. 13/546,035 dated Dec. 20, 2013.

International Searching Authority, Search Report and Written Opiinion issued in related International application No. PCT/US12/46227 dated Sep. 24, 2012.

USPTO, Office Action issued in U.S. Appl. No. 13/546,035 dated May 8, 2014.

* cited by examiner

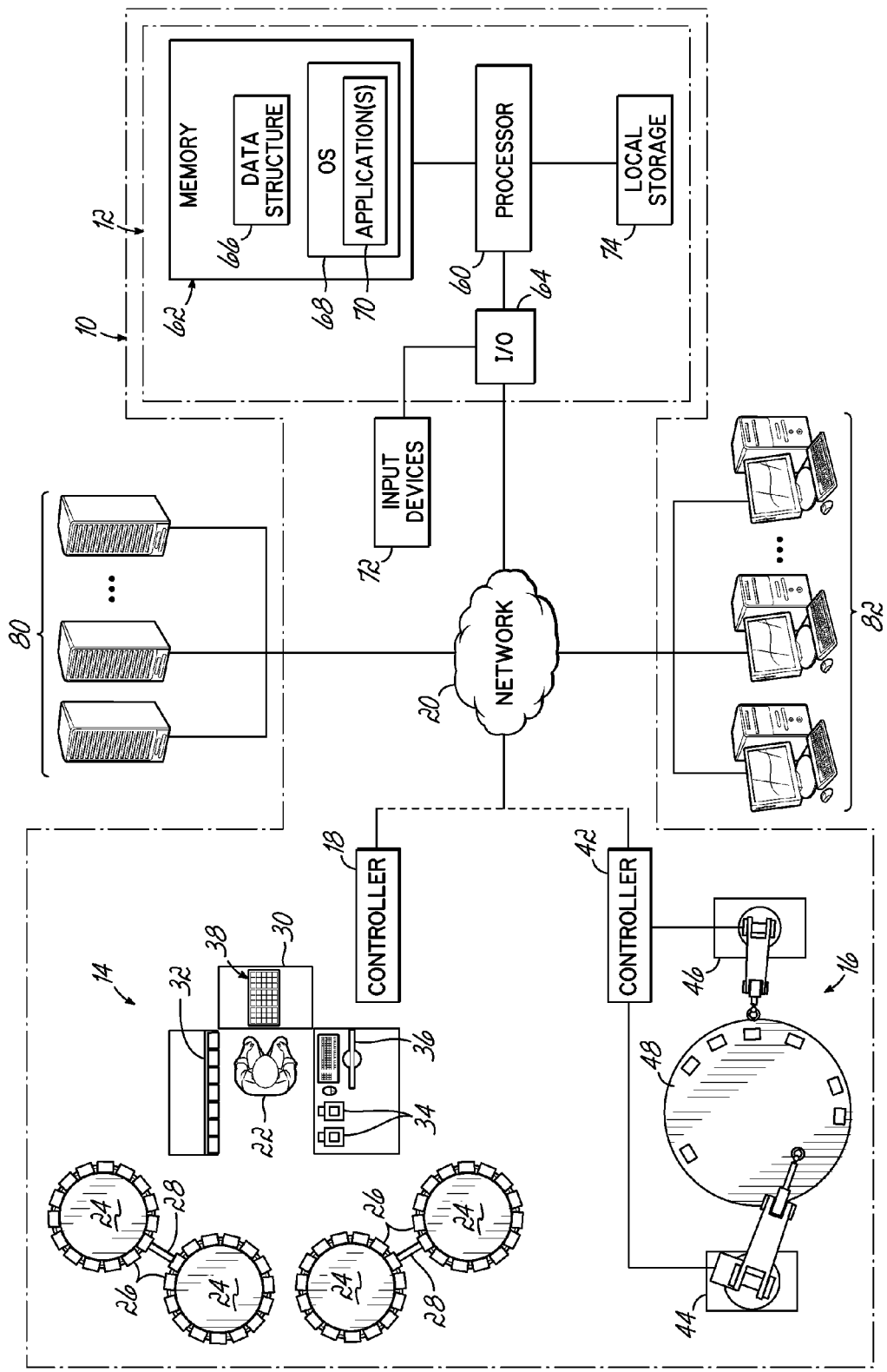

| | | Blister Pack | Compartment | | | | | | | |
|---|---|---|---|---|---|---|---|---|---|---|
| | | | A | B | C | D | E | F | G | H |
| Day 1 | Morning | 1 | Drug A | Drug C | | | | | | |
| | Lunchtime | 2 | Drug D | Blank | | | | | | |
| | Evening | 3 | Drug C | Blank | | | | | | |
| | Bedtime | 4 | Drug A | Blank | | | | | | |
| Day 2 | Morning | 5 | Drug A | Drug C | | | | | | |
| | Lunchtime | 6 | Drug B | Drug D | | | | | | |
| | Evening | 7 | Drug C | Blank | | | | | | |
| | Bedtime | 8 | Drug A | Blank | | | | | | |
| Day 3 | Morning | 9 | Drug A | Drug C | | | Blank | | | |
| | Lunchtime | 10 | Drug D | Blank | | | | | | |
| | Evening | 11 | Drug C | Blank | | | | | | |
| | Bedtime | 12 | Drug A | Blank | | | | | | |
| Day 4 | Morning | 13 | Drug A | Drug C | | | | | | |
| | Lunchtime | 14 | Drug B | Drug D | | | | | | |
| | Evening | 15 | Drug C | Blank | | | | | | |
| | Bedtime | 16 | Drug A | Blank | | | | | | |
| Day 5 | Morning | 17 | Drug A | Drug C | | | | | | |
| | Lunchtime | 18 | Drug D | Blank | | | | | | |
| | Evening | 19 | Drug C | Blank | | | | | | |
| | Bedtime | 20 | Drug A | Blank | | | | | | |
| Day 6 | Morning | 21 | Drug A | Drug C | | | | | | |
| | Lunchtime | 22 | Drug B | Drug D | | | | | | |
| | Evening | 23 | Blank | Blank | | | | | | |
| | Bedtime | 24 | Drug A | Blank | | | | | | |
| Day 7 | Morning | 25 | Drug A | Drug C | | | | | | |
| | Lunchtime | 26 | Drug D | Blank | | | | | | |
| | Evening | 27 | Blank | Blank | | | | | | |
| | Bedtime | 28 | Drug A | Blank | | | | | | |

| | | Blister Pack | Compartment | | | | | | | |
|---|---|---|---|---|---|---|---|---|---|---|
| | | | A | B | C | D | E | F | G | H |
| Day 1 | Lunchtime | 1 | Drug A | Drug C | | | | | | |
| | Evening | 2 | Drug C | Blank | | | | | | |
| | Bedtime | 3 | Drug A | Drug D | | | | | | |
| Day 2 | Lunchtime | 4 | Drug A | Drug C | | | | | | |
| | Evening | 5 | Drug C | Drug B | | | | | | |
| | Bedtime | 6 | Drug A | Drug D | | | | | | |
| Day 3 | Lunchtime | 7 | Drug A | Drug C | | | | | | |
| | Evening | 8 | Drug C | Blank | | | | | | |
| | Bedtime | 9 | Drug A | Drug D | | | | | | |
| Day 4 | Lunchtime | 10 | Drug A | Drug C | | | | Blank | | |
| | Evening | 11 | Drug B | Drug C | | | | | | |
| | Bedtime | 12 | Drug A | Drug D | | | | | | |
| Day 5 | Lunchtime | 13 | Drug A | Drug C | | | | | | |
| | Evening | 14 | Drug C | Blank | | | | | | |
| | Bedtime | 15 | Drug A | Blank | | | | | | |
| Day 6 | Lunchtime | 16 | Drug A | Blank | | | | | | |
| | Evening | 17 | Drug B | Blank | | | | | | |
| | Bedtime | 18 | Drug A | Drug D | | | | | | |
| Day 7 | Lunchtime | 19 | Drug A | Blank | | | | | | |
| | Evening | 20 | Blank | Blank | | | | | | |
| | Bedtime | 21 | Drug A | Drug D | | | | | | |

METHODS AND APPARATUS FOR AUTOMATED FILLING OF PACKAGINGS WITH MEDICATIONS

TECHNICAL FIELD

The invention relates generally to methods of filling packagings for medications and apparatus for assisting with automated filling of such packagings.

BACKGROUND

Prescription and non-prescription daily medications may be distributed to patients contained in a variety of different packages including conventional pill vials and blister packs. In many prescription dosing regimens, multiple oral medications are administered on a continuing basis to a patient at different times over the course of each day. The need to remove the oral medication from multiple different vials at specifically prescribed times each day can be confusing to a patient, especially senior patients. Patient confusion may contribute to partial prescription non-compliance or even complete prescription non-compliance if the patient fails to follow treatment directions.

To address this non-compliance concern, it would be desirable to provide a certain number of medication packages for each day that contain all of the medications to be consumed at specified times in the day (e.g., morning, lunchtime, evening, bedtime). Additionally, when multiple oral medications are to be administered to a patient, any potential drug contra-indication (whether detrimental or not) and the desired dosage intervals for each medication must be considered when determining how to fill these packages of medications. If, for example, the medication packages are provided for four specified daily times, each medication to be administered during that day must be allocated to the separate packages so as to maintain the desired dosing intervals and so as to avoid detrimental medication contra-indications.

Moreover, some patients have particular administration time preferences or life style choices that prevent them from reliably taking medications at a particular time of day, such as patients who do not awaken before lunchtime. For these patients, the medication for each day must be allocated to a smaller number of packages to avoid prescription non-compliance. However, detrimental drug contra-indications must necessarily be avoided even when using fewer medication packages per day.

In an exemplary application in which a patient receives four separate packages of medications for each day, a monthly supply of the medications will require up to 120 packages to be filled and verified. Some conventional filling systems move each package to be filled along a complex and lengthy path past a high number of bulk containers so that each medication to be placed in the packaging will be dispensed as the packages move along the complex and lengthy path. Although such systems have utility when filling pill bottles with multiple doses of an individual medication, these systems are far less efficient when dispensing single unit doses of medication into a plurality of packagings for each patient. A pharmaceutical filling operation may be responsible for thousands of patients per month, which requires hundreds of thousands of packagings to be individually filled and verified. The conventional filling systems described above do not provide sufficient capacity to fill and verify the high number of packagings required on a monthly basis, and these filling systems are prone to making additional filling mistakes as the movement velocity of packagings through the system increases.

Consequently, improved methods and apparatus for filling packages with various medications are needed that can improve prescription compliance and provide sufficient filling capacity to serve thousands of patients per month.

SUMMARY OF THE INVENTION

According to one embodiment of the invention, a method for filling packagings with at least one medication includes receiving filling instructions for an order and operating an automated packaging station to fill the plurality of the packagings for the order. The filling instructions include an allocation of medications to the plurality of packagings, and each packaging is adapted to receive at least one of the medications (e.g., as one tablet, a partial or half tablet, multiple tablets, or a dose in a smaller blister package) to be taken by the patient. The operation of the automated packaging station includes positioning a plurality of cassettes containing the medications needed for the order onto a feeder base at a single filling location. The operation also includes moving each of the plurality of packagings to the filling location and actuating at least one of the plurality of cassettes at the feeder base simultaneously and according to the filling instructions when each packaging is located at the filling location. Thus, the feeder base simultaneously deposits each of the medications needed for that packaging into that packaging. As a result, the medications are rapidly and accurately placed into easy-to-use packagings for patients, thereby improving drug administration compliance and the prescription filling process.

In one aspect, receiving filling instructions for the order further includes analyzing a plurality of prescriptions for the patient and generating the filling instructions based at least in part on the analyzed prescriptions. Generating the filling instructions may also include receiving a dosage schedule for each medication and allocating each medication from the prescriptions to the plurality of packagings based on the dosage schedules. Any undesirable drug contra-indications in the packagings may then be identified so that the allocation is modified to avoid such undesirable drug contra-indications. Generating the filling instructions may also include receiving administration time preferences from the patient or prescribing physician and modifying the allocation of medications to the packagings based on these administration time preferences.

In another aspect, receiving filling instructions further includes retrieving a list of pending orders for a plurality of patients and excluding from this list any orders that do not require filling at the automated packaging station. The list of orders if sorted to establish a priority for which pending order should be filled first. The automated packaging station then checks to see if sufficient inventory is on hand to fill the first order in the sorted list. If there is sufficient inventory at the automated packaging station, then that first order is assigned to be filled at the automated packaging station by providing the filling instructions to a machine controller of the automated packaging station.

The automated packaging station includes storage carousels containing cassettes with bulk supplies of medications, a turntable assembly including the feeder base, and a first robot configured to selectively collect and move the cassettes. Operating the automated packaging station further includes moving the plurality of cassettes with the first robot between the storage carousels and the turntable assembly. The turntable assembly moves with an indexed movement to sequentially position each of the plurality of packages at the filling location. Moreover, each packaging may include a plurality of compartments and the feeder base may include a plurality of chutes extending between the cassettes on the feeder base and these compartments of a packaging at the filling location. When the cassettes are simultaneously actuated to dispense unit doses of medication that are to go in the packaging, the unit doses are directed through the corresponding chutes into the plurality of compartments.

In yet another aspect, the turntable assembly also includes a loading staging table and an unloading staging table adjacent to the feeder base. Moving the cassettes with the first robot then further includes retrieving a first set of cassettes for the storage carousels and depositing the first set of cassettes onto the loading staging table. This movement also includes moving a second set of cassettes from the feeder base onto the unloading staging table, and moving the first set of cassettes from the loading staging table onto the feeder base. The first robot then retrieves the second set of cassettes from the unloading staging table and returns those cassettes to the storage carousels. The first and second sets of cassettes may correspond to two different sets of packagings requiring different medications, and the movement of packagings and actuation of cassettes for one set of cassettes continues at the feeder base while the other set of cassettes is moved by the first robot. Thus, the simultaneous filling of packagings during replacement of a previously-used set of cassettes with a new set of cassettes enables substantially continuous filling operation at the turntable assembly.

The first robot may include a first gripping head operable to hold up to four cassettes and a second gripping head operable to hold up to eight cassettes. The first robot uses the first gripping head to move the cassettes between the storage carousels and the loading and unloading staging tables. The first robot uses the second gripping head to move the cassettes between the feeder base and the loading and unloading staging tables. Each of the loading and unloading staging tables includes a plurality of stationary platens and a plurality of moveable platens to receive cassettes. The moveable platens are moved between raised and lowered positions to provide access to only four cassettes at once whenever the first robot is using the first gripping head. When the first robot is using the second gripping head, the moveable platens are held in the lowered position so as to keep all of the cassettes on the staging tables generally coplanar.

In one embodiment, the automated packaging station also includes a refill window accessible to the first robot and to human operators outside a robotic work zone. Operating the automated packaging station then includes detecting that at least one cassette requires refill of bulk supply or repair. That cassette is moved by the first robot to the refill window from the storage carousels or from the turntable assembly, and a signal is sent to the human operators to prompt removal of that cassette from the refill window. When the cassette has been refilled or repaired and replaced in the refill window, the first robot retrieves the cassette from the refill window and deposits it back to the storage carousels or to the turntable assembly.

In another aspect, the turntable assembly includes a rotary dial with a plurality of nests each configured to receive one of the plurality of packagings. Operating the automated packaging station includes rotating each nest underneath at least one packaging magazine configured to position an empty packaging onto the nest. The rotary dial rotates each nest containing a packaging underneath the feeder base to receive the medications from the cassettes at the feeder base. The rotary dial then rotates each nest to an unloading station at which a second robot is stationed to remove filled packagings from the nests.

The plurality of packagings may be divided into multiple sets of packagings configured to receive different pluralities of medications. Operating the automated packaging station includes positioning each empty packaging of a first set of the packagings onto consecutive nests rotating around the rotary dial with the at least one packaging magazine and leaving one empty nest on the rotary dial before positioning each empty packaging of a second set of the packagings onto the rotary dial. The empty nest rotates into the filling location during exchange and positioning of a next plurality of cassettes onto the feeder base such that any medications accidentally dispensed during this positioning are not deposited into a packaging.

In another aspect, the rotary dial rotates each filled packaging in the nests through a fill verification station configured to verify the deposit of medications by the feeder base. The rotary dial may also rotate each filled packaging to an additional filling location at an alternative loading mechanism configured to deposit medications that cannot be dispensed by cassette into the packagings. The rotary dial may then rotate each filled packaging to another fill verification station and a product verification station configured to use laser spectroscopy to verify the identity of medications deposited into the packagings. The rotary dial rotates each filled packaging to a printer assembly that applies a sealing cover onto the packagings. The printer assembly prints patient and drug identification information on the covers in the form of machine readable indicia and human readable labels. The printer assembly may modify the regular information printed on the covers in the event that the deposit of medications into a packaging is not verified by one of the verification stations, and this will provide an indication that downstream manual inspection is required for that packaging.

In yet another aspect, the packaging magazine includes a magazine channel with a stack of empty packagings and a gripping head assembly. Operating the automated packaging station further includes grabbing one empty packaging from the magazine channel with the gripping head assembly. The gripping head assembly rotates the empty packaging to face toward a nest without a packaging and then positions the empty packaging into such a nest. The unloading station may further include a second robot and at least two drawers configured to receive trays that receive the filled packagings. Operating the automated packaging station further includes moving the filled packagings from the rotary dial to the trays with the second robot. When one of the trays is sensed to be filled with packagings, a human operator is prompted to open the drawer and replace the filled tray with an empty tray.

In another embodiment according to the invention, an automated packaging station is configured to fill packagings with at least one medication. The station includes a robotic work zone enclosed by a barrier wall and a plurality of storage carousels in the robotic work zone. The storage carousels hold cassettes each containing a bulk supply of a medication. The station also includes a turntable assembly in the robotic work zone and including a single filling location and a feeder base. The feeder base receives a plurality of cassettes from the storage carousels and then actuates simultaneous dispensing of medications from at least one of the plurality of cassettes when each packaging is located at the filling location. The station also includes a first robot in the robotic work zone for selectively moving cassettes between the storage carousels and the turntable assembly. The station further includes a machine controller having a processor and a memory, and program code resident in the memory and configured to be executed by the processor. The program code operates to receive filling instructions for an order and to operate the elements in the robotic work zone to fill the packagings with the at least one medication according to the filling instructions. The automated packaging station rapidly and accurately places medications into easy-to-use packagings for patients, thereby improving drug administration compliance and the prescription filling process.

The methods and stations of this invention improve speed and quality/accuracy of individualized pharmaceutical packaging.

BRIEF DESCRIPTION OF THE SEVERAL VIEWS OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

FIG. 1 is a schematic view of an exemplary embodiment of a drug packaging system according to the invention, the drug packaging system including a manual packaging station and an automated packaging station.

FIG. 21C is a schematic chart used to illustrate the generation of packaging instructions based on the four prescriptions of FIG. 21B.

FIG. 21D is a schematic chart used to illustrate the generation of packaging instructions based on the four prescriptions of FIG. 21B as well as any patient preferences or drug contraindications.

DETAILED DESCRIPTION

Figure 2A:
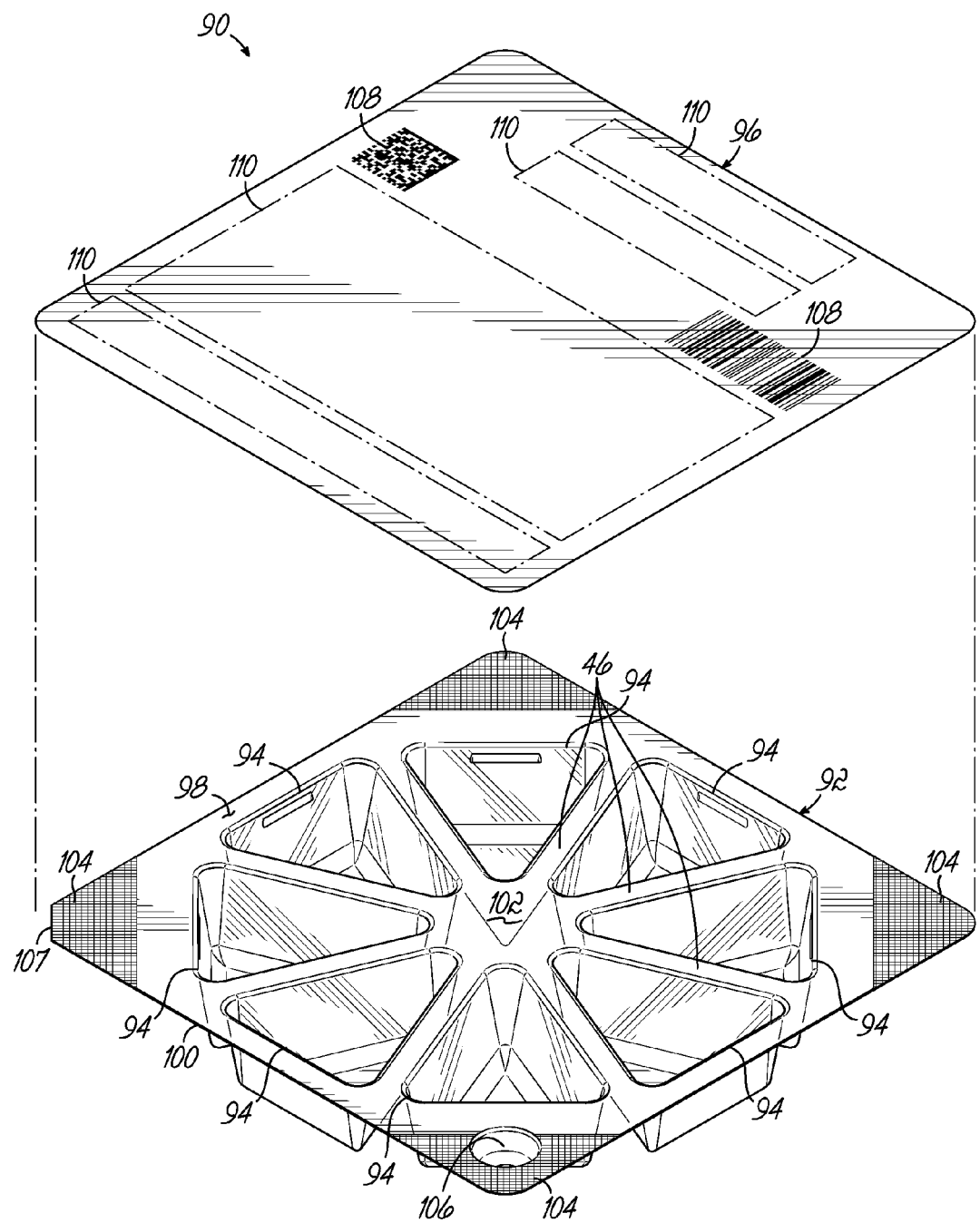
FIG. 2A is a partially exploded perspective view of one embodiment of a medication packaging filled by the drug packaging system of FIG. 1.

With reference to FIG. 1, one exemplary embodiment of a drug packaging system 10 consistent with the invention is shown. The drug packaging system 10 includes a controller 12, one or more manual packaging stations 14, and one or more automated packaging stations 16. The controller 12 is configured to actuate the manual packaging stations 14 and the automated packaging stations 16 to fill a plurality of patient specific drug packages with a plurality of medications. One example of the patient specific drug packaging used throughout the following description is a blister pack (not shown in FIG. 1) described in further detail with reference to FIGS. 2A and 3 below. It will be understood that other types of drug packaging may be used in other embodiments of the invention. The blister packs are designed for distributing medications that are administered to a patient as part of long-term, maintenance care for chronic ailments and conditions. Patients, such as elderly or senior patients, may daily dispense and consume one or more medications (such as oral medications or other solid products) from one of the blister packs at pass times during the day, such as morning, lunchtime, evening, and bedtime. The blister packs conveniently simplify the administration of multiple medications by grouping all of the unit doses to be taken at a particular pass time into a single drug package. As a result, the blister packs improve drug delivery accuracy and medication regimen compliance, especially for senior aged patients who may be living at home independently or cared for in an assisted-care facility. Consequently, the manual and automated packaging stations 14, 16 are configured to optimize the filling process so that a maximum number of patients, each of whom may require 120 blister packs or more per month, may be served monthly by the drug packaging system 10. For example, in the scenario when additional blister packs are prepared for PRN or "take as needed" use, any number of blister packs may be filled for a particular patient in each month. The following description will focus on the regularly scheduled medication passes, but it will be understood that additional PRN blister packs or other blister packs may also be filled using the apparatus and methods described below.

With continued reference to FIG. 1, the manual packaging station 14 includes a machine controller 18 operatively connected to the controller 12 via network 20. The machine controller 18 of the manual packaging station 14 is configured to execute program code configured to direct one or more elements of the manual packaging station 14 to provide filling instructions to an employee 22 stationed at the manual packaging station 14, thereby causing the employee 22 to fill patient specific drug packages (e.g., the blister packs). The manual packaging station 14 is described in detail in commonly-owned U.S. Patent Application No. 61/506,390, the disclosure of which is hereby incorporated by reference in its entirety. The manual packaging station 14 may be used as an alternative to the automated packaging station 16 to fill all of the blister packs in an order, as a supplemental station to fill only those blister packs requiring manual attention or filling (e.g., medications not dispensable from cassettes, for example), or as a verification station for post-processing quality assurance following filling at the automated packaging station 16. A brief overview of the elements of the manual packaging station 14 shown in FIG. 1 is provided as follows.

The manual packaging station 14 includes a plurality of storage carousels 24 each adapted to hold various canisters 26 filled with different medications. One or more indicator panels 28 also known as light trees are positioned adjacent the storage carousels 24 to provide a visual indication to the employee 22 where to retrieve necessary canisters 26 and where to replace canisters 26 after use. The manual packaging station 14 also includes a loading table 30, a staging bar 32 configured to hold canisters 26 being actively used, a counter 34 configured to dispense pills from the canisters 26, and a visual display monitor 36 configured to provide operational instructions to the employee 22. Using instructions from the visual display monitor 36 and various indicator lights (including those at the indicator panels 28), the employee 22 retrieves all the canisters 26 necessary to fill a tray of blister packs from the storage carousels 24 and positions those canisters 26 on the staging bar 32. The employee 22 then individually takes the canisters 26 to the counter 34 to dispense a desired number of unit doses, which are then placed manually into the appropriate cavities of the blister pack at the loading table 30. To assist with accurate manual placement of unit doses into the blister packs, the loading table 30 includes a shutter assembly 38 that provides selective access to only one of the cavities of each blister pack at a time. After each of the canisters 26 has been used to fill the blister packs, the employee 22 replaces the tray of blister packs and repeats the process above for the new tray of blister packs. It will be understood that the layout of the elements of the manual packaging station 14 are shown as a exemplary layout, but the layout of these elements may be modified from the schematic example shown in FIG. 1.

Similarly, the automated packaging station 16 includes a machine controller 42 operatively connected to the controller 12 via network 20. The machine controller 42 of the automated packaging station 16 is configured to execute program code configured to operate filling machinery, such as a first robot 44 and a second robot 46 at a turntable assembly 48, to fill patient specific drug packages (e.g., the blister packs). The automated packaging station 16 and the operation thereof are described in considerable detail with reference to FIGS. 4 through 16 below. In short, the first and second robots 44, 46 are configured to move cassettes containing medications and blister packs to and from the turntable assembly 48 such that the cassettes dispense the medications into the appropriate blister packs, and then the filled blister packs are removed into trays for downstream processing and shipping to the patient. Although both the manual packaging station 14 and the automated packaging station 16 provide the same result of trays containing filled blister packs, the automated packaging station 16 significantly increases the efficiency and the accuracy of the filling process because substantially no human interaction is required to fill the blister packs at the automated packaging station 16. Furthermore, each robotic filling step is verified for accuracy and quality assurance immediately after the filling step.

The controller 12 is shown in further detail in FIG. 1. To this end, controller 12 includes processor 60, memory 62, and I/O interface 64. Controller 12 further includes data structure 66 and operating system 68 resident in memory 62, where operating system 68 may further include one or more applications 70 configured to execute within operating system 68. In this regard, one of the applications 70 executed by the controller 12 is programmed to convert a list of prescribed medications and dosage instructions for a patient into filling instructions that explain how to fill the up to 120 blister packs at the manual packaging station 14, at the automated packaging station 16, or at both stations 14, 16. It will be appreciated that the machine controllers 18 and 42 may also include configurations similar to the configuration described above for controller 12. Input devices 72 may be operatively connected to controllers 12, 18, 42, for inputting data and/or prescriptions into the drug packaging system 10. Input devices 72 include, for example, a keyboard, a computer mouse, a barcode scanner, an optical scanner, electronic file or data transfer mechanisms, and other known scanning or input mechanisms. In addition, controller 12 includes local storage 74, which may also be operatively connected to machine controllers 18, 42.

Furthermore, drug packaging system 10 may be operatively connected to one or more resources over network 20, such as external resources 80 and/or remote terminals 82. External resources 80 may include data systems configured to communicate and interface with drug packaging system 10. For example, external resources 80 may include a drug information database, and an external system may be configured to receive a query from drug packaging system 10 corresponding to one or more drug types, the external resources 80 being configured to process the received query and transmit data related to the one or more drug types to drug packaging system 10. In addition, remote terminals 82 may be configured to transmit data to and receive data from drug packaging system 10. For example, remote terminals 82 may be configured to receive input from one or more users and transmit the input data to drug packaging system 10.

The routines executed to implement the embodiments of the invention, whether implemented as part of an operating system 68 or a specific application 70, component, program, object, module or sequence of operations executed by one or more specific or general purpose controllers of the control system will be referred to herein as "computer program code" or simply "program code." For example, referring to FIG. 1, the computer program code typically comprises one or more instructions that are resident at various times in various memory 62 and/or storage devices operatively connected to controllers 12, 18, 42 of the drug packaging system 10, and that, when executed by one or more processors 60 of the controllers 12, 18, 42 of the drug packaging system 10, may cause the controllers 12, 18, 42 to perform the steps necessary to execute steps, elements, and/or blocks embodying the various aspects of the invention. In addition, those skilled in the art will recognize that embodiments of the invention are not limited to particular types or configurations of processors or memory and/or storage devices.

Figure 3:
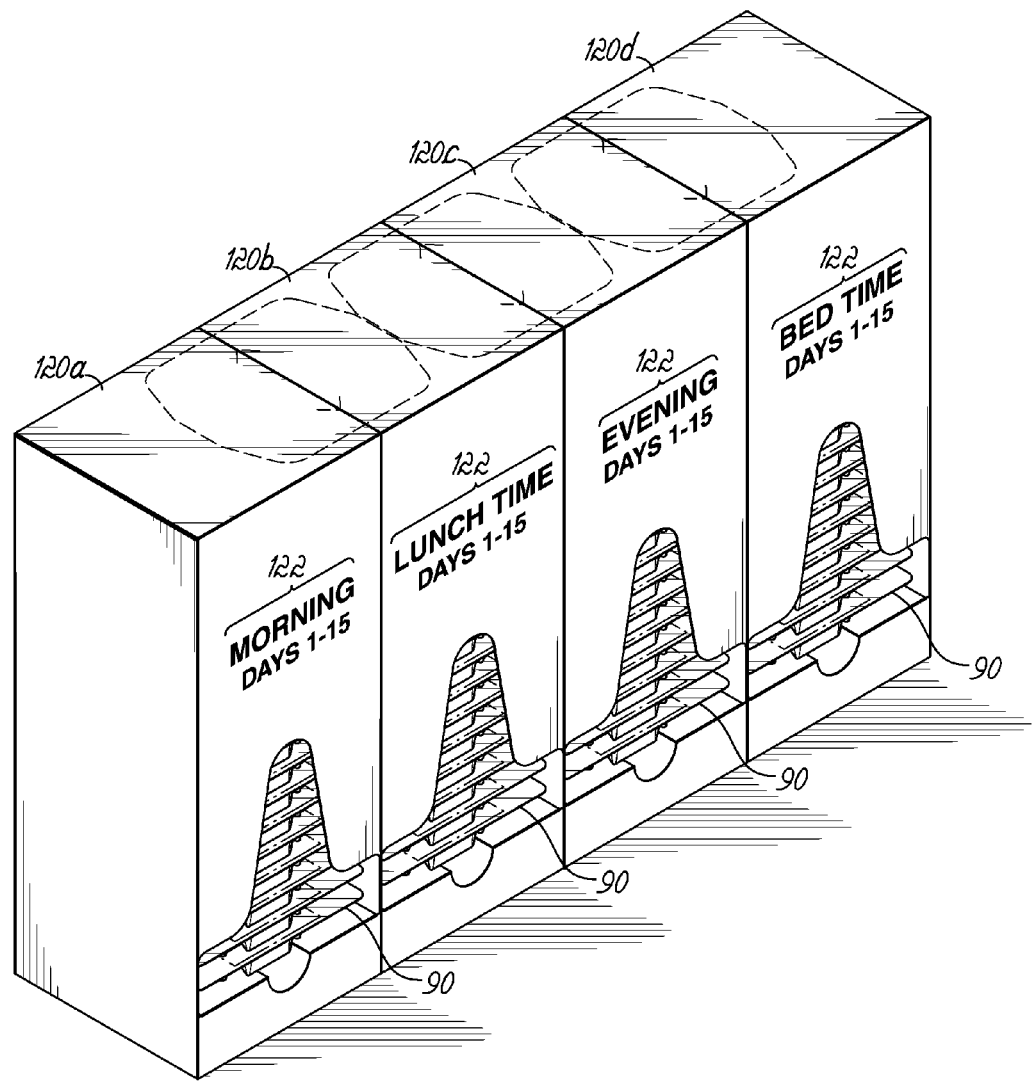
FIG. 3 is a perspective view of a set of cartons containing the medication packaging of FIG. 2A after a filling process.

Before describing the particular details of the automated packaging station 16, it will be advantageous to describe the particular types of medication packaging designed for use with the drug packaging system 10. In this regard, one embodiment of a blister pack 90 used in the filling process is shown in FIGS. 2A and 3. The blister pack 90 may be the medication packaging described in detail in commonly-owned U.S. patent application Ser. No. 13/153,900 to Carson et al., the disclosure of which is hereby incorporated by reference in its entirety. To this end, the blister pack 90 includes a body 92 with a plurality of compartments 94 and a lidding sheet in the form of a cover 96. The cover 96 is joined to the body 92 in order to seal closed the compartments 94. In the representative embodiment, the number of compartments 94 is eight, but the total number of compartments 94 may be modified in other embodiments. Each of the compartments 94 is configured to receive and hold a unit dose or a portion of a unit dose of a medication. For example, the compartments 94 may be configured to receive one tablet, a partial or half tablet, multiple tablets, or a dose in a smaller blister package. After the medications are placed into the compartments 94 and the cover 96 is attached to the body 92, the blister pack 90 is thus sealed to prevent the ingress of environmental contaminants and then is in a state prepared for subsequent distribution to a patient.

Figure 2B:
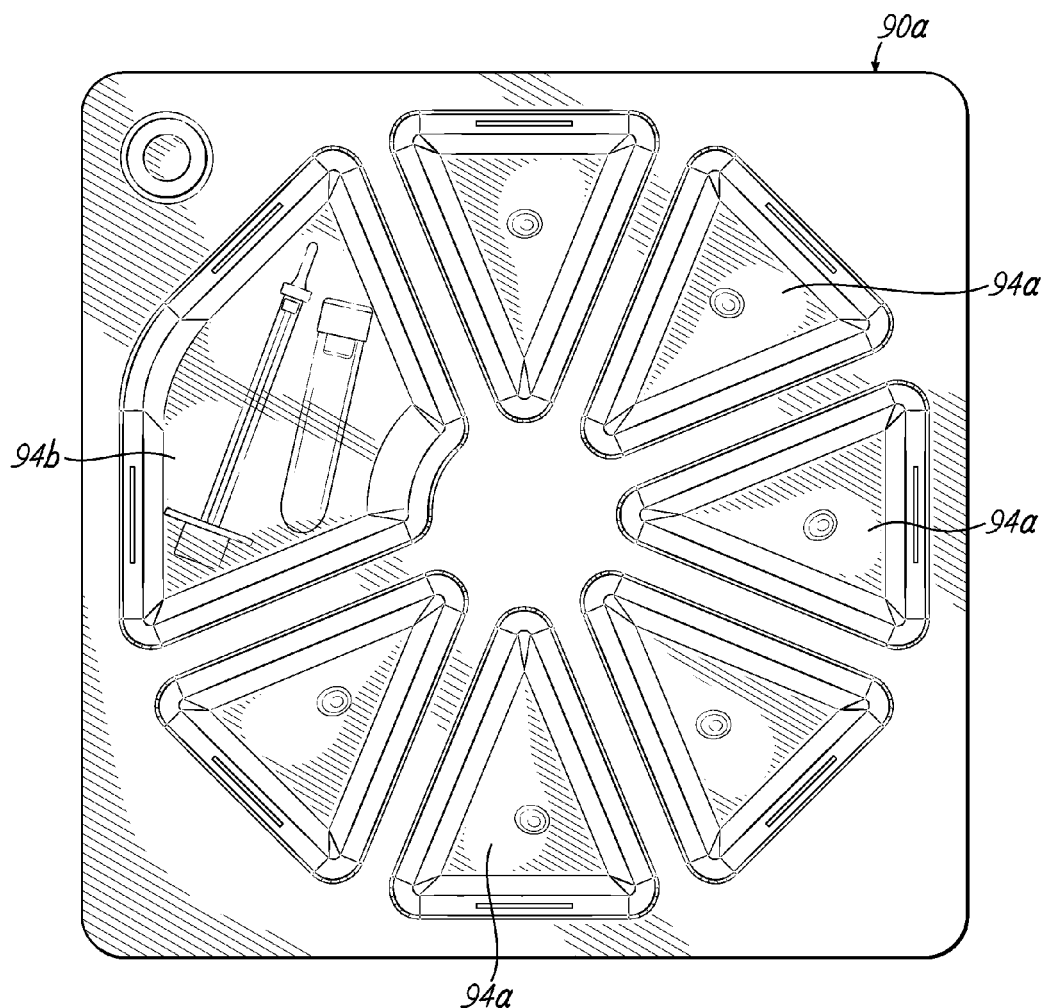
FIG. 2B is a bottom view of another embodiment of a medication packaging filled by the drug packaging system of FIG. 1.
Figure 2C:
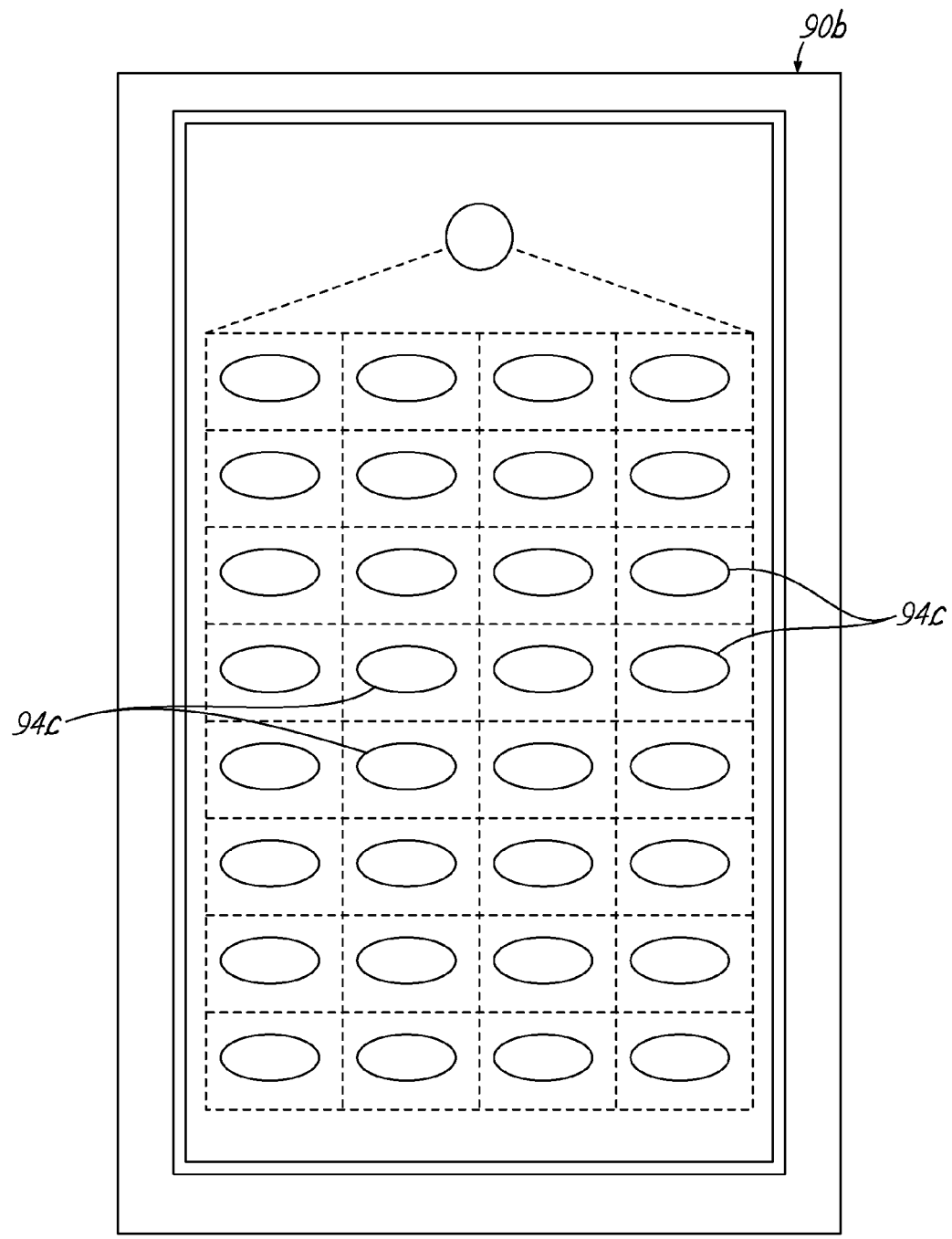
FIG. 2C is a top view of another embodiment of a medication packaging filled by the drug packaging system of FIG. 1.

As described above, the number of compartments 94 in the blister pack 90 and the blister pack design itself may be modified in other embodiments of the drug packaging system 10. Two examples of such modified packagings 90a, 90b are shown in FIGS. 2B and 2C. FIG. 2B illustrates an alternative blister pack 90a having a similar general shape as the blister pack 90 shown in FIG. 2A, but two of the wedge-shaped compartments 94a for holding a unit dose have been replaced and combined into one larger (and possibly deeper), elongate compartment 94b. As schematically shown in FIG. 2B, this larger compartment 94b is configured to hold larger items such as vials of medication or injectable medications. This blister pack 90a may be filled using the equipment of the automated packaging station 16 described in full detail below without significant modifications to that equipment. FIG. 2C illustrates an alternative blister card 90b configured to receive a two-dimensional matrix or grid of unit doses of a particular medication for a month (or some other time period within the month). To this end, the blister card 90b includes about 30 individual blister compartments 94c configured to receive daily doses of a particular medication. A similar type of packaging to this blister card 90b is described in commonly-owned U.S. Pat. No. 7,328,801 to Iossi, the disclosure of which is hereby incorporated by reference in its entirety. It will be understood that the equipment of the below-described automated packaging station 16 would require some modification to accommodate the blister cards 90b, but the principles of filling operation would remain the same.

Returning to the embodiment shown in FIG. 2A, the body 92 includes a top surface 98 that surrounds each of the compartments 94 and extends to an outer periphery 100 of the body 92. The compartments 94 of the illustrated embodiment are formed as triangular or wedge-shaped cavities extending downwardly from the top surface 98 and arranged about a central region 102 of the top surface 98. The top surface 98 may include corner regions 104 modified with a pattern of surface-area reducing features that consist of non-planar structures formed into the material of the body 92. These features at the corner regions 104 assist a patient with easy removal of the cover 96 after delivery of the filled blister pack 90 to the patient. The top surface 98 is free of score lines, lines of weakening, perforated seams, and the like. This structural omission is permitted because the individual compartments 94 are not intended to be severed from the body 92.

The body 92 of the blister pack 90 also includes an indexing feature 106 in the representative form of a blind, hollow post that is disposed in the vicinity of one of the corner regions 104 in the representative embodiment. The indexing feature 106 projects away from the plane of top surface 98 in the same direction as the compartments 94. The indexing feature 106 may be utilized to rotationally orient the body 92, for example, relative to a tray or relative to the turntable assembly 48 previously described. In this manner, the angular orientation of multiple different blister packs 90 can be reproducibly established for positioning the compartments 94 at known and fixed positions during a filling operation. In addition, another of the corner regions 104 adjacent to the corner region 104 with the indexing feature 106 further includes a notch 107 cut away from the corner region 104. This notch 107 is used to verify the orientation of the blister pack 90 upon manual entry into packaging magazines of the automated packaging station 16, as described in further detail with reference to FIGS. 8A through 8F below. The notch 107 is oriented as a generally parallel cut to the outermost wall of the closest compartment 94.

The cover 96 is adapted to be heat sealed or otherwise adhered to the body 92 after the filling process. The cover 96 is a thin sheet of material including machine readable indicia 108 that may be scanned after the filling process. Although two different machine readable indicia 108 are shown on the cover 96, it will be understood that more or fewer of these indicia 108 may be printed on the cover 96 in other embodiments consistent with the invention. The cover 96 may also include human readable labels 110 containing information on the medications contained within the blister pack 90 and the intended patient. The machine readable indicia 108 and human readable labels 110 may be printed on the cover 96 prior to adherence of the cover 96 to the body 92. More specifically, the covers 96 may be printed with any known type of machine readable indicia 108 (e.g., barcodes, OCR, OVR) and any type of human readable labels 110 by a station configured to print and apply these labels in series immediately after the blister pack 90 are filled and verified. As will be described in further detail below, this station operates to print only partial or different indicia 108 and labels 110 in the event of an error detected during verification, thereby prompting operators to address these errors manually during downstream processing.

As briefly described above, the blister packs 90 are best suited for distributing medications that are administered to a patient on a regular or irregular dosage interval as part of long-term, maintenance care. Each of the medications may be administered to the patient by oral or other consumption once a day (QD), two times a day (BID), three times a day (TID), four times a day (QID), or on irregular or different intervals (e.g., once per day on Mondays, Wednesdays, and Fridays). Certain oral medications should be administered to the patient by oral consumption during a specific medication pass (such as only at bed time or morning). The dosage interval for each medication and any time-of-day restrictions, personal administration time preferences, and/or drug contra-indications may be factors used to allocate the medications to a specific blister pack 90 designated for administration in a particular medication pass. The consideration of each of these factors in determining how a month-long (i.e., 30-day) supply of blister packs 90 or medication passes should be filled is described in further detail below. Once the medications have been allocated to the appropriate blister packs 90 for a 30-day period (hereinafter referred to generally as a "month"), then the filling process described in further detail below may be conducted at the automated packaging station 16 to fill each of the blister packs 90 for that month. It will be understood that the "month" may begin on any day of a calendar week or month depending on when the medications are being filled and delivered to a particular patient, and it will also be understood that the term "month" could also refer to a 28-day period, a 31-day period, etc. in other embodiments.

With reference to FIG. 3, filled blister packs 90 may be distributed in a set of multiple cartons 120a, 120b, 120c, 120d for delivery to the residence of the patient. Each of the cartons 120a, 120b, 120c, 120d may initially contain or house up to a month's supply of blister packs 90 containing medication passes intended to be administered to the patient at nominally the same designated time on successive days of a month as identified by indicia 122 on the cartons or the human readable labels 110 on the covers 96 of the blister packs 90. In the illustrated example, the cartons 120a, 120b, 120c, 120d may contain respective stacks of blister packs 90 sufficient to provide a half-month supply (in the exemplary embodiment) of medications for administration at four different daily times each day in a given month. However, each of the cartons 120a, 120b, 120c, 120d may be reconfigured and resized to provide a full month supply of medications for administration at the four times each day. It will be appreciated that the cartons 120a, 120b, 120c, 120d may be reconfigured as a single package or any number of different packages corresponding to subsets of the blister packs 90 to be delivered to the patient as a supply of medicament, whether used during schedule medication passes or for PRN purposes.

In the foregoing and following description, reference is made generally to "oral medications." Each of the oral medications configured to fill the blister packs 90 may be any type of ingestible substance capable of being categorized as an oral medication. It will be understood that the use of the term "oral medications" does not limit the blister packs 90 to being filled with just orally consumed medications, as other types of medications applied in different manners may also be inserted in the filling process. The ingestible substance comprising each of the oral medications may include, but is not limited to, one or more pharmaceuticals, medicaments, one or more compositions, one or more drugs, one or more vitamins, one or more mineral supplements, and one or more placebos, either alone or in combination and may be dispensed by prescription or over-the-counter. The medications may be provided in various dosage forms such as pills, tablets, capsules, vials, ampoules, gel capsules, solids, liquids, powders, etc. A "unit dose" in the context of this invention is an amount of the medication or solid product that is administered to a patient in a single dose.

Now with specific reference to FIGS. 4 through 16, the automated packaging station 16 according to an exemplary embodiment of the current invention is shown in further detail. As shown in the illustration of the entire automated packaging station 16 at FIG. 4, the automated packaging station 16 includes a barrier wall 150 surrounding and separating a robotic work zone 152 from an operator work zone 154 located outside the barrier wall 150. The barrier wall 150 consists of a plurality of movable framed panels typically formed from plexiglass or another transparent material such that operators 156 can observe the operations performed within the robotic work zone 152. The barrier wall 150 may optionally include a door 158 which may be opened (as shown in phantom in FIG. 4) to provide access into the robotic work zone 152 when necessary. However, the robotic work zone 152 is generally kept free from any human operators 156 during the normal operation of the automated packaging station 16. The movement of drugs and blister packs 90 and the filling of the blister packs 90 occurs entirely within the robotic work zone 152, while the operator work zone 154 is designed to enable operators 156 to monitor the filling process, guide replenishment of drugs when necessary, and move trays of filled blister packs 90 out of the robotic work zone 152 for downstream processing and shipping to patients.

Figure 4:
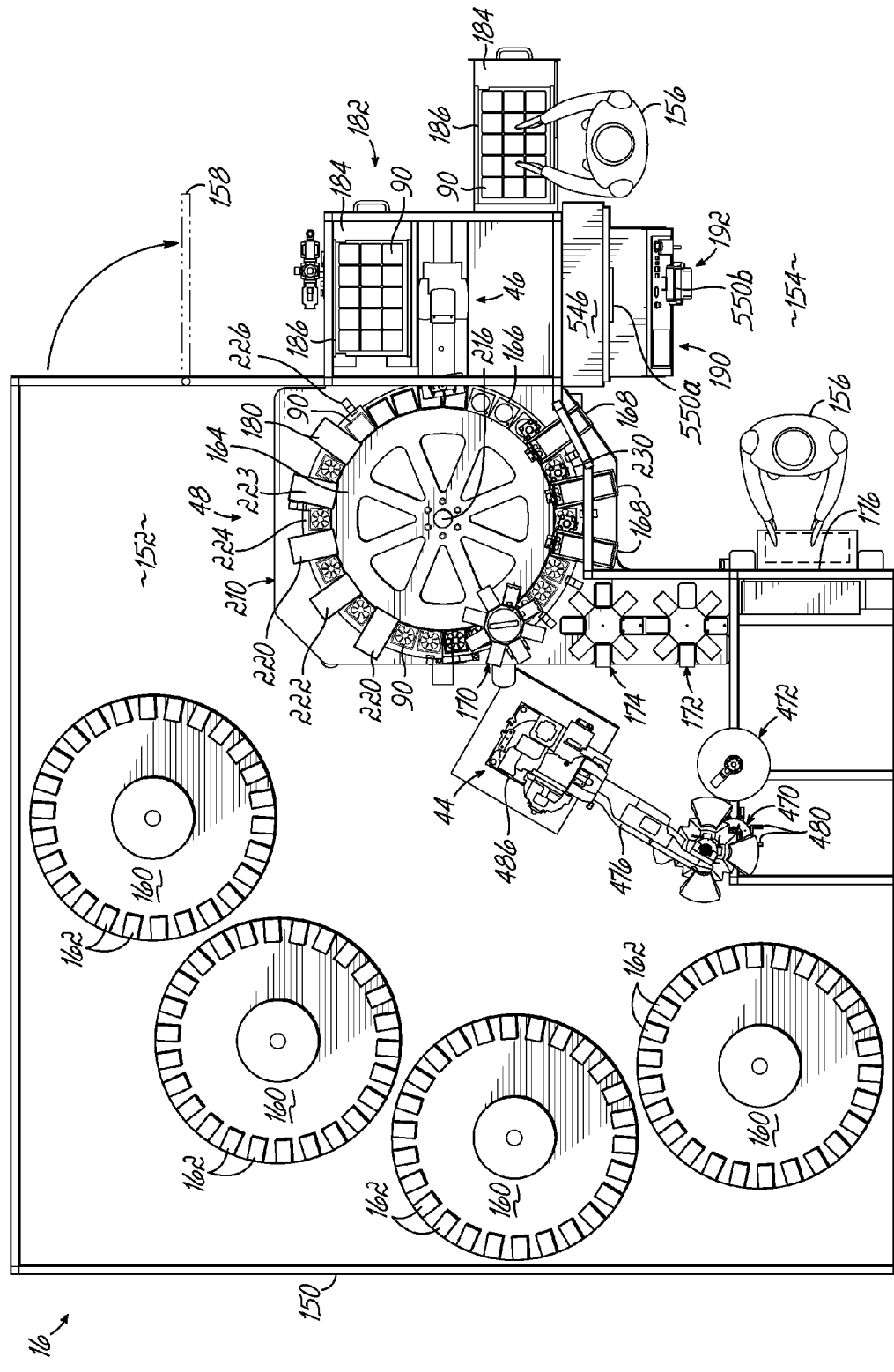
FIG. 4 is a top view of the automated packaging station of FIG. 1.

With continued reference to FIG. 4, the general structure contained within the robotic work zone 152 is as follows. The automated packaging station 16 includes a plurality of storage carousels 160 adapted to hold various cassettes 162 filled with bulk stock of different oral medications. The storage carousels 160 are indexed such that the machine controller 42 continuously knows the location of any particular cassette 162. In the exemplary embodiment, the storage carousels 160 are capable of retaining up to 864 cassettes 162 containing bulk supply of medications. The automated packaging station 16 also includes the turntable assembly 48, which is where the cassettes 162 are staged for use and then used to fill a plurality of blister packs 90. To this end, the turntable assembly 48 includes a rotary dial 164 including a plurality of nests 166 for receiving blister packs 90. The blister packs 90 are loaded onto the rotary dial 164 by a plurality of packaging magazines 168. The packaging magazines 168 extend at least partially through the barrier wall 150 into the operator work zone 154 such that operators 156 can reload the packaging magazines 168 with additional stacks of blister packs 90 as needed. The turntable assembly 48 also includes a feeder base 170 located downstream from the packaging magazines 168 and located above the rotary dial 164 at a position for filling the blister packs 90, a loading staging table 172 located adjacent the rotary dial 164 and configured to receive cassettes 162 before use at the feeder base 170, and an unloading staging table 174 located adjacent the rotary dial 164 and configured to receive cassettes 162 after use at the feeder base 170.

The automated packaging station 16 also includes the first robot 44 located between the storage carousels 160 and the turntable assembly 48, the first robot 44 being operable to move up to eight cassettes 162 at once and to move cassettes 162 between the storage carousels 160, the staging tables 172, 174, and the feeder base 170 as required. The first robot 44 is also operable to move any cassette 162 requiring a refill of bulk stock to a refill window 176 at the operator work zone 154. The operators 156 manually take the cassette 162 out of the automated packaging station 16 for refill and then return the cassette 162 back to the refill window 176 for replacement to the storage carousels 160 by the first robot 44 after the cassette 162 has been refilled with bulk stock.

The turntable assembly 48 also includes a printer assembly 180 for automatically printing and applying the covers 96 onto the filled blister packs 90 after filling at the feeder base 170. Once the blister packs 90 are sealed with the covers 96, the turntable assembly 48 rotates the blister packs 90 into the working area of the second robot 46, which is generally located on an opposite side of the turntable assembly 48 from the first robot 44. The second robot 46 operates to remove the filled and sealed blister packs 90 from the turntable assembly 48 onto a blister unloading station 182. As shown in FIG. 4, the blister unloading station 182 includes two drawers 184 for holding trays 186 that receive the filled and sealed blister packs 90 moved by the second robot 46. While the second robot 46 moves blister packs 90 into one tray 186, the other tray 186 is capable of being removed by an operator 156 at the operator work zone 154 for movement to other verification and/or final packaging stations, such as where the blister packs 90 are placed into the cartons 120a, 120b, 120c, 120d and then shipped to the patient.

The operator work zone 154 located outside the barrier wall 150 includes access to the refill window 176, to the packaging magazines 168, and to the drawers 184 of the blister unloading station 182 as previously described. In addition, the operator work zone 154 includes a workstation 190 including the machine controller 42 and a user interface 192 for providing information on the working status of the elements within the robotic work zone 152. Specific details of these elements located in the robotic work zone 152 and the operator work zone 154 are explained in further detail below with reference to FIGS. 5 through 16.

In general operation, the first robot 44 retrieves and loads up to eight cassettes 162 needed for a particular pass time onto the feeder base 170 while the rotary dial 164 rotates in stepwise fashion and receives empty blister packs 90 from the packaging magazines 168 located before the feeder base 170. When each blister pack 90 is moved under the feeder base 170, selected cassettes 162 are simultaneously actuated to dispense a unit dose of one or more pills. These pills are guided by the feeder base 170 into the respective cavities on the blister pack 90. The filled blister packs 90 then continue to rotate around the rotary dial 164 past additional stations described in detail below until removal by the second robot 46. As the feeder base 170 operates to fill the set of blister packs 90 rotating around the rotary dial 164, the first robot 44 returns previously-used cassettes 162 from the unloading staging table 174 to the storage carousels 160 and retrieves new cassettes 162 for the next set of blister packs 90 to place those new cassettes 162 on the loading staging table 172. This simultaneous operation of the first robot 44, the second robot 46, and the turntable assembly 48 enables substantially uninterrupted operation of the automated packaging station 16, which improves the efficiency of the drug packaging system 10. The advantageous operation of the automated packaging station 16 and the control operations actuating that operation are described in further detail below.

Figure 5:
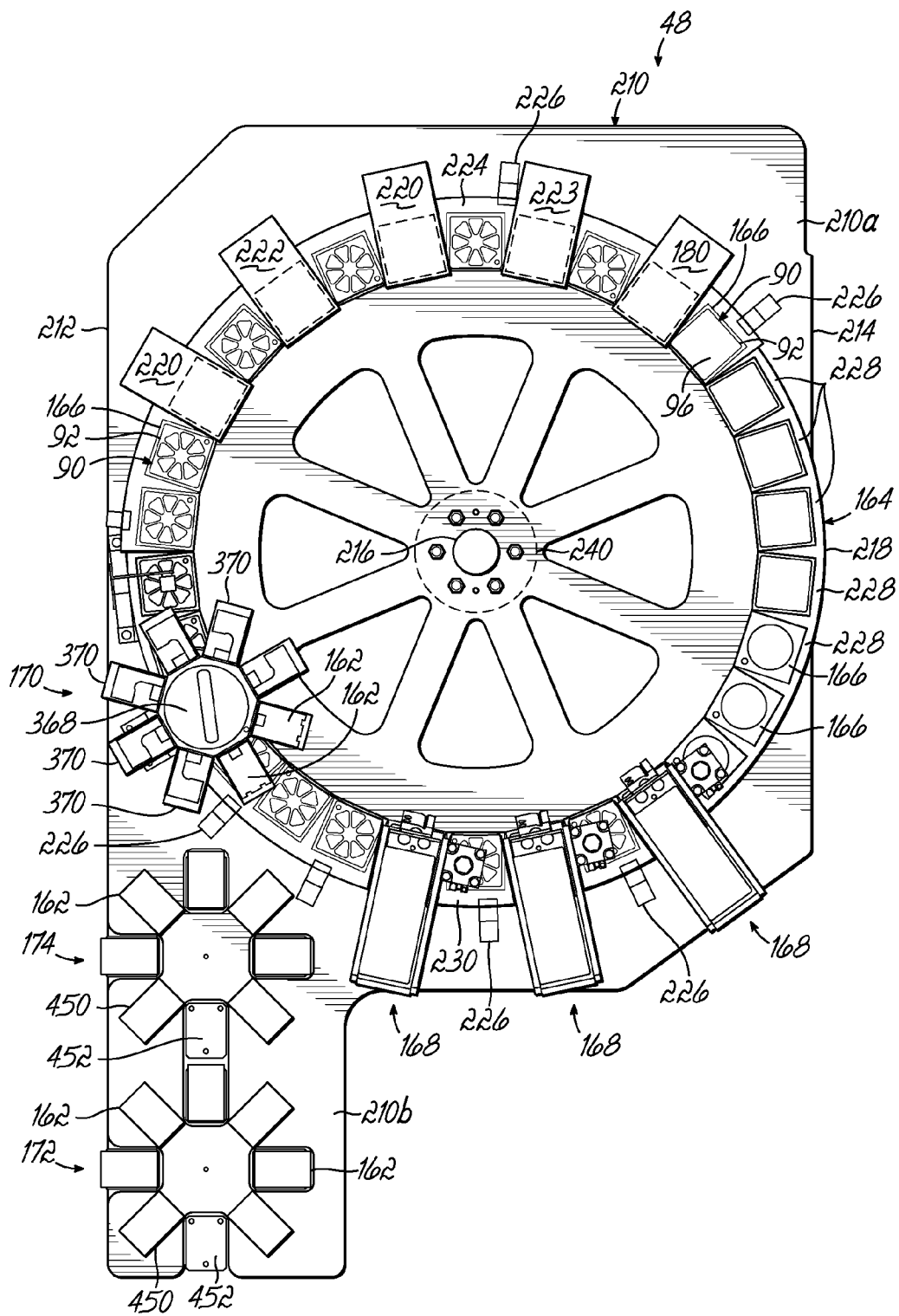
FIG. 5 is a top detailed view of a turntable assembly used with the automated packaging station of FIG. 4.

With reference to FIG. 5, the turntable assembly 48 is illustrated in detail. As described briefly above, the turntable assembly 48 is located in a centralized position within the robotic work zone 152 so that each of the operations applied to the blister packs 90 occurs at this turntable assembly 48. The turntable assembly 48 includes a turntable platform 210 having a generally rectangular portion 210a defining a first platform side 212 and a second platform side 214. The first platform side 212 is configured to face towards the first robot 44, while the second platform side 214 is located adjacent to the blister unloading station 182. The rotary dial 164 is mounted on the turntable platform 210 so as to cover a substantial portion of the rectangular portion 210a of the turntable platform 210. The turntable platform 210 also includes a projecting portion 210b that extends beyond the rectangular portion 210a at the first platform side 212 so as to provide additional space for the loading staging table 172 and the unloading staging table 174. Although the unloading staging table 174 is shown in the exemplary embodiment as being located between the loading staging table 172 and the rotary dial 164, it will be appreciated that the positions of the two staging tables 172, 174 may be reversed or modified in other embodiments without departing from the scope of the invention.

The rotary dial 164 includes a central shaft 216 about which the rotary dial 164 rotates during operation of the automated packaging station 16. The rotary dial 164 also defines an outer periphery 218 where the plurality of nests 166 configured to receive the blister packs 90 are mounted. The positions through which the rotary dial 164 rotates the nests 166 may be characterized as the positions on a clock, with the feeder base 170 located approximately at the 12 o'clock position. Using this understanding of relative positioning around the periphery 218 of the rotary dial 164, the blister packs 90 move from the feeder base 170 to a plurality of additional processing stations located near the 1 o'clock, 2 o'clock, 3 o'clock, and 4 o'clock positions. In the exemplary embodiment, these stations include a fill verification station 220 near the 1 o'clock position, an alternative loading mechanism 222 near the 2 o'clock position, another fill verification station 220 and a product verification station 223 near the 3 o'clock position, and the printer assembly 180 at the 4 o'clock position.

The fill verification station 220 includes a vision-based CCD camera (not shown) supplied commercially from the manufacturer of the first robot 44 (for example, from FANUC Robotics America Corporation of Rochester, Mich.). Using either black-and-white or color images from the CCD camera, the fill verification station 220 detects whether a unit dose has been placed into each compartment 94 of the blister pack 90 so that the machine controller 42 can detect inconsistencies with where unit doses are expected to be located within the blister pack 90. If such an inconsistency is detected, then the particular compartment 94 and blister pack 90 is flagged in the system for manual review after the blister pack 90 is removed from the automated packaging station 16. If the verification determines that the appropriate compartments 94 are filled with unit doses of medication, then these verification steps enable the automated packaging system 16 to fill blister packs 90 without necessitating manual review of these verified blister packs 90. In this regard, the verification process is largely automated, thereby significantly reducing the human operator hours required to fill a monthly order for each patient and also improving the overall quality and accuracy of the filling process.

The alternative loading mechanism 222 is illustrated in FIG. 5 as a black box near the 2 o'clock position, but the alternative loading mechanism 222 includes any alternative type of filling or loading structures operable to place unit doses of medication into compartments 94 of the blister packs 90. For example, some medications cannot be accurately dispensed from bulk stock in a cassette 162 because the medications are too fragile or too oddly-shaped for accurate dispensing from a cassette 162, and these medications must be inserted into the blister packs 90 by alternative mechanisms. Thus, the alternative loading mechanism 222 may include a third robot (not shown) such as a pick-and-place robot or similar equipment that operates to select one of these non-cassette dispensable medications and to place unit doses of such medications into the appropriate blister packs 90 as required. Similar to the first robot 44, it will be understood that such a third robot would also have access to a storage carousel or some other indexed storage device and a staging table for temporarily holding medication containers closer to the rotary dial 164 both before and after use at the alternative loading mechanism 222. The third robot operates to retrieve containers holding non-cassette dispensable medications, pick the medications needed from these containers, and individually place unit doses of these medications in the appropriate compartments 94. Thus, the alternative loading mechanism 222 operates much the same way as the primary loading mechanisms around the first robot 44, and the description of these similar elements used with the pick-and-place third robot has not been repeated herein for simplicity.

Similar to the feeder base 170, the alternative loading mechanism 222 may also be immediately followed on the rotary dial 164 by another fill verification station 220 near the 3 o'clock position for verifying whether compartments 94 that should have been filled at the alternative loading mechanism 222 were actually filled. It will be understood that the fill verification station 220 is identical to the one described above, and hence the same reference number has been used on both fill verification stations. In the exemplary embodiment shown, the verification of these fill verification stations 220 is also supplemented by the product verification station 223 also located near the 3 o'clock position. The product verification station 223 includes a laser spectroscopy system or a similar device for actually detecting physical attributes (e.g., color, shape, size) of the unit doses located in the compartments 94. To this end, the actual products in the compartments 94 may also be verified for an additional level of quality assurance shortly after filling the compartments 94 of the blister packs 90. It will be appreciated that more or fewer fill verification stations 220 and product verification stations 223 may be used on the rotary dial 164 in other embodiments of the invention.

The printer assembly 180 is also illustrated in black box form near the 4 o'clock position. The printer assembly 180 includes a conventional label-printing mechanism that operates to print the machine readable indicia 108 and the human readable labels 110 onto covers 96 and then apply those covers 96 (via heat sealing or adherence) to the appropriate blister pack 90. The covers 96 seal the unit doses of medication inside the blister packs 90 for secured downstream processing and delivery to the patient. It will be understood that the printer assembly 180 may operate to actively print covers 96 for blister packs 90 located one or more steps upstream from the printer assembly 180 such that the covers 96 are ready for application to the bodies 92 of the blister packs 90 immediately upon arrival of the blister packs 90 at the printer assembly 180. It will be understood that the printer assembly 180 and the other additional processing stations described above may be modified or repositioned around the periphery 218 of the rotary dial 164 as required in other embodiments consistent with the scope of the invention.

The printer assembly 180 effectively prints the information on the covers 96 in a serial, on-demand manner shortly before the appropriate blister pack 90 arrives at the printer assembly 180. As a result, the information printed on the covers 96 in the form of machine readable indicia 108 and human readable labels 110 may be modified depending on the result of various fill and product verification that occurs upstream of the printer assembly 180. In this regard, when a filling or product error is detected by the fill verification station(s) 220 or by the product verification station 223, the information printed on the cover 96 for that blister pack 90 may be modified to indicate the need for downstream manual inspection. For example, the human readable labels 110 may be replaced partially or entirely with a label that reads "INSPECTION REQUIRED" or some other similar wording readily susceptible to visual recognition, and the machine readable indicia 108 may be printed in incomplete format so that the downstream steps requiring a barcode scan or other indicia scan cannot be completed before the error is addressed. The specific information printed on the covers 96 therefore helps control what happens to each blister pack 90 following filling at the automated packaging station 16.

The turntable assembly 48 also includes an elongate cover 224 coupled to the turntable platform 210 with one or more mounting brackets 226 and configured to cover the blister packs 90 between the feeder base 170 at the 12 o'clock position to unloading positions 228 located adjacent to the blister unloading station 182 located at about the 5 o'clock to 7 o'clock position on the rotary dial 164. The elongate cover 224 may include apertures (not shown) at the additional processing stations (e.g., the fill verification station 220, the alternative loading mechanism 222, and the printer assembly 180) to enable those processing stations to operate as described above on the blister packs 90. However, the elongate cover 224 operates to protect the filled blister packs 90 from outside interference and/or contamination during the course of travel between the feeder base 170 and the unloading positions 228. It will be understood that the positioning and size of the elongate cover 224 may be modified in other embodiments without departing from the current invention.

The plurality of packaging magazines 168 may be located on the turntable platform 210 at any location between the unloading positions 228 and the feeder base 170. In the exemplary embodiment, for example, three packaging magazines 168 are located in the 8 o'clock to 10 o'clock segment of the rotary dial 164 using the clock reference described above. Each of the packaging magazines 168 is configured to fill an empty nest 166 on the rotary dial 164 with a blister pack 90 as the empty nests 166 move past the packaging magazines 168. Multiple packaging magazines 168 are provided such that each packaging magazine 168 only needs to load a blister pack 90, on average, on every third nest 166 that passes by the packaging magazine 168 rather than onto every empty nest 166. This configuration enables the automated packaging station 16, as a whole, to operate more quickly because the packaging magazines 168 provide redundancy and extra capacity to load blister packs 90 onto the rotary dial 164. More specifically, the operational speed of the packaging magazines 168 does not limit the functional speed with which the automated packaging station 16 fills the blister packs 90. Furthermore, a defective or empty packaging magazine 168 will not adversely affect the functional speed with this configuration. The nests 166 loaded with empty blister packs 90 then rotate back to the feeder base 170 at the 12 o'clock position, and the cycle begins anew. Further details of the packaging magazines 168 are provided with reference to FIGS. 8A through 8F below.

Optionally, an additional elongate cover 230 may be positioned at least between the feeder base 170 and the packaging magazines 168 as shown in the exemplary embodiment of FIG. 5. This elongate cover 230 is also coupled to the turntable platform 210 with mounting brackets 226 and serves a similar function as the first elongate cover 224, to stop interference or contamination of empty blister packs 90 before the blister packs 90 are filled at the feeder base 170. The feeder base 170 is located above one position (the 12 o'clock position) on the rotary dial 164 and operates one or more of the cassettes 162 simultaneously to dispense unit doses from each desired cassette 162 into the blister pack 90 located at the feeder base 170. The specific operation and elements of the feeder base 170 are described with reference to FIGS. 9A through 9D below. The loading staging table 172 and unloading staging table 174 are disposed in close proximity to the feeder base 170 such that the first robot 44 can quickly move up to eight cassettes 162 between these elements on the turntable assembly 48. Further details of the operation and elements of the two staging tables 172, 174 are provided with reference to FIGS. 10A through 10D below.

Figure 6:
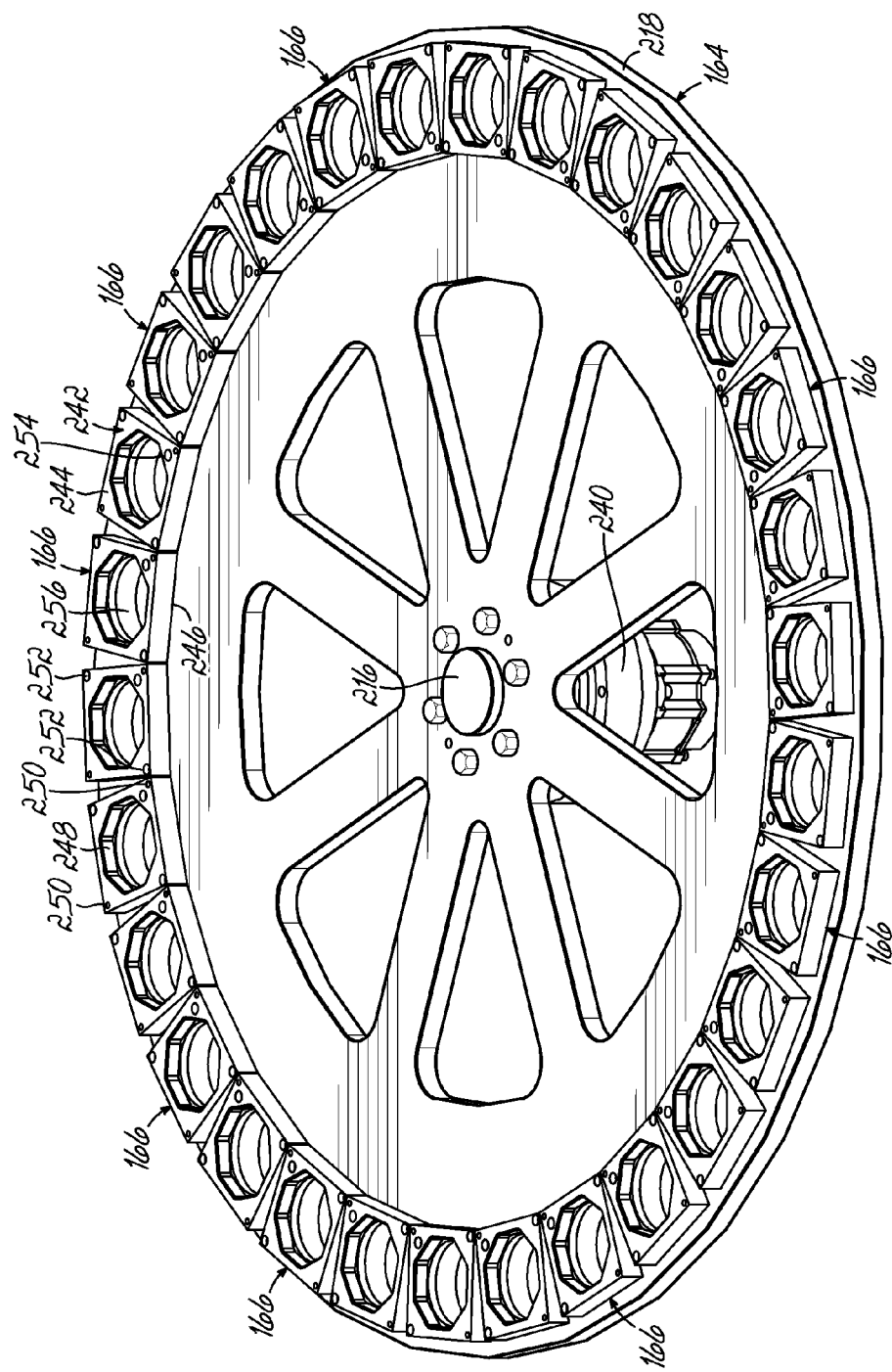
FIG. 6 is a perspective view of a rotary dial of the turntable assembly of FIG. 5, the rotary dial carrying a plurality of nests configured to receive medication packagings.
Figure 7:
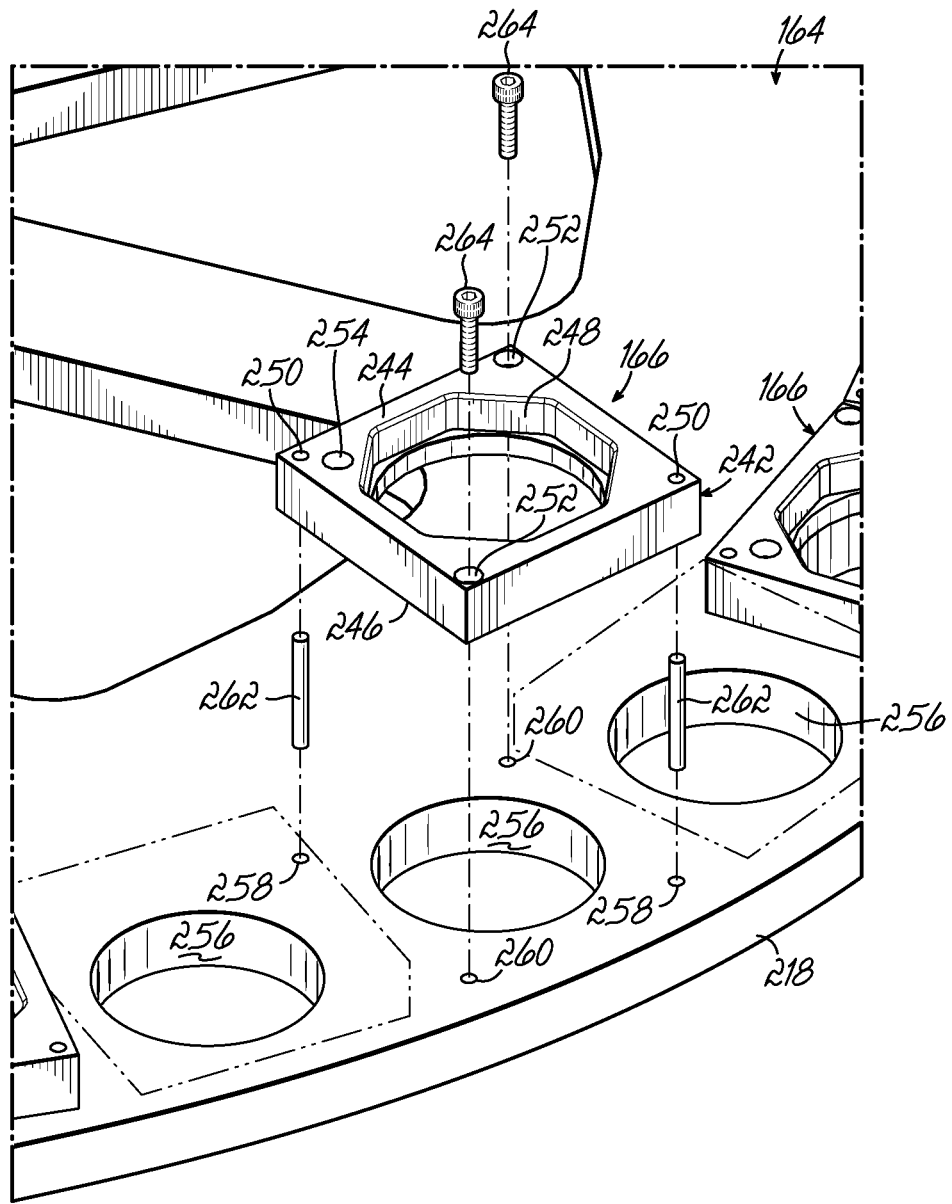
FIG. 7 is a partially exploded perspective view of the rotary dial and one of the nests of FIG. 6, showing the coupling between the nest and the rotary dial.

Turning to FIGS. 6 and 7, the rotary dial 164 of the turntable assembly 48 is shown. As previously described, the rotary dial 164 includes a plurality of nests 166 configured to receive blister packs 90 located along the entire outer periphery 218 of the rotary dial 164. In the exemplary embodiment, the rotary dial 164 carries thirty nests 166, although the rotary dial 164 may be resized to accommodate more or fewer nests 166 in other embodiments of the invention. The central shaft 216 of the rotary dial 164 is connected to a motor 240 located below the turntable platform 210 (not shown in FIG. 6). The motor 240 is operative to rotate the rotary dial 164 in a set, stepwise fashion through entire revolutions of the rotary dial 164. To this end, in the exemplary embodiment with thirty nests 166 coupled to the rotary dial 164, the motor 240 operates to move the rotary dial 164 through $\frac{1}{30}^{th}$ of a complete revolution each time the motor 240 moves the rotary dial 164. This stepwise rotation ensures that the nests 166 and the corresponding blister packs 90 always properly align with the feeder base 170 and the other elements of the turntable assembly 48 described above.

One of the nests 166 is shown exploded from the rotary dial 164 in FIG. 7 to illustrate how the nests 166 are aligned and coupled to the rotary dial 164. To this end, the nest 166 is defined by a generally square-shaped plate 242 having a top surface 244 configured to face a blister pack 90, a bottom surface 246 configured to abut the rotary dial 164, and a shaped aperture 248 extending through the plate 242 from the top surface 244 to the bottom surface 246. The shaped aperture 248 may be formed partially octagonal and partially circular to accommodate the octagonal pie-shaped structure of the compartments 94 extending downwardly from the top surface 98 of the blister pack 90. It will be understood that the plate 242 and the aperture 248 may be resized or reshaped in other embodiments to match other blister packs 90 without departing from the scope of the embodiments of the invention.

The nest 166 also includes a pair of guide pin apertures 250 located on two opposing corners of the square-shaped plate 242 and a pair of bolt apertures 252 located on the other opposing corners of the square-shaped plate 242. The guide pin apertures 250 and bolt apertures 252 extend from the top surface 244 to the bottom surface 246 and are spaced slightly inwardly from the corners of the plate 242. The apertures 250, 252 are used during assembly of the nest 166 to the rotary dial 164 as described below. The top surface 244 of the nest 166 also includes an indexing slot 254 located adjacent one of the corners with the guide pin apertures 250. The indexing slot 254 is configured to receive the indexing feature 106 projecting downwardly from the top surface 98 of the blister pack 90 when the blister pack 90 is held by the nest 166, thereby ensuring uniform and consistent orientation of each blister pack 90 placed into each nest 166 on the rotary dial 164. Consequently, when a blister pack 90 is positioned in a nest 166 on the rotary dial 164, the top surface 98 of the blister pack abuts the top surface 244 of the nest 166 while the indexing features 106 and the compartments 94 extend into the indexing slot 254 and the shaped aperture 248, respectively.

As shown most clearly in FIG. 7, the rotary dial 164 includes a series of round apertures 256 adjacent to the outer periphery 218 that are configured to be aligned with the shaped aperture 248 of the nest 166. The round aperture 256 and the shaped aperture 248 collectively extend through the combined thickness of the nest 166 and rotary dial 164 such that any inadvertently dropped medications or other interfering elements into the nest 166 drop through the rotary dial 164 without interfering with the placement of another blister pack 90 into that nest 166. Each of the round apertures 256 on the rotary dial 164 is surrounded by two guide pin receptacles 258 and two bolt receptacles 260 oriented in the same configuration (opposing corners) as the guide pin apertures 250 and bolt apertures 252 on the nest 166. As such, two guide pins 262 are positioned in each guide pin receptacle 258 and then the nest 166 is moved downwardly towards the rotary dial 164 from the position shown in FIG. 7 until the guide pins 262 are located within the guide pin apertures 250 on the nest 166. Two threaded bolts 264 or analogous connecting fasteners are then inserted through the bolt apertures 252 on the nest 166 so as to be threadably engaged with the bolt receptacles 260 formed in the rotary dial 164. The threaded bolts 264 are tightened to retain the nest 166 in abutting relation on top of the rotary dial 164. Thus, the coupling of each nest 166 to the rotary dial 164 is conducted in a consistent and repeatable manner by simply following the above-described process to align and affix the nest 166 to the rotary dial 164.

With reference to FIGS. 8A through 8F, one of the packaging magazines 168 previously described is shown in further detail. The packaging magazine 168 is configured to position empty blister packs 90 on the nests 166 of the turntable assembly 48 during operation of the automated packaging station 16. The packaging magazine 168 includes a housing 270 including first and second sidewalls 272, 274 that are generally oriented vertically and parallel to one another. The first and second sidewalls 272, 274 define a lower housing portion 276 configured to be supported by the turntable platform 210 and an upper housing portion 278. The housing 270 also includes a front barrier wall 280 coupled to and extending between the first and second sidewalls 272, 274 at the lower housing portion 276. The front barrier wall 280 is oriented generally vertically so as to be transverse to the outer periphery 218 of the rotary dial 164. The front barrier wall 280 faces towards the rotary dial 164 (see FIG. 8B) such that even though the housing 270 extends partially through the barrier wall 150 into the operator work zone 154 as shown in FIG. 4, the operators 156 and other interfering objects from outside the robotic work zone 152 cannot interfere with the rotary dial 164 by passing through the packaging magazine 168.

Figure 8A:
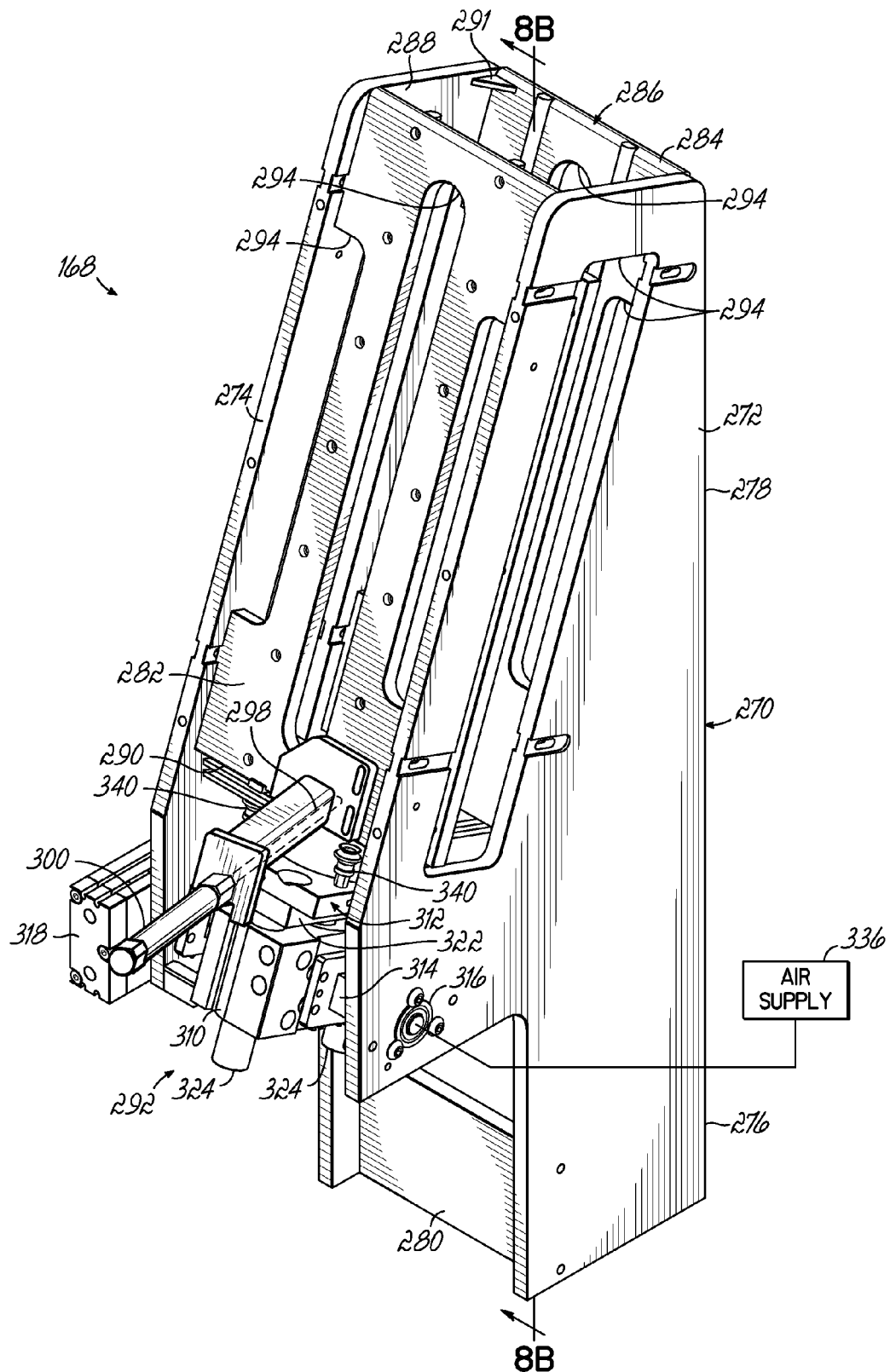
FIG. 8A is a perspective view of a packaging magazine operable to position empty medication packagings of FIG. 2A onto the nests of the turntable assembly of FIG. 5.
Figure 8B:
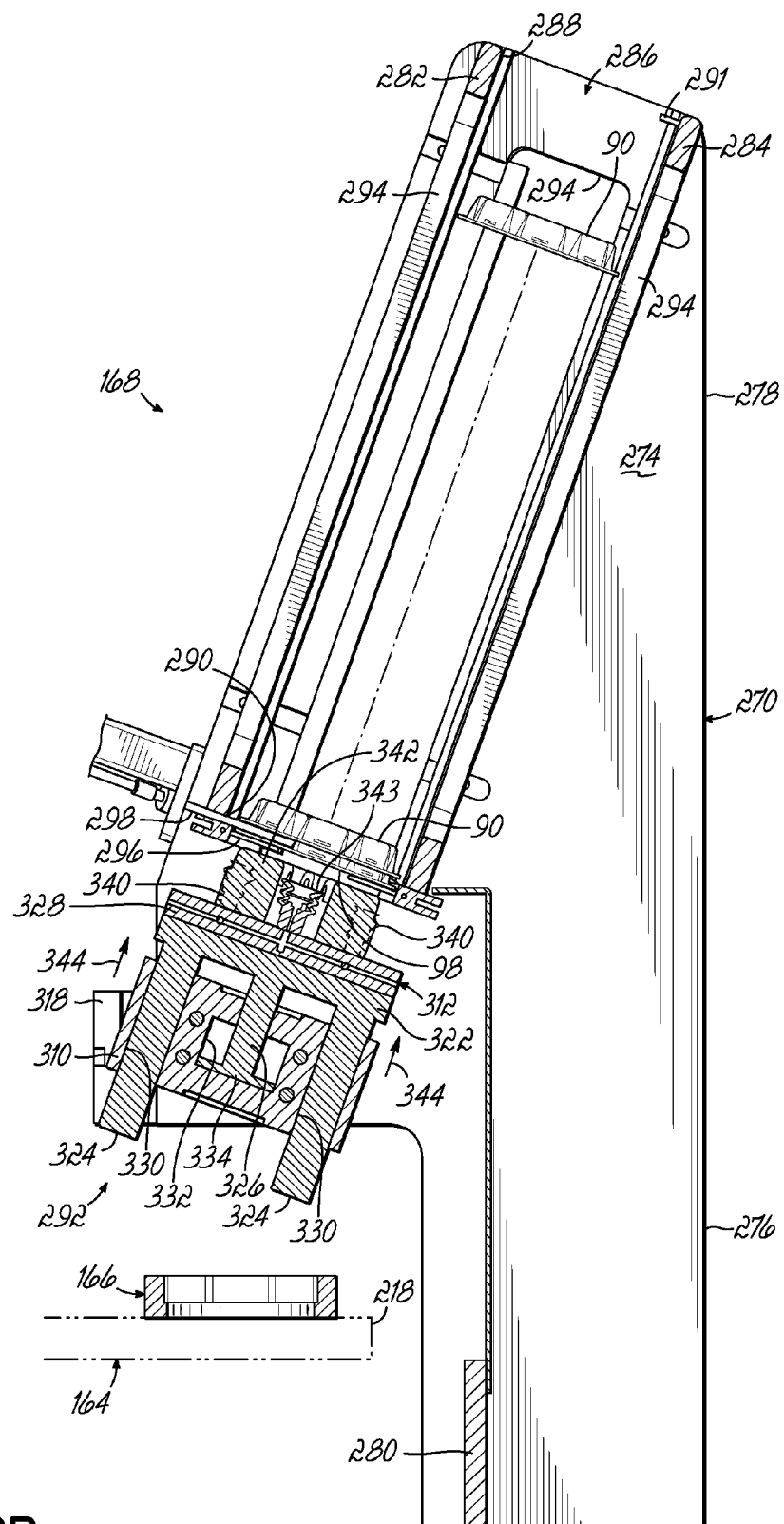
FIG. 8B is a cross-sectional side view of the packaging magazine of FIG. 8A, with a placement head located in a first position.

The housing 270 also includes a front channel wall 282 and a rear channel wall 284 located at the upper housing portion 278 and extending in generally parallel relation to one another between the first and second sidewalls 272, 274. The upper housing portion 278 therefore defines an elongate magazine channel 286 bounded by the first and second sidewalls 272, 274 and the front and rear channel walls 282, 284. The magazine channel 286 is sized with a generally square shaped cross-section such that a stack of empty blister packs 90 may be received within the magazine channel 286. Each of the front and rear channel walls 282, 284 is angled from a vertical orientation such that the magazine channel 286 is angled slightly forward towards the rotary dial 164. In this regard, the magazine channel 286 defines an open upper channel end 288 extending into the operator work zone 154 and a lower channel end 290 projecting beyond the front barrier wall 280 to be located at least partially above the rotary dial 164. With reference to FIGS. 8A and 8B, the upper channel end 288 includes an angled projection 291 extending inwardly from one corner of the upper channel end 288 and sized to receive the notch 107 on each empty blister pack 90 as the blister packs 90 are loaded into the magazine channel 286. The angled projection 291 blocks any other corner of the blister packs 90 from readily passing into the magazine channel 286 and helps ensure a consistent and proper orientation of each blister pack 90 within the packaging magazine 168.

As shown in FIGS. 8A and 8B, the first and second sidewalls 272, 274 of the housing 270 also project forward at the upper housing portion 278 beyond the front barrier wall 280 of the lower housing portion 276 to accommodate the lower channel end 290 and a blister gripping head assembly 292 located below the lower channel end 290 and described in further detail below. To this end, each of the first and second sidewalls 272, 274 define a shape approximate to half an arrowhead pointed upwardly when viewed from the side as shown in FIG. 8B. In operation, a stack of empty blister packs 90 may be inserted through the upper channel end 288 and gravity fed to the lower channel end 290. At this location, the blister packs 90 are moved by the blister gripping head assembly 292 individually from the packaging magazine 168 to the nest 166 on the rotary dial 164. This movement process is described in further detail below.

With continued reference to FIG. 8A, each of the first and second sidewalls 272, 274 and the front and rear channel walls 282, 284 include one or more elongate apertures 294 along the length of the walls 272, 274, 282, 284 to reduce the amount of material required to form the packaging magazine 168. In addition, these elongate apertures 294 enable an operator 156 to monitor the stacks of blister packs 90 within the magazine channel 286 to better know when the packaging magazine 168 will need to be refilled with more empty blister packs 90. Moreover, the elongate apertures 294 provide access to the inside of the magazine channel 286 to remove any blockages or occlusions that stop blister packs 90 in the stack from being gravity fed to the lower channel end 290. More or fewer of the elongate apertures 294 may be provided in other embodiments consistent with the scope of the invention. Furthermore, it will be understood that the particular cross-sectional shape and size and the angling of the magazine channel 286 may be modified for other blister packs 90 without departing from the scope of the embodiments of the invention.

Figure 8C:
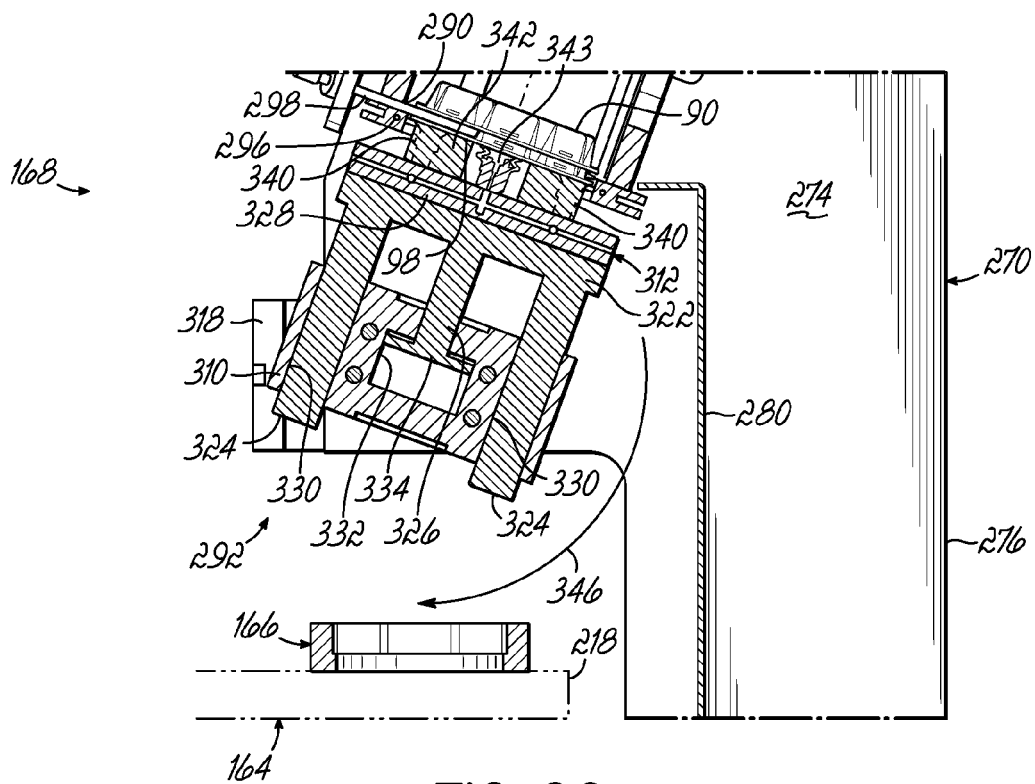
FIG. 8C is a cross-sectional side view of the packaging magazine of FIG. 8B, with the placement head retrieving a new medication packaging in the first position from a stack of medication packagings.
Figure 8D:
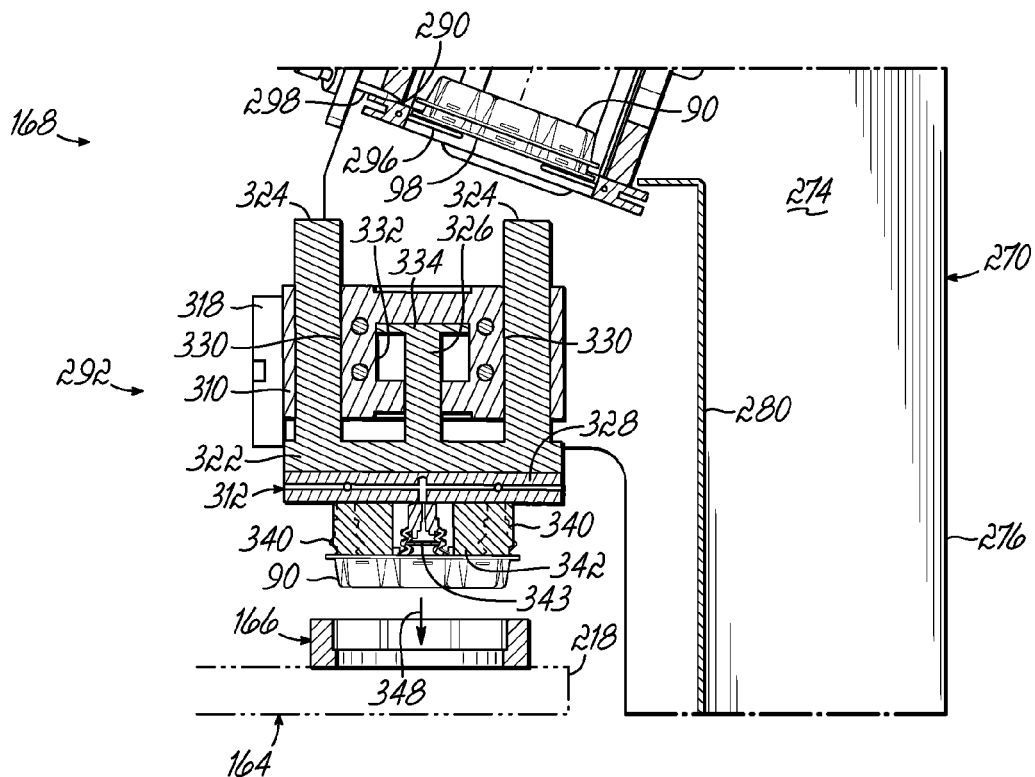
FIG. 8D is a cross-sectional side view of the packaging magazine of FIG. 8C, with the placement head rotated to a second position above one of the nests.
Figure 8E:
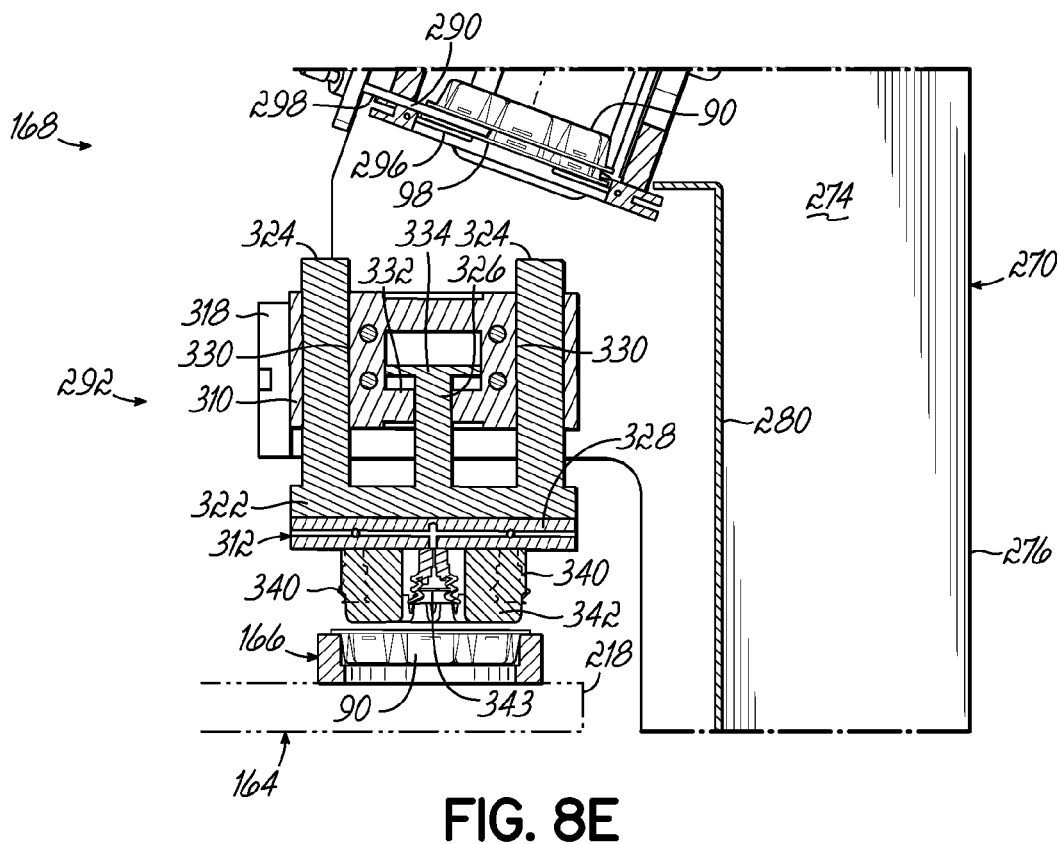
FIG. 8E is a cross-sectional side view of the packaging magazine of FIG. 8D, with the placement head releasing the medication packaging into the nest.

Turning to FIGS. 8B and 8C, the lower channel end 290 includes additional elements to reliably retain and release one blister pack 90 at a time from the stack of blister packs 90 held within the magazine channel 286. More particularly, the lower channel end 290 includes a retention ring 296 in the form of a generally O-shaped ring located at the lower channel end 290. The retention ring 296 of the exemplary embodiment is rigidly coupled by adherence or some other known method to the first and second sidewalls 272, 274 and to the front and rear channel walls 282, 284 except at the corners of the lower channel end 290, where the retention ring 296 projects outwardly into the path of the blister packs 90. As a result of this positioning of the retention ring 296, the retention ring 296 blocks a lowermost blister pack 90 within the stack of blister packs 90 from dropping out of the magazine channel 286. The blister pack 90 is formed with adequate resiliency at the corner regions 104 such that the corner regions 104 may elastically deform to enable the lowermost blister pack 90 to be pulled through the lower channel end 290 by the blister gripping head assembly 292. However, the corner regions 104 are not so resilient or flimsy as to be forced through the retention ring 296 by only the weight of the stack of blister packs 90 above the lowermost blister pack 90. The blister pack 90 returns to the original shape immediately after passing through the retention ring 296. The stationary retention ring 296 immediately blocks the next blister pack 90 (falling with gravity) from unintentionally dropping out of the lower channel end 290 when the lowermost blister pack 90 is removed. It will be understood that the retention ring 296 may be replaced or modified in other embodiments of the invention with alternative structure that selectively blocks the lowermost blister pack 90 at the lower channel end 290. For example, active blocking members (not shown) may be provided that are actuated to pivot out of the way of the lowermost blister pack 90 and then back into a blocking position, for example.

Also shown in FIGS. 8B and 8C, the lower channel end 290 includes an alignment pin 298 that is located at the front channel wall 282 and immediately above the retention ring 296. When the stack of blister packs 90 is located within the magazine channel 286, the lowermost blister pack 90 does not completely nest within the next blister pack 90 in the stack. In this regard, the compartments 94 of the lowermost blister pack 90 only nest partially within the compartments 94 of the next blister pack 90, and the top surfaces 98 of these blister packs 90 are spaced from one another as shown. The alignment pin 298 is sized to fit within this gap between the top surfaces 98 of the lowermost blister pack 90 and the next blister pack 90 in the stack. The alignment pin 298 is also shaped to snugly fit between two of the compartments 94 of the lowermost blister pack 90 when in an extended position as shown in FIG. 8B. Thus, in operation, the alignment pin 298 is inserted into the magazine channel 286 in the extended position to ensure that the lowermost blister pack 90 is exactly aligned for mating with structure on the blister gripping head assembly 292. The blister gripping head assembly 292 therefore receives the blister packs 90 in a consistent orientation and position, and can then place the blister packs 90 into the nests 166 with desired accuracy in positioning and orientation.

Furthermore, the alignment pin 298 also serves as a backstop holding the lowermost blister pack 90 in position to ensure that the gripping head assembly 292 obtains a solid grip on the blister pack 90 rather than pushing the blister pack 90 inwardly into the magazine channel 286. In this regard, the lowermost blister pack 90 is sufficiently captured between the retention ring 296 and the alignment pin 298. The alignment pin 298 is coupled to a piston 300 that is actuated by an actuator (not shown) such as a motor or a pneumatic solenoid that operates to move the piston 300 and thereby withdraw the alignment pin 298 when the stack of blister packs 90 needs to drop to position another lowermost blister pack 90 adjacent to the lower channel end 290. It will be understood that the alignment pin 298 may be repositioned, modified in size, and/or omitted in other embodiments of the invention. It will also be understood that the alignment pin 298 may be spring biased or otherwise biased towards the extended position in some embodiments. The retention ring 296 and the alignment pin 298 are shown in better detail apart from the lower channel end in FIG. 8F, which also shows additional aspects of the gripping head assembly 292 described in further detail below.

Figure 8F:
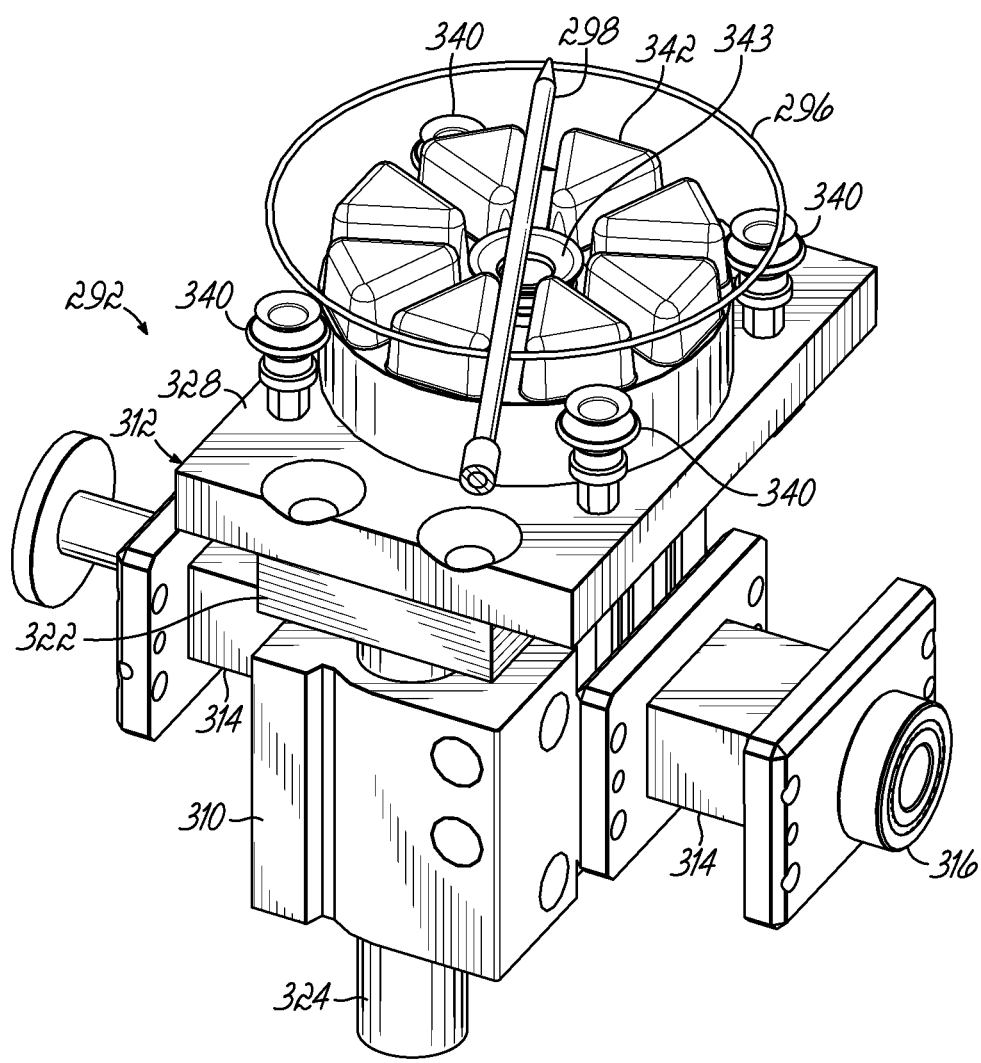
FIG. 8F is a perspective view of the placement head of the packaging magazine of FIG. 8B, with a retention ring and an alignment pin shown in further detail as well.

As briefly described above, the packaging magazine 168 includes the blister gripping head assembly 292, which operates to move one of the blister packs 90 in the magazine channel 286 from the lower channel end 290 to a nest 166 on the rotary dial 164 located beneath the blister gripping head assembly 292. With reference to FIGS. 8A, 8B, and 8F, the blister head gripping assembly 292 includes a rotatable base 310 and a gripping head 312 coupled to the rotatable base 310. The rotatable base 310 is a block-like member including opposed mounting axles 314 extending into pivotal engagement with sockets 316 located on the first and second sidewalls 272, 274 of the housing 270. An actuator 318 such as a pneumatic actuator is coupled to the second sidewall 274 adjacent the socket 316 as shown in FIG. 8A. This actuator 318 operates to rotate the gripping head assembly 292 by turning one of the mounting axles 314 of the rotatable base 310. It will be appreciated that any type of known actuator 318 operable to rotate a shaft may be used to rotate the gripping head assembly 292 in embodiments of the invention. As described in further detail below, the actuator 318 rotates the rotatable base 310 between a loading position (FIGS. 8B and 8C) in which the gripping head 312 faces towards the magazine channel 286 and an unloading position (FIGS. 8D and 8E) in which the gripping head 312 faces towards the nest 166.

The gripping head 312 includes a primary platform 322, a pair of guide rods 324 extending from the primary platform 322 towards the rotatable base 310, and a piston rod 326 located between the guide rods 324 and extending from the primary platform 322 towards the rotatable base 310. The gripping head 312 also includes an air cap 328 mounted on the opposite side of the primary platform 322 from the guide rods 324 and the piston rod 326 (e.g., facing away from the rotatable base 310). The air cap 328 includes additional structure described in detail below for selectively grabbing and retaining one of the blister packs 90. As shown most clearly in FIG. 8B, each of the guide rods 324 extends completely through a corresponding pair of through bores 330 formed in the rotatable base 310. The piston rod 326 extends into a piston chamber 332 formed in the interior of the rotatable base 310. More specifically, the piston rod 326 terminates in a piston head 334 slideably mounted within the piston chamber 332. The piston chamber 332 delimits the movement of the piston head 334 and therefore the movement of the gripping head 312 between an extended position shown in FIGS. 8C and 8E and a retracted position shown in FIGS. 8B and 8D. Thus, the gripping head 312 is capable of moving towards and away from the lower channel end 290 and towards and away from the nest 166 on the rotary dial 164. The guide rods 324 maintain the alignment of the gripping head 312 with the rotatable base 310 by sliding within the through bores 330 as the gripping head 312 moves between the extended and retracted positions.

This movement is actuated, in the exemplary embodiment, by applying a force to the piston head 334 to move the piston head 334 within the piston chamber 332 between the two positions. In one example, pressurized air is provided to the blister gripping head assembly 292 from an external air supply 336 as schematically shown in FIG. 8A. The rotatable base 310 may include valves (not shown) to control flow of pressurized air from the air supply 336 into the piston chamber 332 to pneumatically move the gripping head 312. Alternatively, other actuating forces applied by other known actuators (electrical motors, for example) and/or the force of gravity may be used alone or in combination with the pneumatic actuation to move the gripping head 312 in other embodiments consistent with the scope of the current invention. It will also be understood that the piston head 334 may be biased by a spring or the like to one of the extended or retracted positions, and preferably to the retracted position shown in FIG. 8B.

The external air supply 336 may also be connected to the air cap 328, which operates to selectively grip a blister pack 90 with negative air pressure (e.g., vacuum force). To this end, the air cap 328 includes four corner suction ports 340 extending outwardly from the air cap 328 to extend towards a blister pack 90 as shown in FIG. 8F. It will be understood that the air cap 328 may include valves (not shown) or other controls for generating the negative air pressure using the pressurized air from the external air supply 336 in a known manner. The four corner suction ports 340 are positioned so as to be aligned with the corner regions 104 of the top surface 98 of a blister pack 90. A mating structure 342 also extends in the same direction as the four corner suction ports 340 from the air cap 328. The mating structure 342 is shaped at least partially as a reverse mold to the compartments 94 of a blister pack 90. In the exemplary embodiment, and as shown in FIG. 8F, the mating structure 342 includes 8 wedge-shaped projections extending slightly beyond the four corner suction ports 340 in the center of the four corner suction ports 340. Consequently, when negative air pressure is applied to the four corner suction ports 340 to draw the top surface 98 of a blister pack 90 into engagement with the suction ports 340, the mating structure 342 becomes inserted at least partially into the corresponding compartments 94 of the blister pack 90 to maintain the desired orientation and positioning of the blister pack 90. Thus, the vacuum forces applied by the air cap at the four corner suction ports 340 do not cause the blister pack 90 to move laterally with respect to the gripping head 312, but instead, just towards and away from the primary platform 322 of the gripping head 312. The air cap 328 also includes a central suction port 343 located in the center of the mating structure 342 and configured to provide a suction grip on the central region 102 of the blister pack 90. The central suction port 343 is sized differently than the four corner suction ports 340 but operates in the same way as the four corner suction ports 340 to assist with gripping the blister pack 90.

The operation of the blister gripping head assembly 292 is shown in detail in the series of operational states shown in FIGS. 8B through 8E. To this end, the blister gripping head assembly 292 begins in the position shown in FIG. 8B, with the rotatable base 310 rotated to the loading position and the gripping head 312 located in the retracted position. The piston head 334 is then actuated to move the gripping head 312 as shown by arrows 344 in FIG. 8B to the extended position of FIG. 8C. Simultaneously, the vacuum pressure is applied at the four corner suction ports 340 and at the central suction port 343 to draw the lowermost blister pack 90 in the magazine channel 286 into rigid engagement with the air cap 328 (specifically into engagement with the suction ports 340, 343 and the mating structure 342). The gripping head 312 is then allowed to retract back towards the retracted position while the air cap 328 continues to apply suction force to retain the blister pack 90 on the gripping head 312. This retraction forces the lowermost blister pack 90 past the retention ring 296 as previously described and out of the lower channel end 290 of the magazine channel 286.

Meanwhile, the rotary dial 164 has rotated an empty nest 166 below the blister gripping head assembly 292 by the stepwise movements previously described in detail. The actuator 318 then rotates the rotatable base 310 as shown by arrow 346 in FIG. 8C to the unloading position shown in FIG. 8D while the vacuum force continues to be applied to retain the blister pack 90 at the air cap 328. In this position, the blister pack 90 is located above the nest 166 in the same desired orientation as the nest 166 (e.g., the indexing feature 106 of the blister pack 90 is located directly above the indexing slot 254 of the nest 166). The piston head 334 is then actuated to move the gripping head 312 as shown by arrows 348 in FIG. 8D to the extended position of FIG. 8E. Simultaneously, the vacuum pressure is turned off at the suction ports 340, 343 to release the blister pack 90 to be positioned into the nest 166. Because the alignment pin 298 in the housing 270 and the mating structure 342 on the blister gripping head assembly 292 maintained the desired orientation and position of the blister pack 90, the blister pack 90 is properly positioned to mate with the nest 166 as described in detail above. The blister pack 90 and nest 166 are then ready to be rotated by the rotary dial 164 away from the packaging magazine 168 and to the feeder base 170 for filling, as described with reference to FIGS. 9A through 9D below. The gripping head 312 is then withdrawn back to the retracted position and the blister gripping head assembly 292 is then rotated back to the loading position to return the blister gripping head assembly back to the original state of FIG. 8B. The process above then repeats itself for the next lowermost blister pack 90 in the magazine channel 286, which will have dropped to the lower channel end 290 during the previously-described operation of the blister gripping head assembly 292. In summary, each of the packaging magazines 168 is operable to place empty blister packs 90 from a stack of blister packs 90 into position on the nests 166 of the rotary dial 164 for filling and downstream processing, and the three packaging magazines 168 work in conjunction so that the automated packaging station 16 may continuously fill orders at a high efficiency.

Figure 9D:
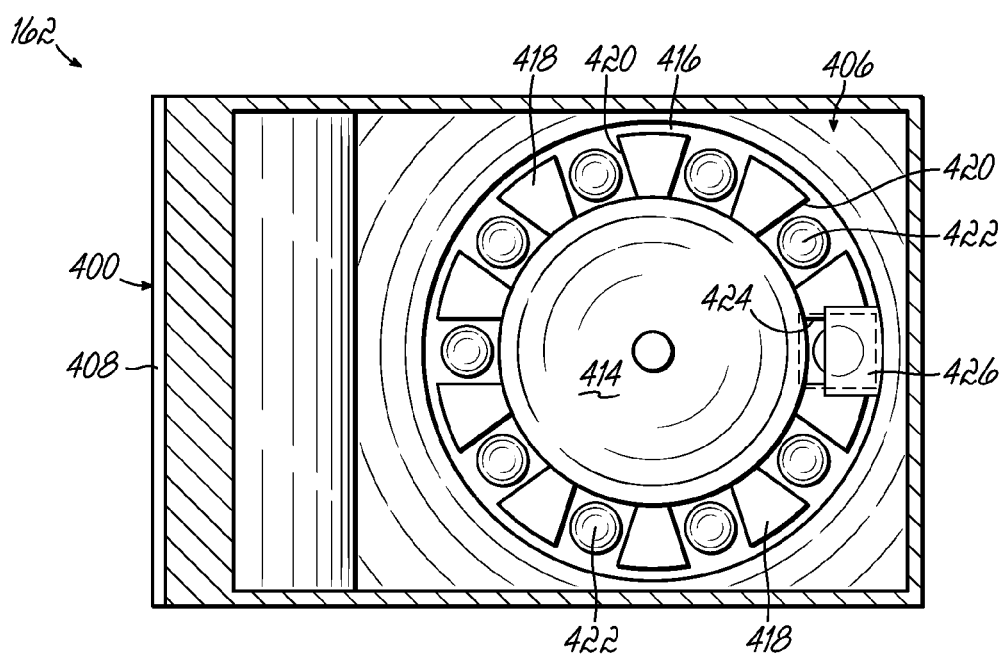
FIG. 9D is a cross-sectional top view of one of the cassettes used with the feeder base of FIG. 9C.
Figure 9A:
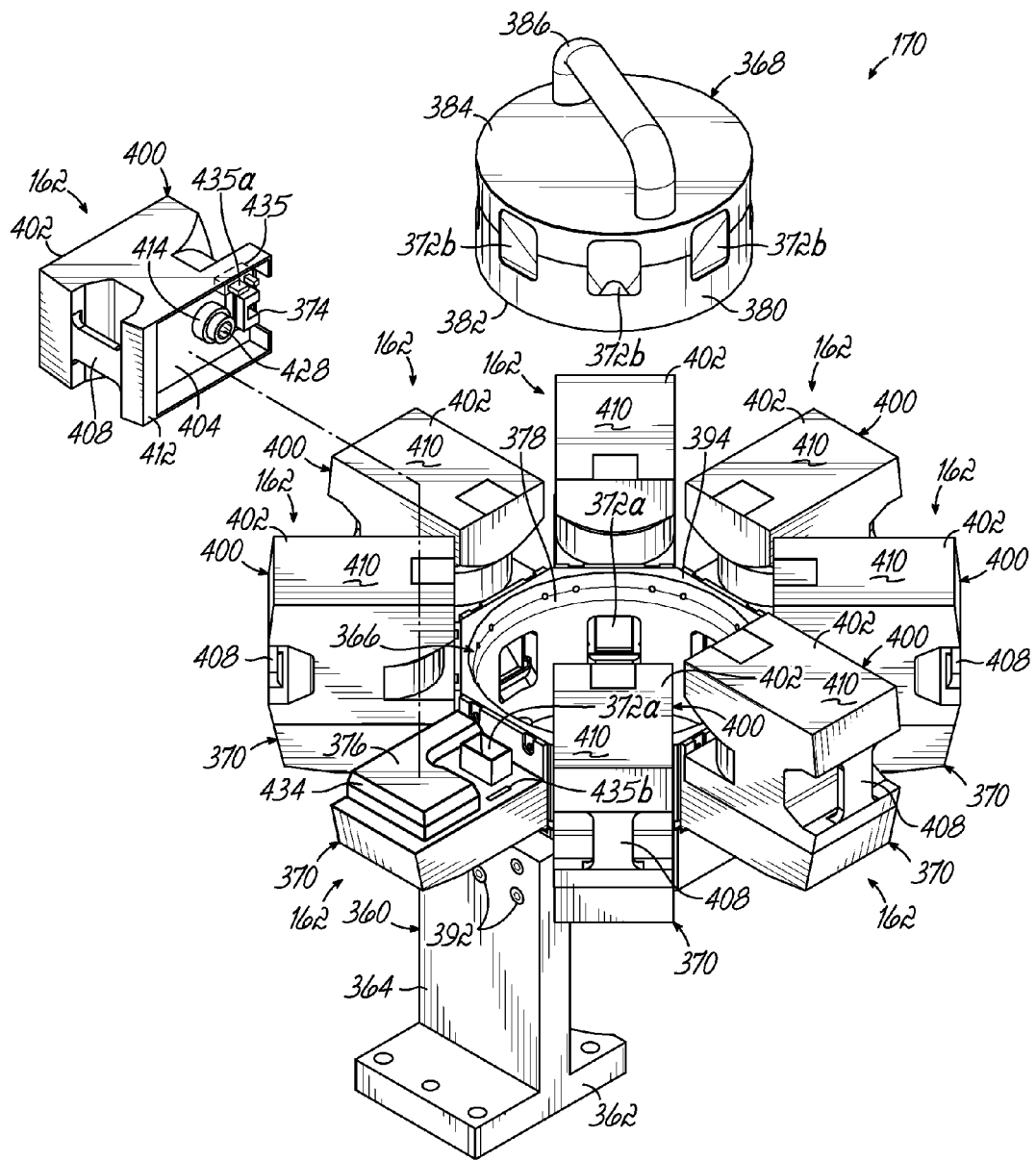
FIG. 9A is a partially exploded perspective view of a feeder base used as the primary filling location for medication packagings rotating along the turntable assembly of FIG. 5, the feeder base holding a plurality of pill dispensing cassettes.
Figure 9B:
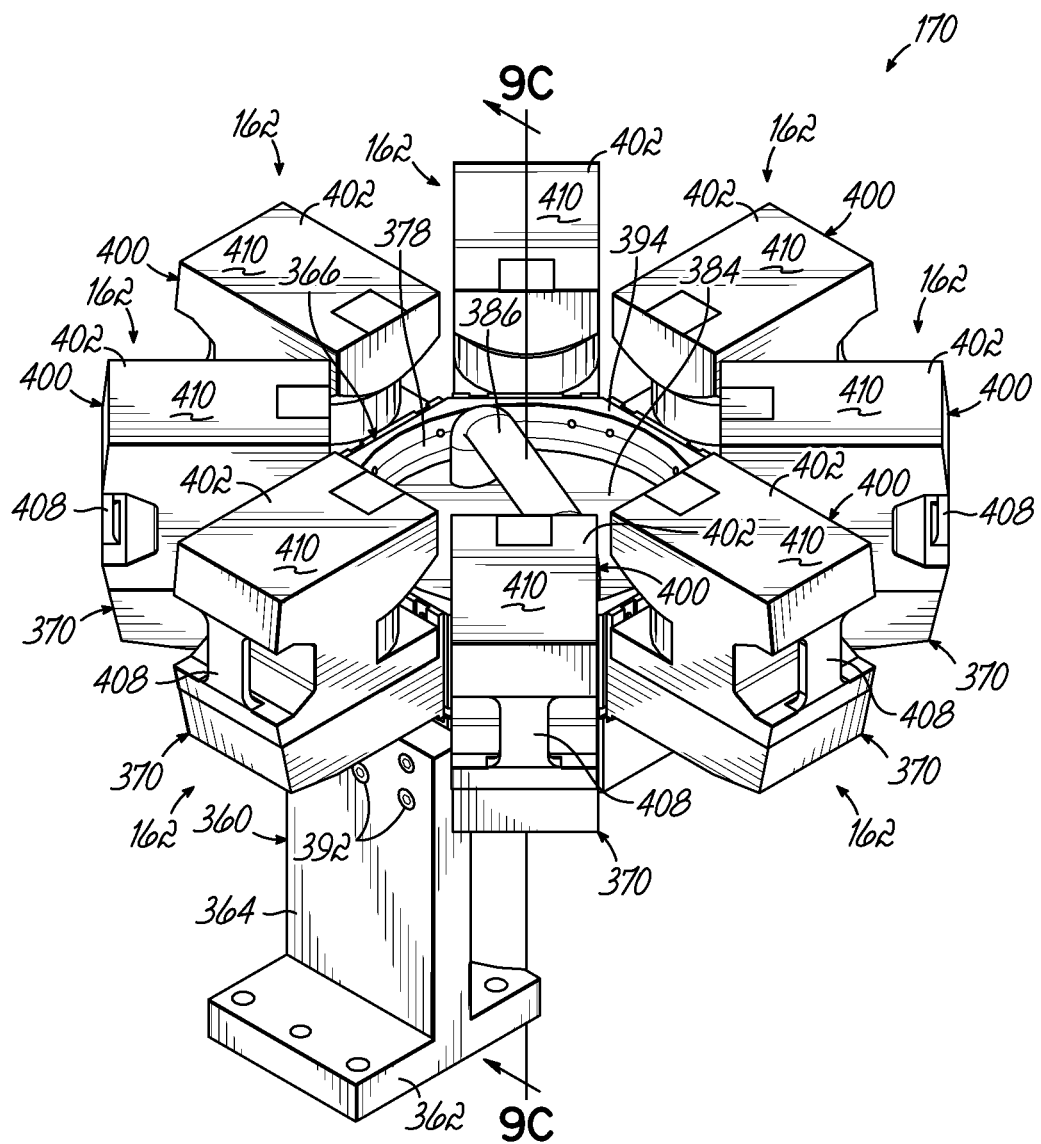
FIG. 9B is a perspective view of the feeder base of FIG. 9A.

Turning now with reference to FIGS. 9A through 9D, the feeder base 170 is illustrated in further detail. The feeder base 170 is configured to receive up to eight of the cassettes 162 at a time and actuate dispensing of unit doses from any combination of those cassettes 162 for a desired blister pack 90. As described briefly above, the feeder base 170 is positioned at the 12 o'clock position of the rotary dial 164, which is also referred to as the filling position. To this end, the feeder base 170 includes a support base 360 in the shape of an inverted T coupled to the turntable platform 210. The bottom end 362 of the support base 360 is fastened to the turntable platform 210 by threaded fasteners (not shown) and the top end 364 of the support base 360 is coupled to a central manifold receptacle 366 of the feeder base 170. The central manifold receptacle 366 projects from a side of the support base 360 to cover a nest 166 on the rotary dial 164 (see FIG. 9C). The central manifold receptacle 366 is formed as a hollow bowl shaped member configured to receive a central manifold 368 as shown in FIGS. 9A and 9B. The feeder base 170 also includes a plurality of actuator petals 370 extending radially outwardly from the central manifold receptacle 366. Each of the actuator petals 370 is configured to receive a corresponding cassette 162 as shown in FIGS. 9A and 9B and described in further detail below. Although eight actuator petals 370 are shown in the exemplary embodiment to correspond to the eight compartments 94 of each blister pack 90, it will be understood that the feeder base 170 may be modified in other embodiments to have more or fewer actuator petals 370 when the design of the blister pack 90 is modified. The feeder base 170 therefore aligns cassettes 162 with compartments 94 without necessitating rotational or relative movement of the cassettes 162 to the blister pack 90 during dispensing.

In addition to actuating each of the necessary cassettes 162 for a selected blister pack 90, the feeder base 170 serves collectively to define a series of dispensing chutes 372 communicating between an outlet 374 of the cassette 162 and a compartment 94 in the blister pack 90 located in the nest 166 below the feeder base 170. To this end, each actuator petal 370 includes a first chute portion 372a extending from an upper surface 376 of the actuator petal 370 to an inner circumferential surface 378 of the central manifold receptacle 366. The first chute portion 372a is gently angled at the inner circumferential surface 378 such that the first chute portion 372a begins moving dropped unit doses inwardly towards the central manifold 368 and the blister pack 90. The central manifold 368 includes a corresponding plurality of second chute portions 372b positioned to extend between an outer peripheral surface 380 of the central manifold 368 to a bottom surface 382 of the central manifold 368. The second chute portions 372b continue the same gentle angling inwardly as the first chute portions 372a such that each unit dose is smoothly guided along the substantially continuous chute 372 into the corresponding compartment 94 of the blister pack 90. Two of the eight continuous chutes 372 are shown in the assembled state in the cross section of FIG. 9C, which illustrates how the chutes 372 are configured to provide a smooth sliding surface to prevent unit doses from catching on or becoming stuck within the feeder base 170.

Figure 9C:
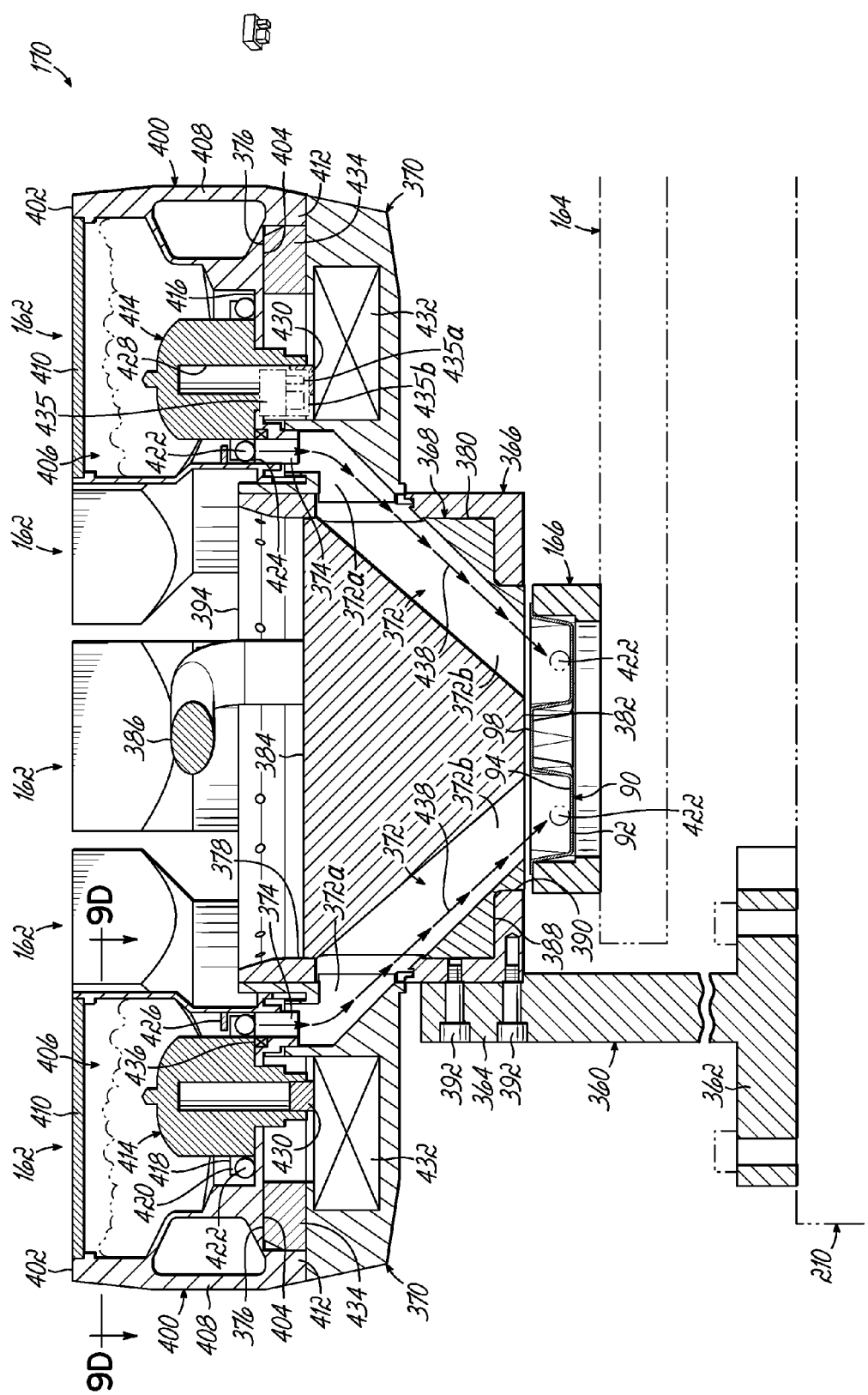
FIG. 9C is a cross-sectional side view of the feeder base and two of the cassettes shown in FIG. 9B, thereby illustrating movement of unit doses of medication from the cassettes into a medication packaging within a nest located below the feeder base.

With continued reference to FIGS. 9A through 9C, the central manifold 368 includes a top surface 384 opposite the bottom surface 382. The top surface 384 includes a handle 386 configured to enable manual insertion and removal of the central manifold 368 into and out of the central manifold receptacle 366. The central manifold 368 is designed as a separate and removable element to enable easier cleaning of the chutes 372 when such cleaning is required. In this regard, any blockages of medications or misalignments of the chute portions 372a, 372b may be readily addressed without substantially delaying the automated packaging process. As shown most clearly in FIG. 9C, the central manifold 368 is shaped as a generally continuous cylindrical member between the top and bottom surfaces 384, 382 except at the bottom surface 382, where the central manifold 368 includes an internal shoulder 388 configured to mate with the corresponding opening 390 at the bottom of the central manifold receptacle 366. Consequently, the bottom surface 382 of the central manifold 368 and the bottom of the central manifold receptacle 366 are configured to be aligned with one another when the central manifold 368 is inserted into the central manifold receptacle 366. Additionally, the central manifold receptacle 366 positions the opening 390 immediately adjacent to the corresponding nest 166 on the rotary dial 164 such that the bottom surface 382 of the central manifold 368 nearly abuts the top surface 98 of the blister pack 90 within the nest 166. As a result, the dispensing chutes 372 lead directly into the compartments 94 of the blister pack 90 without leaving a gap between the feeder base 170 and the blister pack 90 that would be large enough to permit escape of the unit doses from the compartments 94 (such as if the unit doses bounce around upon initial dispense into the compartments 94).

Also as shown in FIG. 9C, the central manifold receptacle 366 is coupled to the top end 364 of the support base 360 with threaded fasteners 392. Although the threaded fasteners 392 do not extend into abutting or threaded engagement with the central manifold 368 in the exemplary embodiment, it will be understood that the threaded fasteners 392 could be modified for either of these engagements in other embodiments where it is desired to positively fix the angular orientation of the central manifold 368. The central manifold receptacle 366 includes a top end 394 which tapers slightly outwardly in a funnel shaped configuration to assist with the manual insertion of the central manifold 368 into the central manifold receptacle 366. Below this top end 394, the inner circumferential surface 378 of the central manifold receptacle 366 is sized to snugly receive the outer peripheral surface 380 as shown in FIG. 9C.

The connection of one of the cassettes 162 to one of the actuator petals 370 is shown in further detail in the exploded view of FIG. 9A and the cross sectional view of FIG. 9C. The cassette 162 in the exemplary embodiment is commercially available from JVM Co., Ltd. of Daegu, Korea and is shown in simplified detail in FIGS. 9A and 9D (although it will be understood that similar cassettes from other suppliers may also be used with the automated packaging station 16). To this end, the cassette 162 defines a generally box-shaped housing 400 extending between a top end 402 and a bottom end 404, the housing 400 enclosing a hopper 406 containing bulk supply of a medication. Between the top end 402 and the bottom end 404, the housing 400 may include structural contours or features such as a handle 408 which assist with robotic and manual movement of the cassette 162. The top end 402 includes a removable lid 410 that may be removed to access the hopper 406, such as when the cassette 162 requires refilling of bulk supply. The bottom end 404 of the cassette defines a hollow space surrounded by an outer circumferential lip 412 projecting from the bottom end 404 as shown most clearly in FIG. 9A. A dispensing drum 414 located substantially within the hopper 406 also extends partially below the bottom end 404 within the outer circumferential lip 412 so as to engage actuating elements of the actuator petals 370 described below.

The dispensing drum 414 and hopper 406 are shown in further detail in FIG. 9D, which is a cross sectional top view looking into a bottom 416 of the hopper 406. The hopper 406 generally funnels downwardly towards the bottom 416, which is defined as an annular space around the dispensing drum 414. The dispensing drum 414 includes a plurality of separating fins 418 extending radially outwardly into this annular space at the bottom 416 of the hopper 406, thereby defining dispensing slots 420 sized to permit only a single unit dose 422 of the medication to fall between the adjacent separating fins 418. The force of gravity and a stepwise driven rotation of the dispensing drum 414 jostle the unit doses 422 in the hopper 406 to cause one unit dose 422 to fall into each dispensing slot 420 as the separating fins 418 rotate about the bottom 416 of the hopper 406. The bottom 416 is completely solid around the annular space except at a dispensing opening 424 located at one stepwise position of the dispensing slots 420. The dispensing opening 424 is covered at the top by a blocking plate 426 such that the dispensing opening 424 only communicates with the dispensing slot 420 rotated into position above the dispensing opening 424. As shown most clearly in FIG. 9C, the blocking plate 426 is located just above the separating fins 418 so that the separating fins 418 rotate freely underneath the blocking plate 426. The blocking plate 426 prevents more than one unit dose 422 from falling out of the dispensing opening 424 at a single time. Thus, as the dispensing drum 414 rotates in stepwise fashion, each dispensing slot 420 is filled by a unit dose 422 falling between the separating fins 418 and then further rotated until alignment with the dispensing opening 424, at which point the unit dose 422 falls out of the dispensing slot 420 and out of the cassette 162 to empty the dispensing slot 420 for further use. Accordingly, stepwise rotation of the dispensing drum 414 actuates separation of the bulk supply of unit doses 422 into single unit doses 422 within the dispensing slots 420 and then actuates dispensing of those single unit doses 422 individually through the dispensing opening 424.

Returning with reference to FIG. 9C, the dispensing drum 414 includes a splined aperture 428 facing toward the bottom end 404. The splined aperture 428 is configured to receive a splined drive shaft 430 extending upwardly from the upper surface 376 of the actuator petals 370. It will be understood that alternative engagement mechanisms other than splines (which are not shown in FIG. 9C) may be provided in other embodiments of the aperture 428 and drive shaft 430 consistent with the scope of the invention. For example, the drive shaft 430 may engage gears (not shown) that engage the dispensing drum 414 in other embodiments. The drive shaft 430 is operatively connected to a motor 432 held within the actuator petal 370. The motor 432 is configured to drive the drive shaft 430 and therefore also the dispensing drum 414 in stepwise fashion to cause movement of the dispensing slots 420 around the hopper bottom 416 as described in detail above. The upper surface 376 of the actuator petals 370 also includes an alignment plate 434 with a beveled profile which guides the outer circumferential lip 412 at the bottom end 404 of the cassette 162 into proper alignment with the actuator petal 370. Thus, the beveled profile ensures that the drive shaft 430 correctly mates within the splined aperture 428 of the dispensing drum 414 and also ensures that the dispensing opening 424 of the cassette 162 aligns with the first chute portion 372a in the actuator petal 370.

Also as shown in FIGS. 9A and 9C, the cassette 162 includes a memory chip 435 configured to retain and supply identification information pertaining to the cassette 162. The memory chip 435 in the exemplary embodiment is in the form of an EEPROM chip with an interface 435a (pins) projecting from the bottom end 404 so as to engage a corresponding petal interface 435b (socket) on the corresponding actuator petal 370. It will be understood that other types of memory chips 435, including those capable of being read wirelessly without a connection interface, may be used instead of the EEPROM chip in other embodiments of the invention. The memory chip 435 operates to store (in a re-writable manner) one or more items of identification information such as a canister number assigned to the cassette 162. The cassette 162 in the exemplary embodiment also includes machine readable indicia (not shown) in the form of a barcode that may be scanned to provide identification information whenever the first robot 44 picks up the cassette 162 from the storage carousels 160 or from the refill window 176.

In operation, the memory chip 435 is polled for the identification information whenever the cassettes 162 are positioned onto the actuator petals 370 of the feeder base 170. As a result, the machine controller 42 verifies the identity of the cassettes 162 both when the cassettes 162 are picked up from the storage carousels 160 by the first robot 44 (with the previously-described barcode scanning) and when the cassettes 162 are positioned in an array on the feeder base 170. Additionally, whenever the operation of the automated packaging station 16 is interrupted and restarted, it may be determined whether the barrier wall 150 was opened during the inoperative time period, which would indicate operator entry into the robotic work zone 152. If such an intrusion into the robotic work zone 152 occurred, then each of the memory chips 435 on the cassettes 162 at the feeder base 170 are polled once again to ensure that the operator did not move the cassettes 162 around to different actuator petals 370 during the inoperative time. Accordingly, the provision of the barcode and the memory chip 435 on each cassette 162 enables the machine controller 42 to continuously monitor and verify the identity of all cassettes 162 moving within the robotic work zone 152. This leads to higher accuracy of filling blister packs 90 and less time needed for downstream manual verification.

The operation of the feeder base 170 is described with reference to FIG. 9C. The rotary dial 164 rotates in stepwise manner to position a nest 166 with an empty blister pack 90 beneath the feeder base 170. The machine controller 42, which is operatively coupled to the motors 432 in the feeder base 170, sends a signal to actuate stepwise rotation of each dispensing drum 414 in the cassettes 162 which are needed to dispense a unit dose 422 into a compartment 94 of the blister pack 90. As described above, this may be any combination of the cassettes 162 depending on the particular medication pass time to be served by the blister pack 90. Each of the cassettes 162 includes a photoelectric sensor 436 located adjacent the dispensing opening 424. This sensor 436 is operable to detect if a unit dose 422 has dropped through the dispensing opening 424 into the chute 372 of the feeder base 170. Consequently, the motor 432 connected to the dispensing drum 414 of a cassette 162 can be actuated again (up to 3 times, for example) if no unit dose 422 is detected by the sensor 436 on board the cassette 162 when such a unit dose 422 should have been dropped. If no unit dose 422 is detected by sensor 436 after repeated actuations of the motor 432, then the motor 432 may be operated in reverse to attempt to dislodge a jam in the cassette 162 before trying to dispense a unit dose 422 once again. If this process is unsuccessful, then a fault will occur in the control and the cassette 162 will be flagged for maintenance and repair.

Thus, the sensor 436 on the cassette 162 operates as a first verification for whether the appropriate unit doses 422 are dropped into the compartments 94 on the blister pack 90. When the dispensing drums 414 are actuated as described above, the unit doses 422 fall from the position within the dispensing slot 420 through the dispensing opening 424 and through the chute 372 as shown by arrows 438 into the appropriate compartment 94 (the final position being shown in phantom in FIG. 9C). The blister pack 90 is therefore filled with each of the unit doses 422 simultaneously by the feeder base 170 before being rotated to the additional processing stations around the rotary dial 164 as described in detail above.

As the empty blister packs 90 are loaded onto the nests 166 of the rotary dial 164, each nest 166 in series is filled with a blister pack 90 until the corresponding set of blister packs 90 (e.g., 30 packs for a particular medication pass or 6 packs of PRN in the exemplary embodiment) is finished loading on the nests 166. The machine controller 42 operates to cause the packaging magazines 168 to then skip the next empty nest 166 rotating past the packaging magazines 168 to leave one empty nest 166 between sets of blister packs 90 on the rotary dial 164. This empty nest 166 will be located underneath the feeder base 170 at the filling position when the cassettes 162 are removed and replaced for the next set of blister packs 90 at the feeder base 170. To this end, the chutes 372 in the feeder base 170 will lead directly into and through the apertures 248, 256 in the nest 166 and rotary dial 164 when the empty nest 166 is located at the filling position. Consequently, if any of the splined apertures 428 and dispensing drums 414 are accidentally rotated by being jostled during connection of the cassettes 162 onto the actuator petals 370, any unit doses 422 that drop into the chutes 372 will pass through the feeder base 170 and through the empty nest 166 without being collected in a blister pack 90 that is to be used for another purpose. This operation further ensures that fewer errors will occur during the filling of the blister packs 90 with the automated packaging station 16. It will be understood that a container or receptacle (not shown) may be mounted underneath the rotary dial 164 at the filling position to collect any of these accidentally dropped unit doses 422 in some embodiments of the invention.

The exemplary embodiment of the loading staging table 172, which is identical to the unloading staging table 174, is shown in further detail with reference to FIGS. 10A through 10D. The loading staging table 172 is configured to enable movement of up to four and up to eight cassettes 162 at once using the first robot 44. More specifically, the first robot 44 may be provided with different gripping heads configured to grip up to four cassettes 162 or up to eight cassettes 162 at a time, as described in further detail with reference to FIGS. 11A through 12L below. Consequently, the loading staging table 172 must be operable to hold eight of the cassettes 162 in the same orientation and layout as used on the feeder base 170 described above. The loading staging table 172 must also be operable to move a subset of four of those cassettes 162 so that the different gripping heads of the first robot 44 may be used to successfully pick up and drop off cassettes 162 onto the loading staging table 172.

Figure 10A:
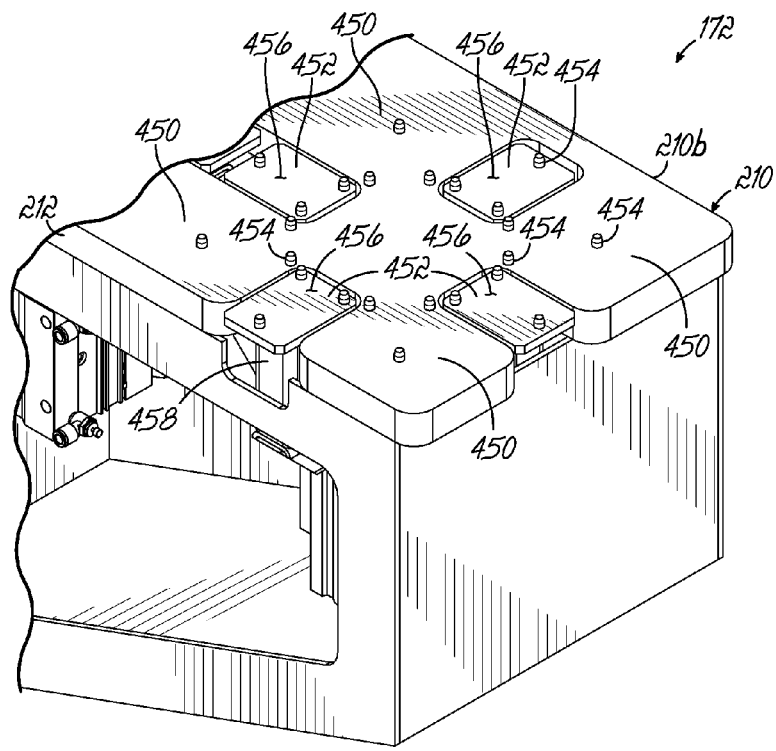
FIG. 10A is a perspective view of one of the loading and unloading staging tables located adjacent the feeder base of FIG. 9A on the turntable assembly of FIG. 5.
Figure 10B:
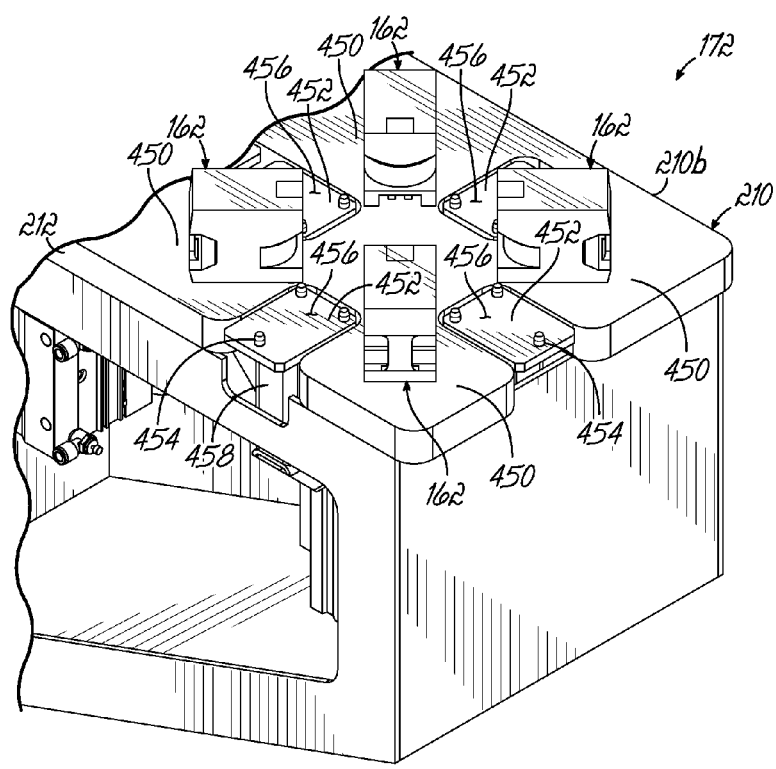
FIG. 10B is a perspective view of the staging table of FIG. 10A, with four cassettes positioned on stationary platens of the staging table.

With particular reference to FIG. 10A, the loading staging table 172 therefore includes four stationary platens 450 formed in the projecting portion 210b of the turntable platform 210 and four moveable platens 452 located between corresponding pairs of the stationary platens 450. The stationary platens 450 include three aligning pins 454 projecting upwardly from the turntable platform 210. The aligning pins 454 are positioned and spaced from one another such that the outer circumferential lip 412 at the bottom end 404 of the cassette 162 will snugly fit around the aligning pins 454. In this regard, two of the aligning pins 454 are located at the corners of the outer circumferential lip 412 along one side of the cassette 162 while the other aligning pin 454 is located adjacent the outer circumferential lip 412 along an opposing side of the cassette 162. It will be understood that the aligning pins 454 may be reconfigured in any orientation in other embodiments of the loading staging table 172 as long as the aligning pins 454 are positioned to accurately and repeatably align each of the cassettes 162 with one another on the loading staging table 172.

Figure 10C:
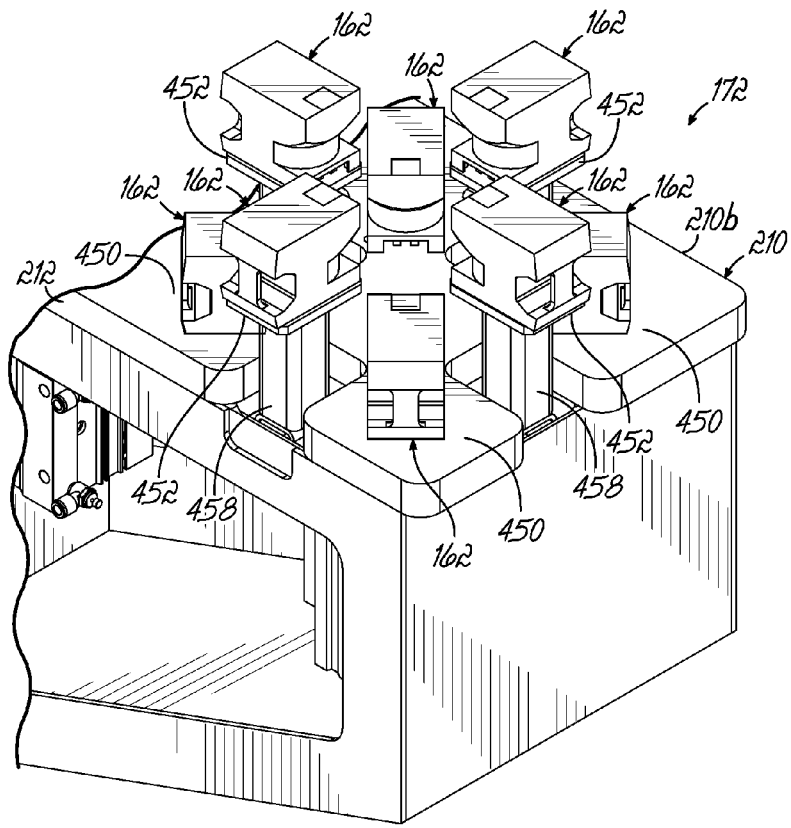
FIG. 10C is a perspective view of the staging table of FIG. 10B, with four movable platens moved to a raised position above the four cassettes shown in FIG. 10B and with four additional cassettes placed on the raised platens.
Figure 10D:
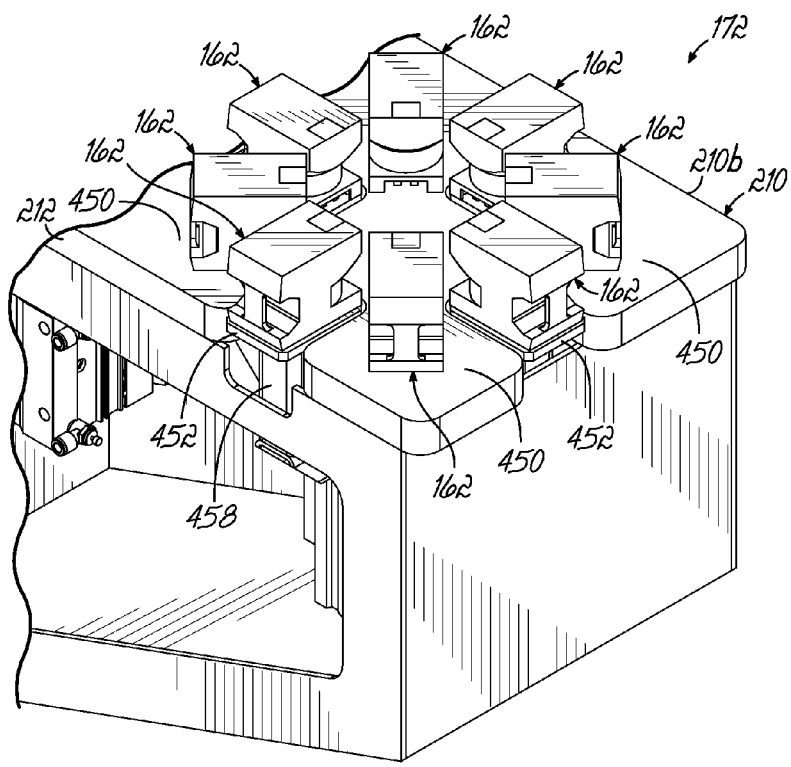
FIG. 10D is a perspective view of the staging table of FIG. 10C, with the movable platens moved back to a lowered position such that all eight cassettes are generally coplanar.

The four moveable platens 452 shown in FIG. 10A also include aligning pins in the same manner as the four stationary platens 450 described above. In addition, the four moveable platens 452 also include support platforms 456 that are mounted for movement between a lowered position generally coplanar with the stationary platens 450 (FIG. 10A) to a raised position lifted above the four stationary platens 450 (FIG. 10C). To this end, the support platforms 456 are mounted on lift arms 458 that are collectively coupled to a motor or other actuator (not shown) configured to lift each of the support platforms 456 simultaneously. For example, the lift arms 458 are pneumatic cylinders in the exemplary embodiment consistent with the invention. Thus, the four moveable platens 452 are substantially identical to the four stationary platens 450 except for possessing the ability to be moved to the raised position for reasons set forth below. It will be understood that the unloading staging table 174 includes this same structure of stationary platens 450 and moveable platens 452 and therefore is not described in further detail herein. It will also be understood that the particular layout and number of stationary and moveable platens 450, 452 may be modified in other embodiments of the automated packaging station 16 without departing from the scope of the embodiments of the invention, such as when the blister packs 90 are formed with a different configuration having more or fewer compartments 94.

The exemplary operation of the loading staging table 172 is shown in FIGS. 10A through 10D. The loading staging table 172 begins in the operational state shown in FIG. 10A, with the moveable platens 452 in the lowered coplanar position. The first robot 44 then drops four cassettes 162 onto the stationary platens 450 as shown in the operational state of FIG. 10B. Because the gripping head that holds four cassettes 162 at a time requires additional clearance in the center of the cassettes 162, the moveable platens 452 are then moved to the raised position so that the first robot 44 does not run into the other cassettes 162 on the stationary platens 450 when the other four cassettes 162 are deposited on the moveable platens 452. The moveable platens 452 therefore receive the other four cassettes 162 while in the raised position as shown in FIG. 10C. The moveable platens 452 are then lowered to the lowered position to bring all eight cassettes 162 into vertical alignment with one another on the loading staging table 172 as shown in the operational state of FIG. 10D. This position of the eight cassettes 162 is substantially similar to the position that the cassettes 162 take on the feeder base 170, which enables a separate gripping head of the first robot 44 to retrieve and place all eight cassettes 162 at once, as described below. In summary, the loading staging table 172 enables accurate placement and retrieval of cassettes 162 using gripping heads on the first robot 44 that are alternatively configured to hold up to four cassettes 162 at a time or up to eight cassettes 162 at a time.

Figure 11A:
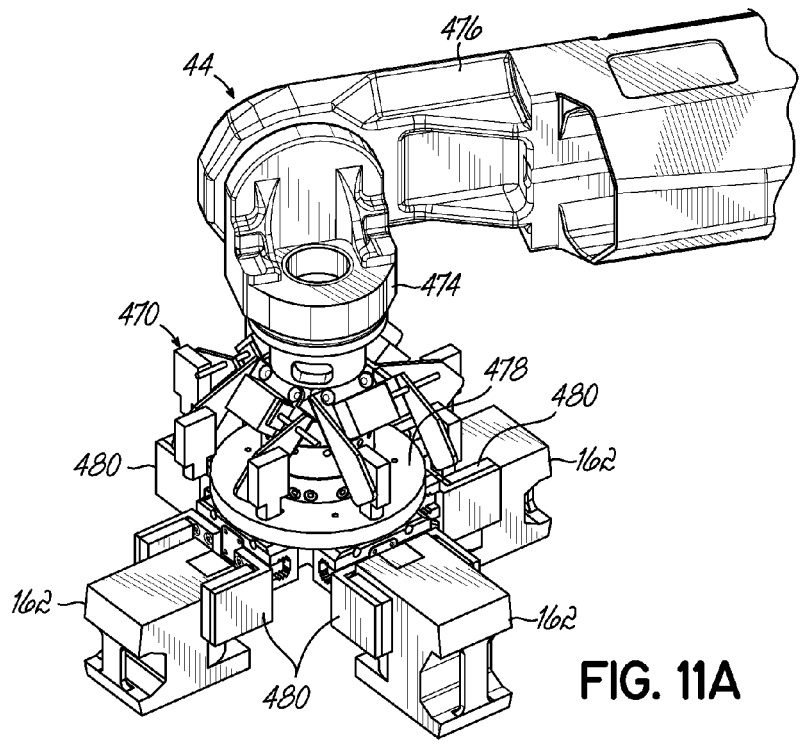
FIG. 11A is a perspective view of a first robot used to move the cassettes around the automated packaging station of FIG. 4, the first robot connected to a first gripping head configured to hold up to four cassettes at a time.
Figure 11B:
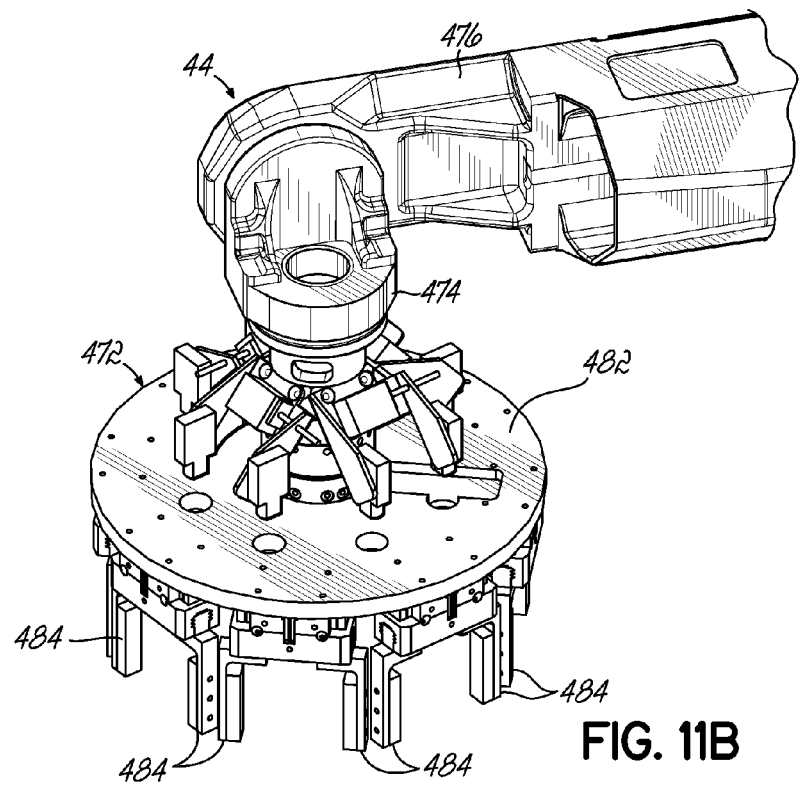
FIG. 11B is a perspective view of the first robot of FIG. 11A, with the first robot connected to a second gripping head configured to hold up to eight cassettes at a time.

With reference to FIGS. 11A and 11B, the first robot 44 is shown in greater detail. As described above, the first robot 44 is configured to operate with two different types of gripping heads: a first gripping head 470 configured to move up to four cassettes 162 simultaneously, and a second gripping head 472 configured to move up to eight cassettes 162 simultaneously. Each of the first and second gripping heads 470, 472 is briefly described as follows. With reference first to FIG. 11A, the first gripping head 470 is removably connected to the free end 474 of the terminal robot arm 476 of the first robot 44 by known methods. For example, an adapter that is commercially supplied with the first robot 44 may be positioned on the free end 474 to enable rapid connection and disconnection to the first and second gripping heads 470, 472 (as well as other tools using the same adapted interface). The first gripping head 470 includes a central platform 478 extending downwardly from the free end 474 and four pairs of gripping arms 480 extending generally radially outwardly from the central platform 478. The central platform 478 includes actuating mechanisms (not shown) for causing the pairs of gripping arms 480 to pinch inwardly to selectively grip a cassette 162. As shown by the cassettes 162 illustrated in FIG. 11A, the first gripping head 470 grips the cassettes 162 from the side, which enables the cassettes 162 to be pushed in a radial direction into and out of the storage carousels 160 as described in further detail below.

Turning to FIG. 11B, the second gripping head 472 is also removably connected to the free end 474 of the terminal robot arm 476 by known methods. The second gripping head 472 includes a top platform 482 and eight pairs of gripping arms 484 extending downwardly from the top platform 482. Similar to the central platform 478 of the first gripping head 470, the top platform 482 also includes actuating mechanisms (not shown) for causing the pairs of gripping arms 484 to pinch inwardly to selective grip a cassette 162. As readily understood from the orientation shown in FIG. 11B, the pairs of gripping arms 484 on the second gripping head 472 may be lowered to grab each of the cassettes 162 from the top, which enables all eight cassettes 162 to be picked up and dropped off simultaneously. As with the other components previously described, the first and second gripping heads 470, 472 may be modified in other embodiments of the invention depending on the particular layout and number of cassettes 162 to be used on the feeder base 170 and on the loading and unloading staging tables 172, 174.

Figure 12A:
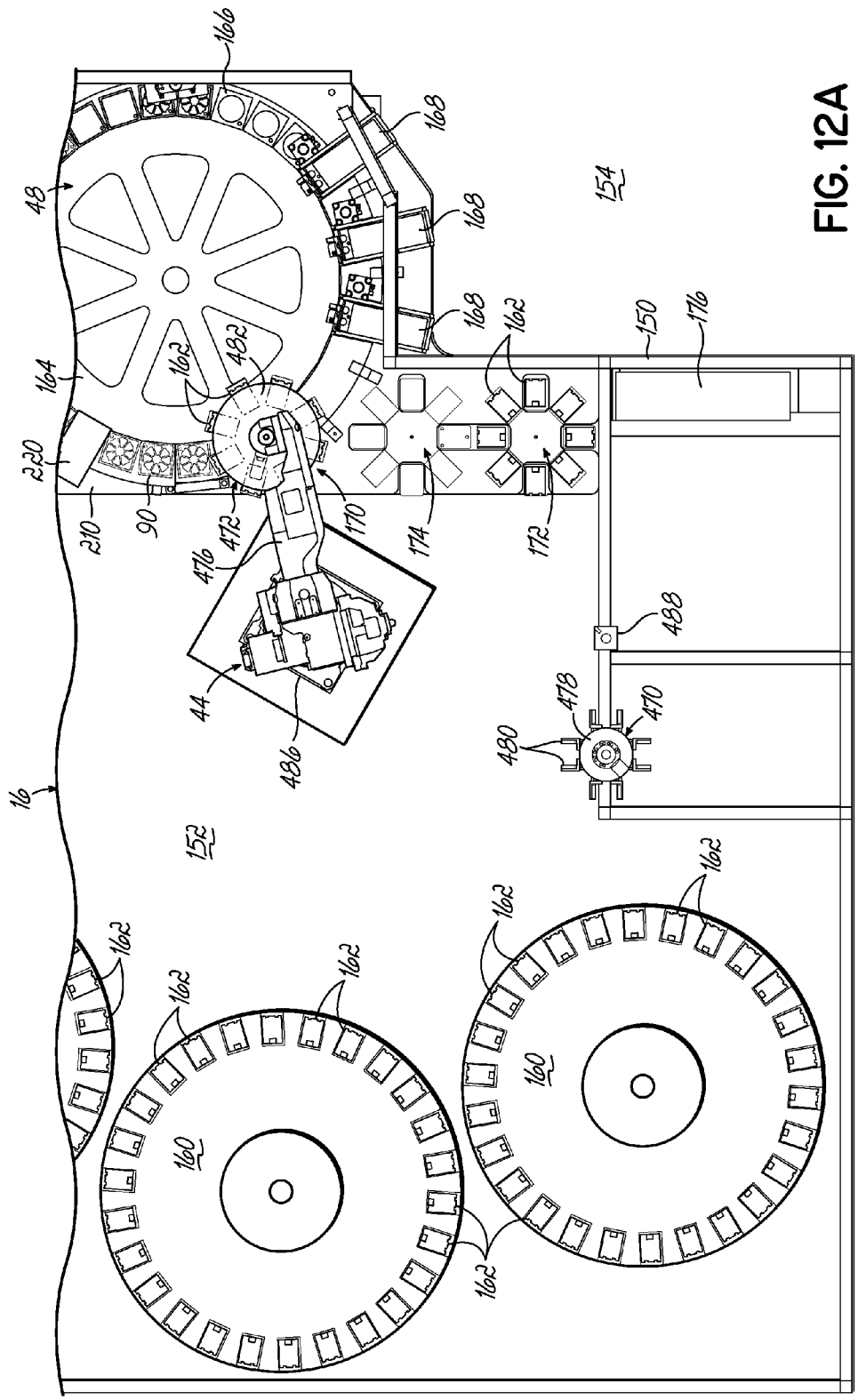
FIG. 12A is a top view of a portion of the automated packaging station of FIG. 4, showing a first operational state of the station in which the first robot of FIG. 11A is positioned with the second gripping head at the feeder base to remove a set of used cassettes.

The operation of the first robot 44 in the robotic work zone 152 is further described with reference to the series of operational states illustrated in FIGS. 12A through 12L. As shown in FIG. 12A, the first robot 44 includes a base support 486 centrally located between the storage carousels 160, the turntable assembly 48, the refill window 176, and a storage location 488 configured to hold each of the first and second gripping heads 470, 472 when not in use. This positioning of the base support 486 is chosen such that the terminal robot arm 476 of the first robot 44 may be moved between each of these locations as a result of the three dimensional articulation enabled by the first robot 44. The first robot 44 operates to move sets of cassettes 162 between the feeder base 170, the staging tables 172, 174, and the storage carousels 160 as described below.

Figure 12B:
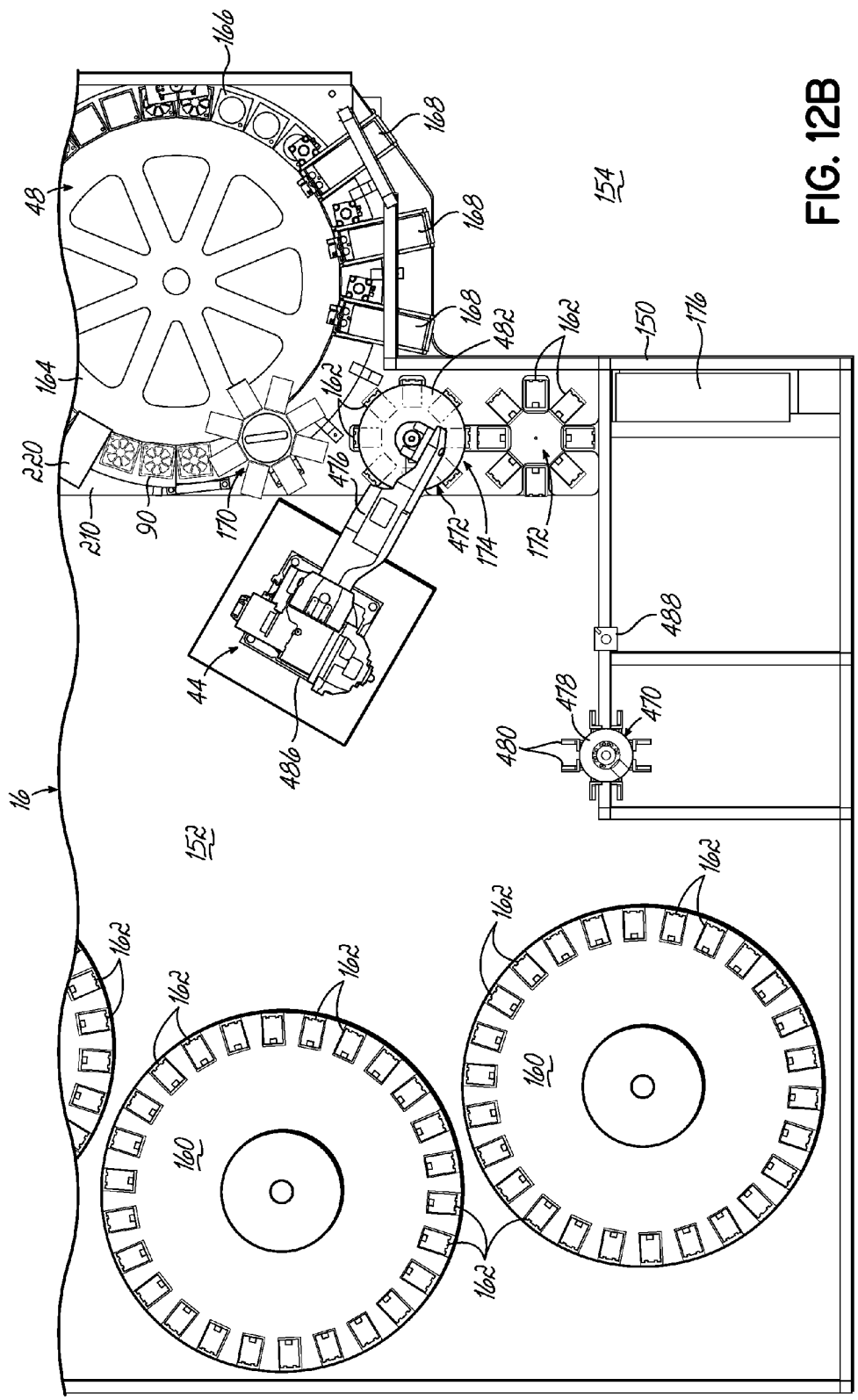
FIG. 12B is a top view similar to FIG. 12A, showing a second operational state of the station in which the first robot has moved the used cassettes to the unloading staging table with the second gripping head.
Figure 12C:
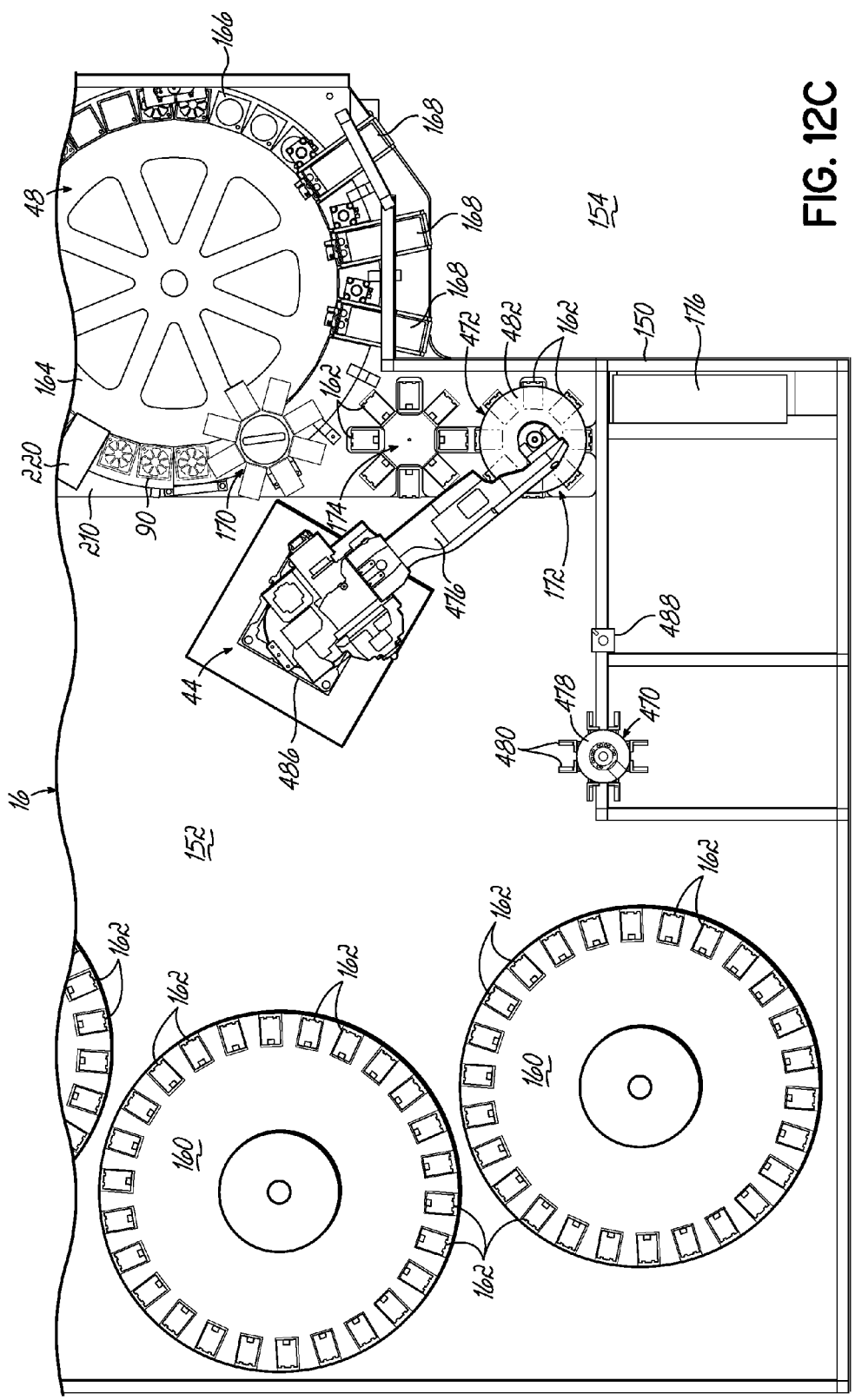
FIG. 12C is a top view similar to FIG. 12B, showing a further operational state of the station in which the first robot has moved with the second gripping head to the loading staging table, which is already loaded with eight new cassettes for the feeder base.
Figure 12D:
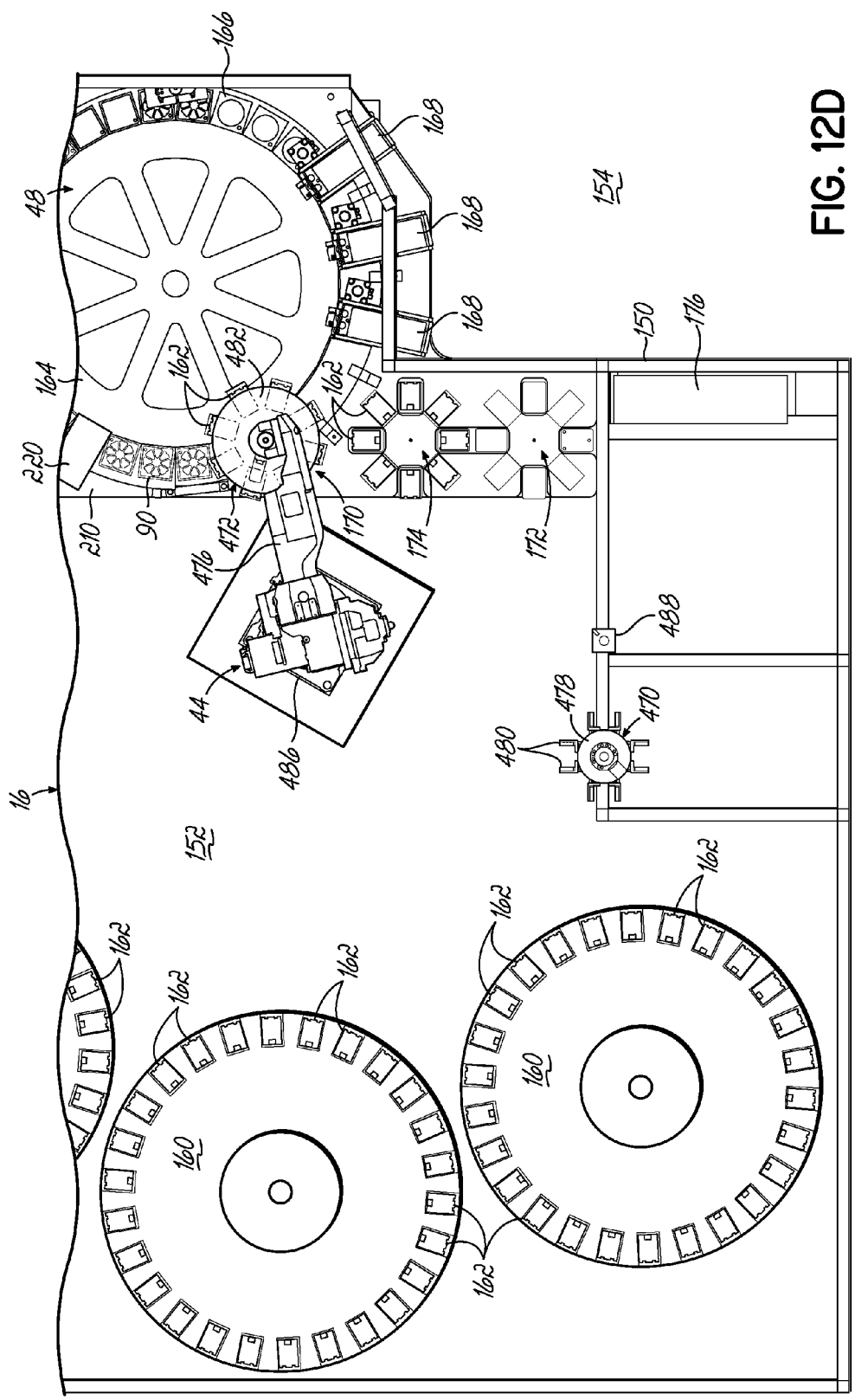
FIG. 12D is a top view similar to FIG. 12C, showing a further operational state of the station in which the first robot has moved the new cassettes to the feeder base with the second gripping head.

Beginning with FIG. 12A, the cassettes 162 on the feeder base 170 have been used and are ready for replacement, while the next set of cassettes 162 have already been loaded on the loading staging table 172. The first robot 44 is connected to the second gripping head 472 and is positioned at the feeder base 170 to pick up the used cassettes 162 on the feeder base 170. Once the second gripping head 472 has actuated the gripping arms 484 to grab all eight cassettes 162 simultaneously, the first robot 44 moves the cassettes 162 onto the unloading staging table 174 with the second gripping head 472 and releases the cassettes 162 as shown in FIG. 12B. The first robot 44 then moves the second gripping head 472 over the eight cassettes 162 at the loading staging table 172 as shown in FIG. 12C. After picking those new cassettes 162 up, the first robot 44 moves those new cassettes 162 to the feeder base 170 as shown in FIG. 12D and drops the cassettes 162 into position on the actuator petals 370 as previously described. The new cassettes 162 are then immediately ready for use at the feeder base 170, and the rotary dial 164 begins rotating new nests 166 with empty blister packs 90 underneath the feeder base 170 for filling. In the exemplary embodiment, the operational steps of FIGS. 12A through 12D to switch out the set of cassettes 162 on the feeder base 170 take only about 4.5 seconds, during which the rotational movement of the rotary dial 164 is temporarily paused.

Figure 12E:
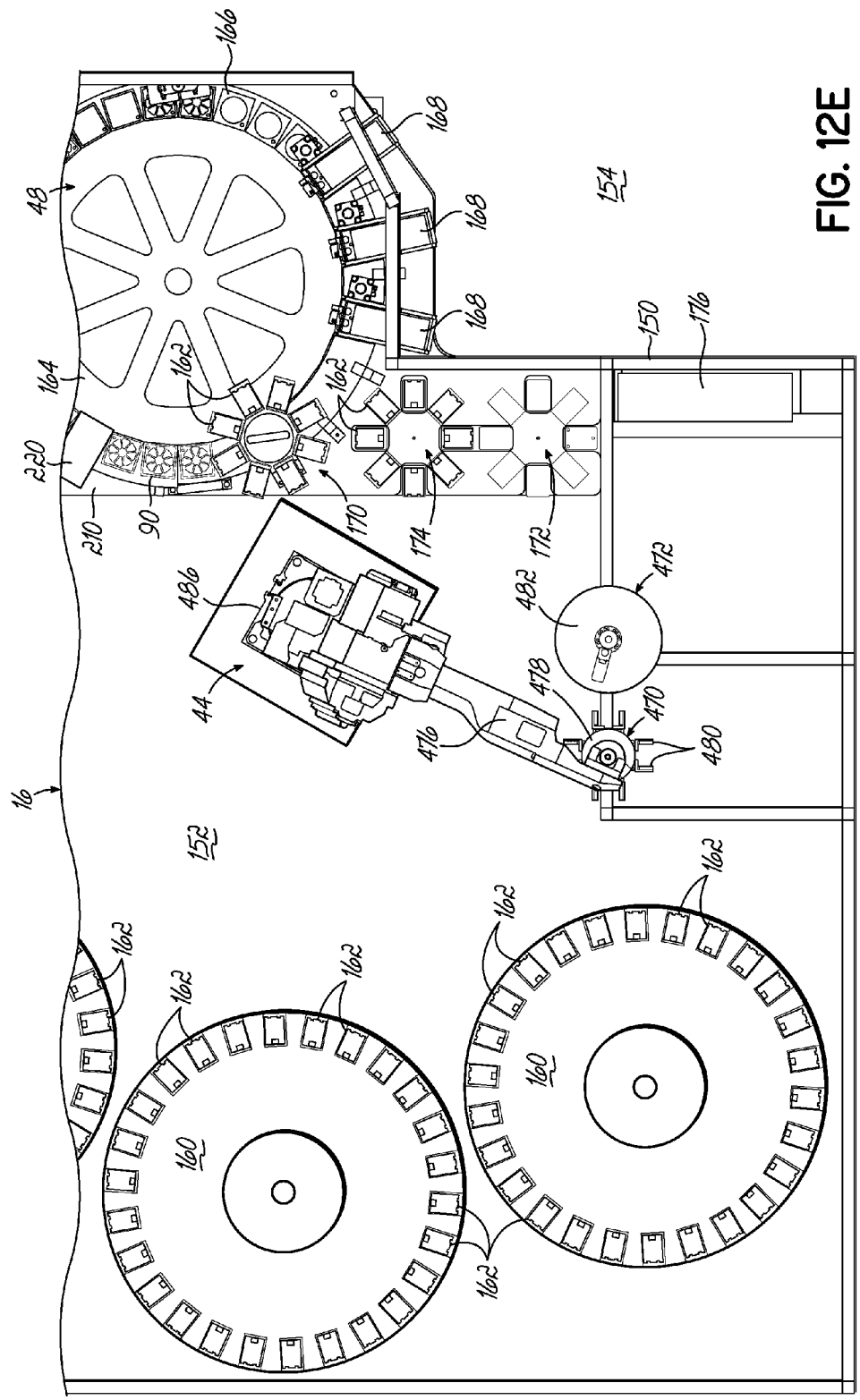
FIG. 12E is a top view similar to FIG. 12D, showing a further operational state of the station in which the first robot has switched from using the second gripping head to using the first gripping head.
Figure 12F:
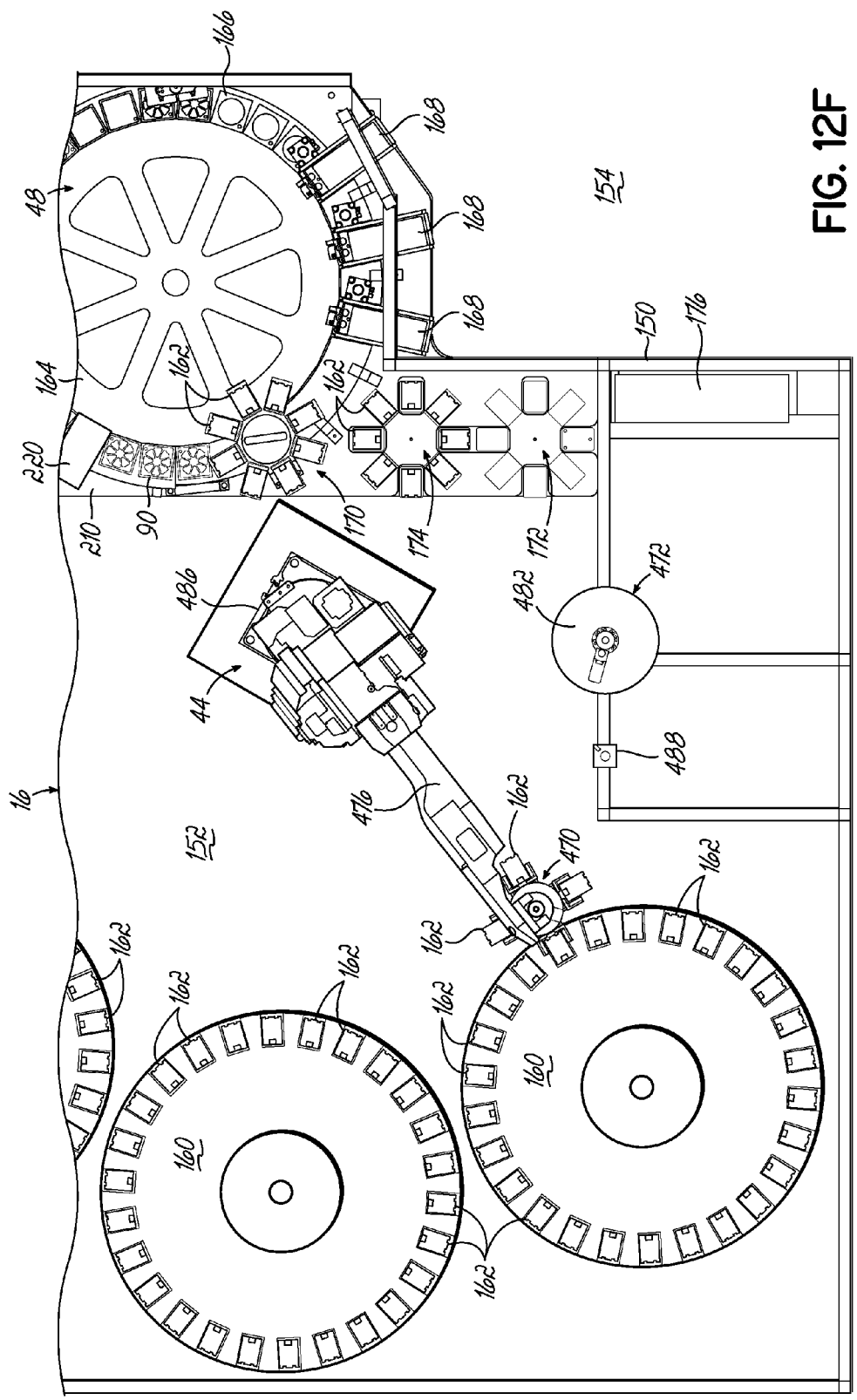
FIG. 12F is a top view similar to FIG. 12E, showing a further operational state of the station in which the first robot begins retrieving a new set of cassettes from storage carousels with the first gripping head.
Figure 12G:
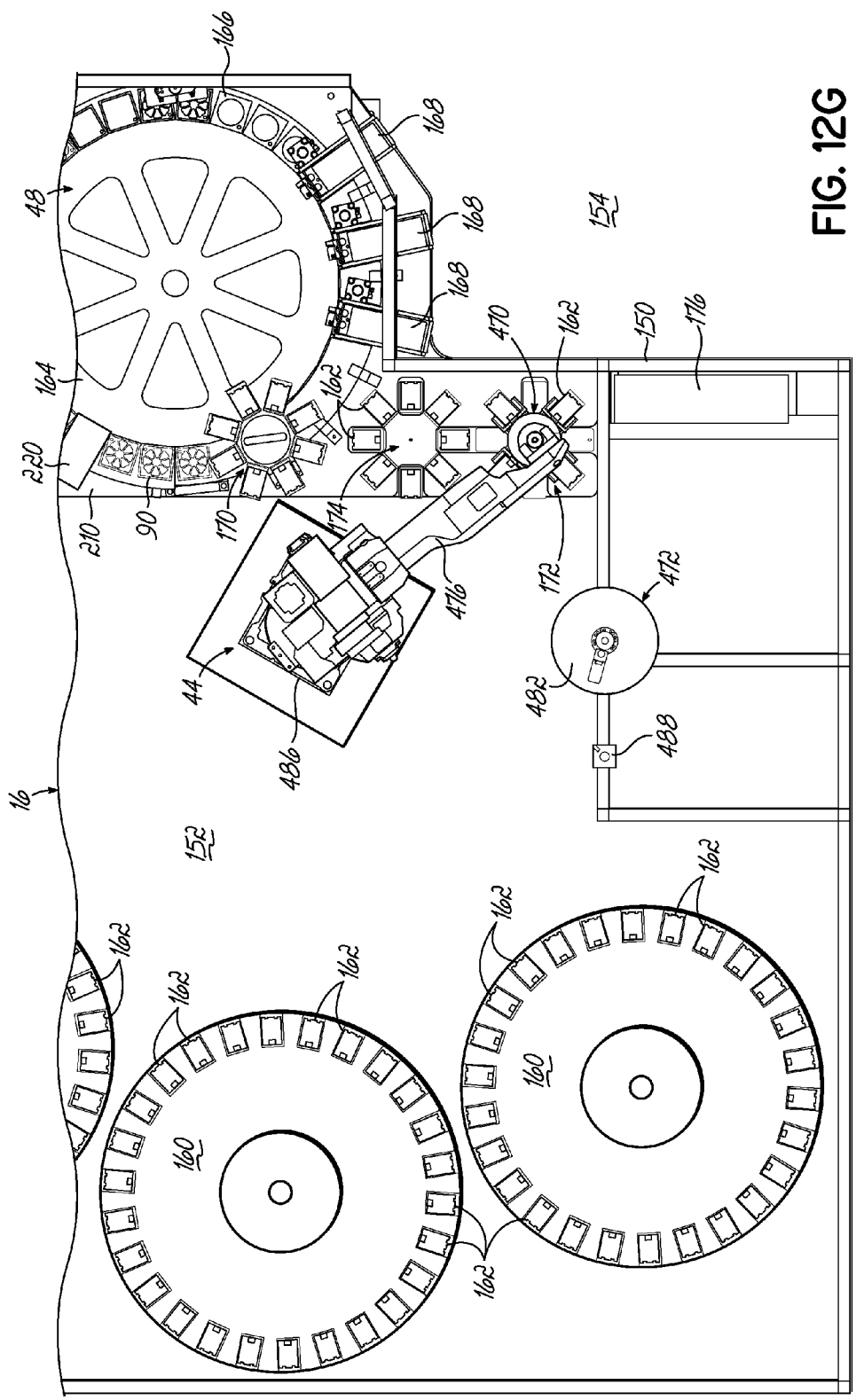
FIG. 12G is a top view similar to FIG. 12F, showing a further operational state of the station in which the first robot is delivering four of the new cassettes to the loading staging table with the first gripping head.
Figure 12H:
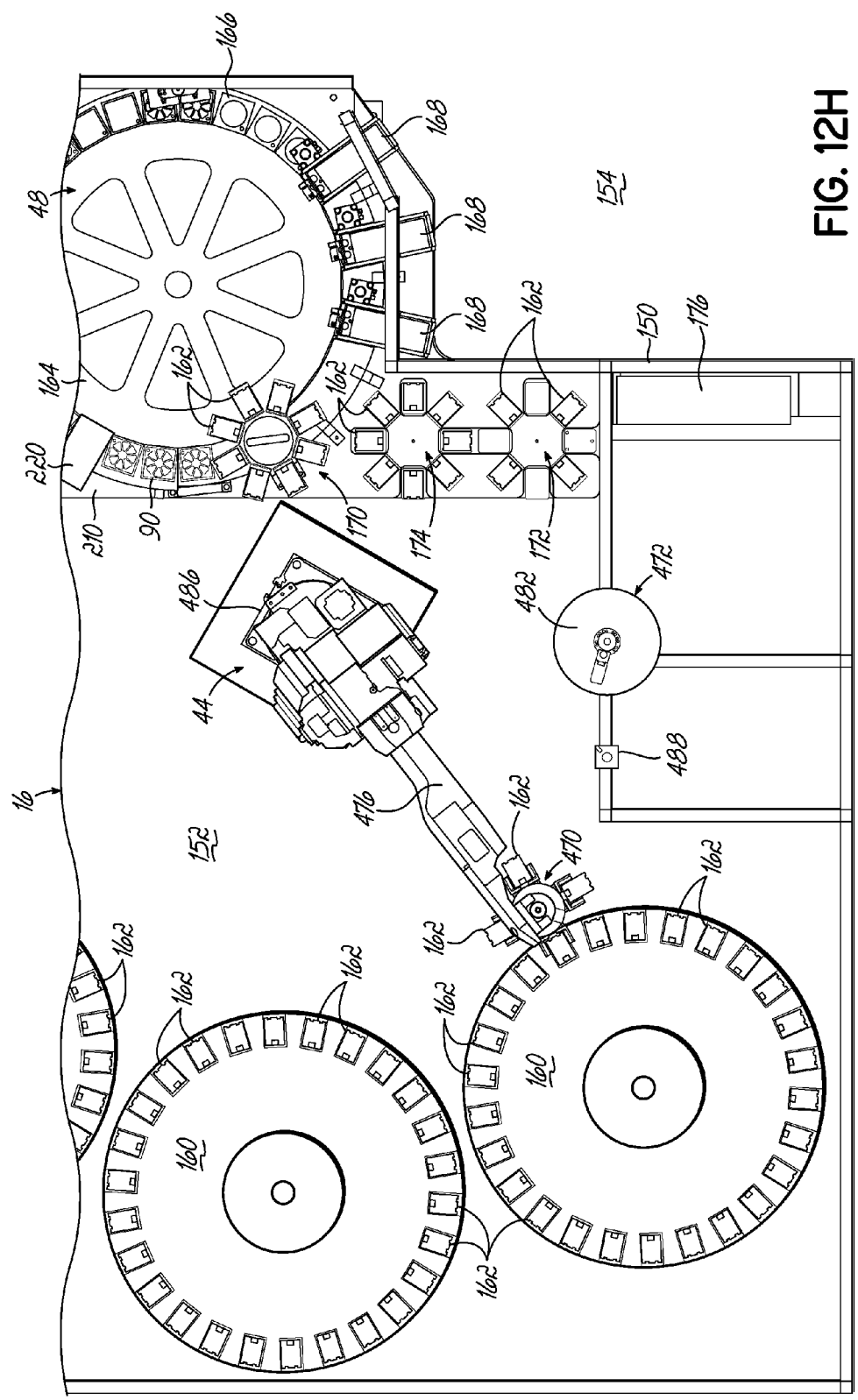
FIG. 12H is a top view similar to FIG. 12G, showing a further operational state of the station in which the first robot continues to retrieve the new set of cassettes from the storage carousels with the first gripping head.

While the rotary dial 164 and feeder base 170 operate to fill the next set of thirty blister packs 90 using the cassettes 162 on the feeder base 170, the first robot 44 prepares the next batch of cassettes 162 by performing the operational steps shown in FIGS. 12E through 12L. As shown in FIG. 12E, the first robot 44 begins by moving to the storage location 488 to switch from the second gripping head 472 to the first gripping head 470. Once the first gripping head 470 is loaded onto the terminal robot arm 476, the first robot 44 moves the first gripping head 470 to the storage carousels 160 to retrieve up to four cassettes 162 needed for the next set of cassettes 162. As described above, the first gripping head 470 is configured to grab the cassettes 162 from the side to enable the movement into and out of the storage carousels 160 as shown in FIG. 12F. After the first four cassettes 162 are retrieved from the storage carousels 160, the first robot 44 moves to the loading staging table 172 and drops the first four cassettes 162 onto the stationary platens 450 with the first gripping head 470 as shown in FIG. 12G. The first robot 44 then returns to the storage carousels 160 with the first gripping head 470 to retrieve the other four cassettes 162 for the next batch of cassettes 162 as shown in FIG. 12H.

Figure 12I:
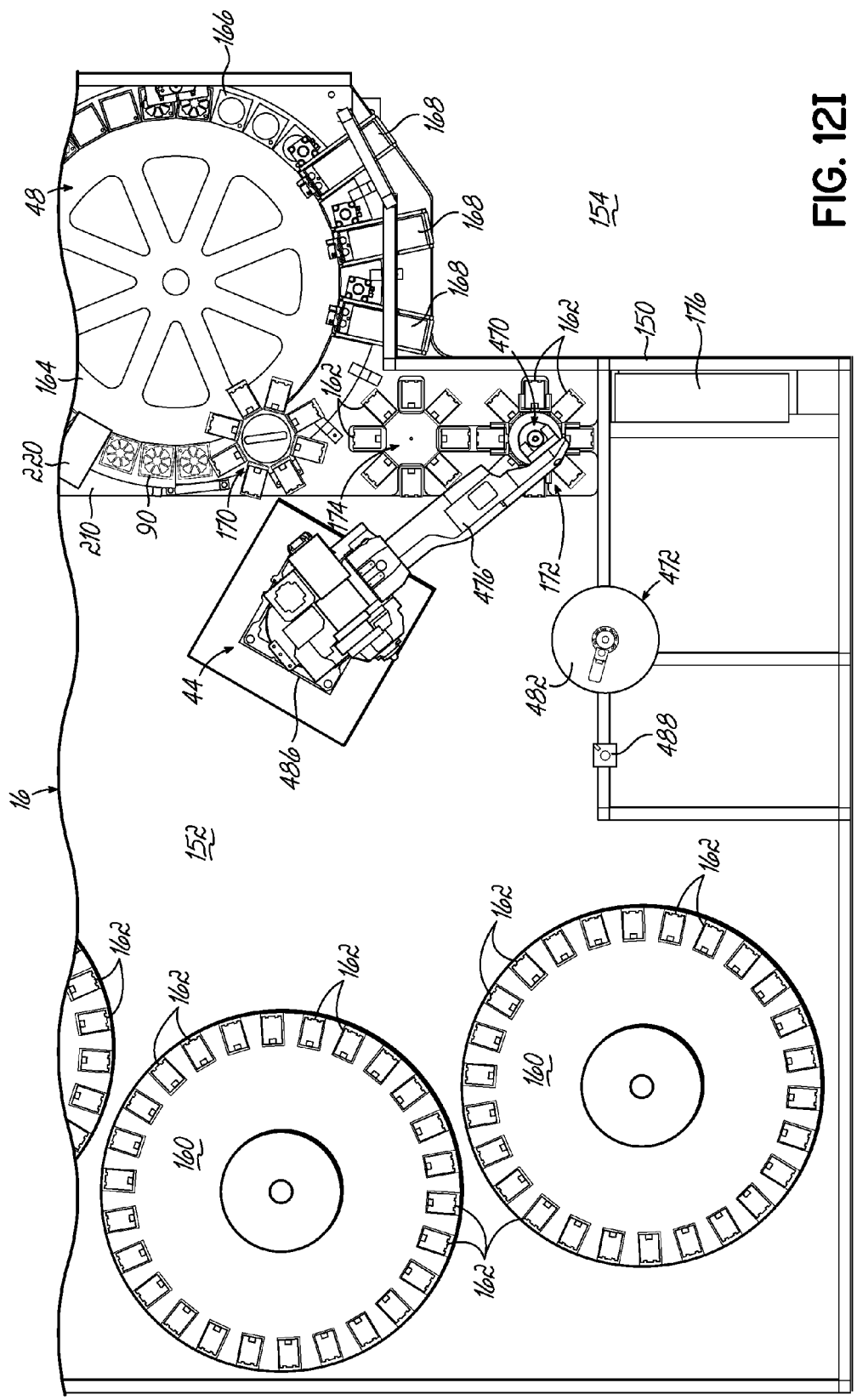
FIG. 12I is a top view similar to FIG. 12H, showing a further operational state of the station in which the first robot is delivering another four of the new cassettes to the loading staging table with the first gripping head.
Figure 12J:
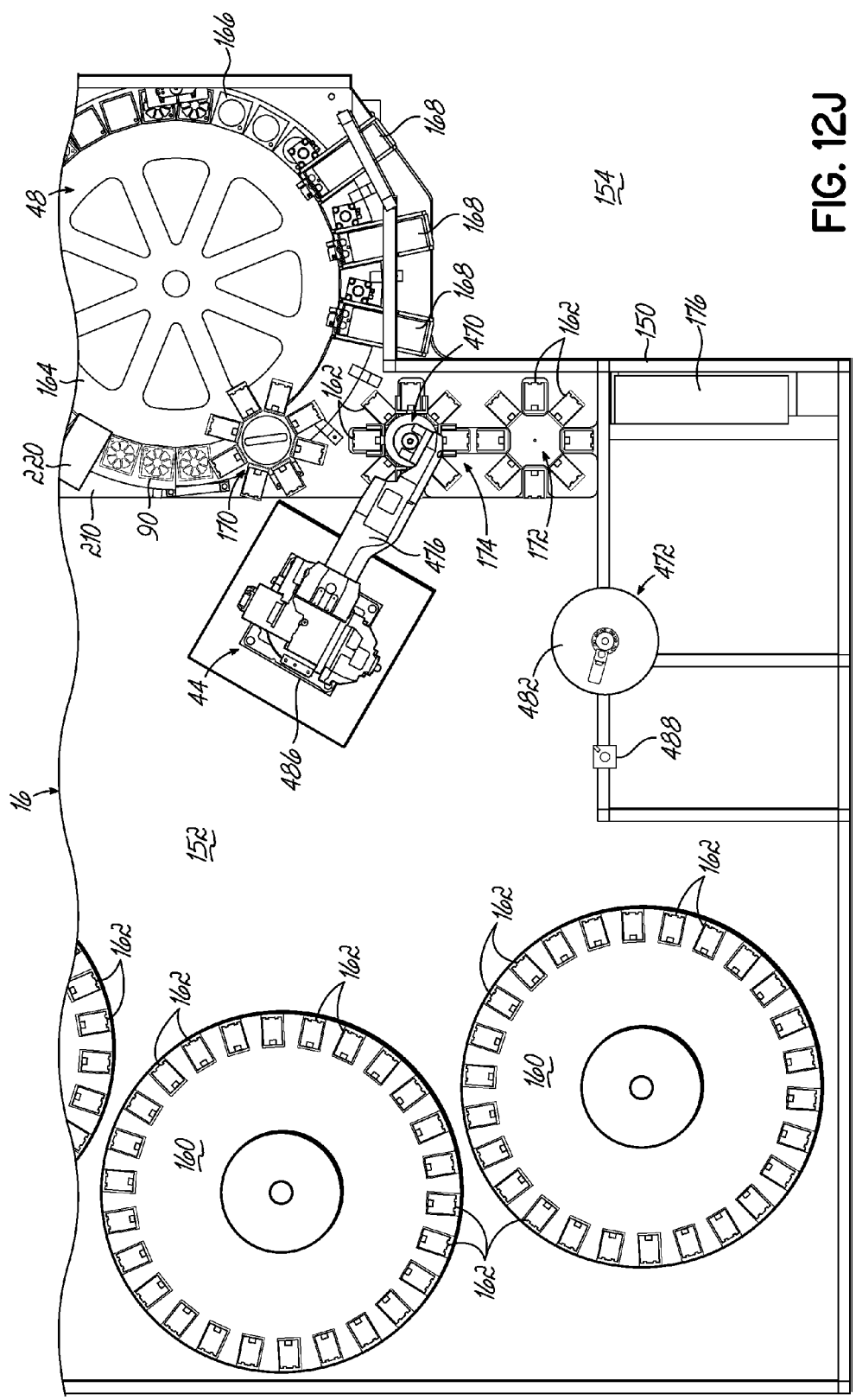
FIG. 12J is a top view similar to FIG. 12I, showing a further operational state of the station in which the first robot retrieves four of the used cassettes on the unloading staging table with the first gripping head.
Figure 12K:
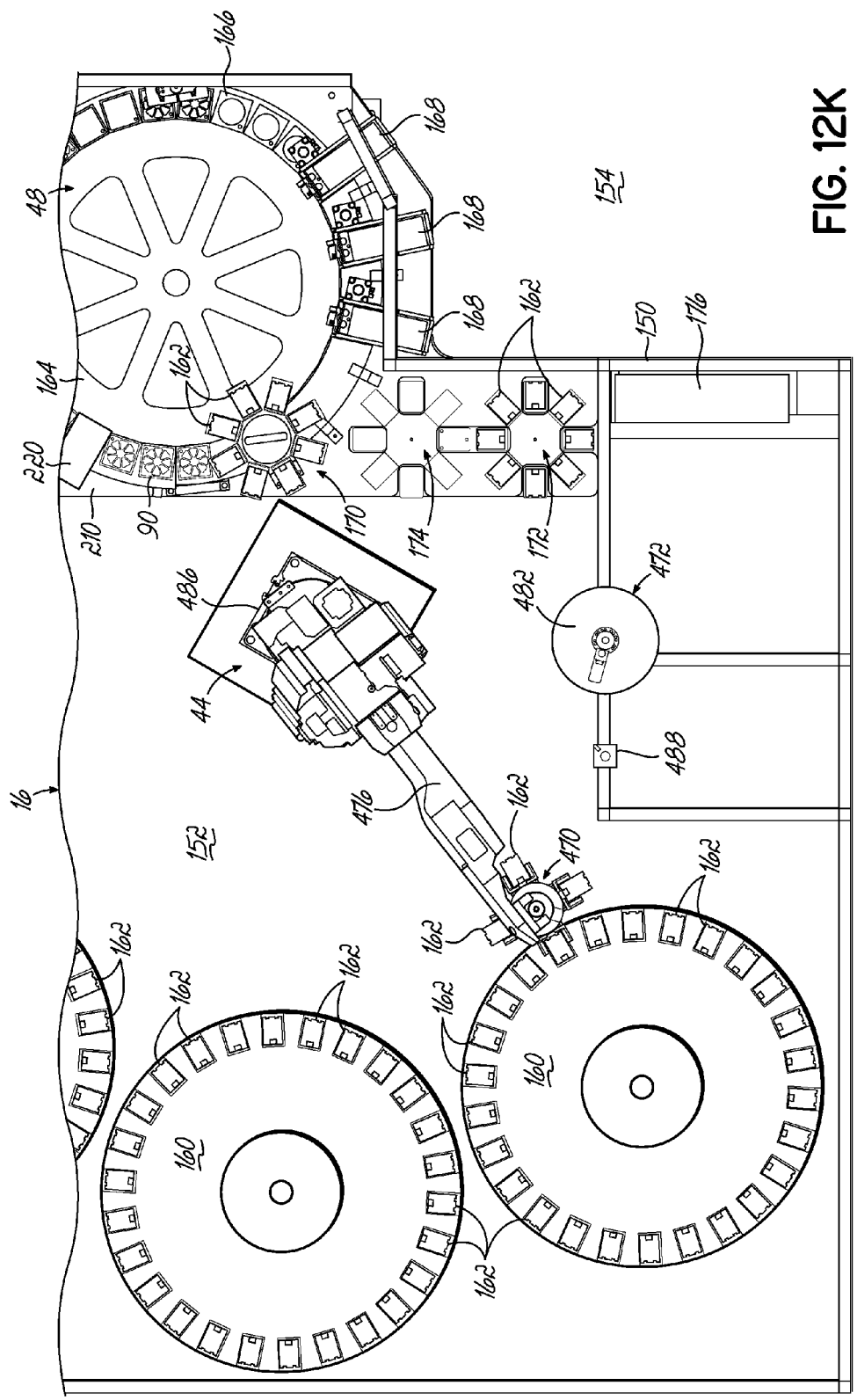
FIG. 12K is a top view similar to FIG. 12J, showing a further operational state of the station in which the first robot is replacing the used cassettes back into the storage carousels with the first gripping head.

Meanwhile, the moveable platens 452 at both the loading staging table 172 and at the unloading staging table 174 are moved to the raised position previously described. The first robot 44 then moves the other four cassettes 162 retrieved from the storage carousels 160 and drops them onto the moveable platens 452 of the loading staging table 172 as shown in FIG. 12I. With the moveable platens 452 in the raised position, the first gripping head 470 does not interfere with the first four cassettes 162 already in position on the stationary platens 450. The first robot 44 then moves the first gripping head 470 to the unloading staging table 174 as shown in FIG. 12J to pick up the first four cassettes 162 to be returned to the storage carousels 160. These first four cassettes 162 are located on the moveable platens 452, which are in the raised position as previously described. The first robot 44 then returns those first four cassettes 162 to the storage carousels 160 (while the moveable platens 452 at the loading and unloading staging tables 172, 174 return to the lowered position) and returns to the unloading staging table 174 to pick up the last four cassettes 162. As previously described and as shown in FIG. 12K, the first robot 44 then moves the first gripping head 470 to replace these last four cassettes 162 to the storage carousels 160. Once these last four cassettes 162 are returned, the feeder base 170 and staging tables 172, 174 are back to the initial state shown in FIG. 12A, with cassettes 162 being currently used on the feeder base 170 and the next batch of cassettes 162 ready on the loading staging table 172. The first robot 44 may then return to the storage location 488 to switch back to engagement with the second gripping head 472 as previously described. Each of these steps shown in FIGS. 12E through 12K occurs while the feeder base 170 fills the next thirty blister packs 90 such that no substantial delay is required between batches of cassettes 162.

Figure 12L:
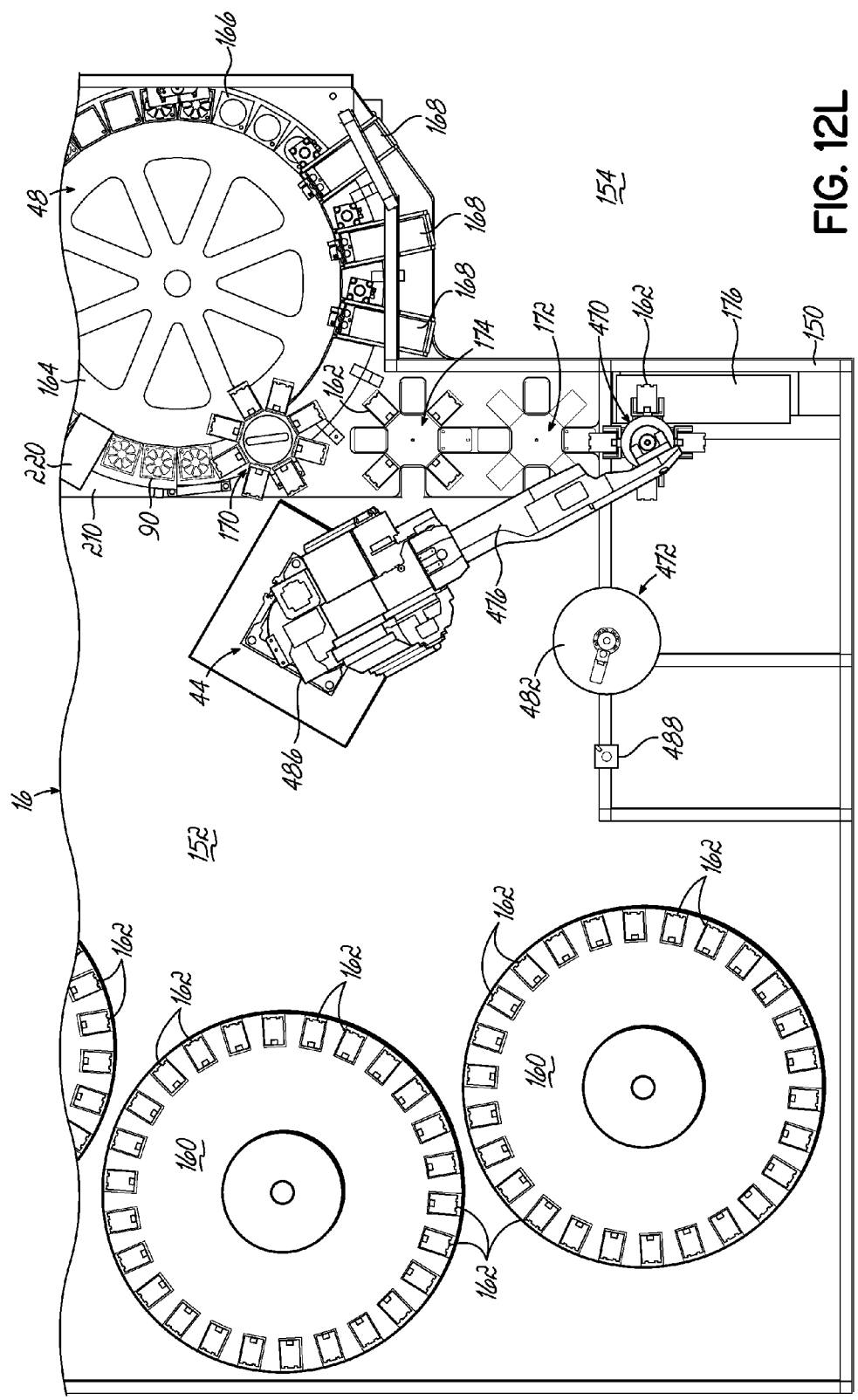
FIG. 12L is a top view similar to FIG. 12K, showing a further operational state of the station in which the first robot is placing a cassette requiring refill of stock into a replenishment window for manual restocking.

Also during this same time period, if any of the cassettes 162 need refilled with new bulk supply, the first robot 44 uses the first gripping head 470 to move these cassettes 162 from the unloading staging table 174 to the refill window 176 as shown in FIG. 12L before replacing the first gripping head 470 with the second gripping head 472 again. The operators 156 may then retrieve these cassettes 162 and have them refilled. If any cassettes 162 are refilled and replaced in the refill window 176, the first robot 44 moves these refilled cassettes 162 back to the storage carousels 160 before replacing the first gripping head 470 with the second gripping head 472. The previous process of operational steps from FIGS. 12E through 12K is configured to be completed with enough time to also allow for additional movements to and from the refill window 176 before the first robot 44 is required to restart the process as shown in FIG. 12A. This process of operation for the first robot 44 enables all functions relating to the cassettes 162 to be performed within the robotic work zone 152 simultaneously with the operation of the turntable assembly 48 as previously described. It will be understood that the particular ordering of certain steps described above may be reordered or otherwise modified without departing from the scope of the embodiments of the present invention. For example, if a cassette 162 on the feeder base 170 is to be reused in one of the next two batches of cassettes 162, the first robot 44 may operate to leave that cassette 162 on the feeder base 170 or move the cassette 162 between the unloading staging table 174 and the loading staging table 172 without returning these reused cassettes 162 to the storage carousels 160 each cycle.

Figure 13:
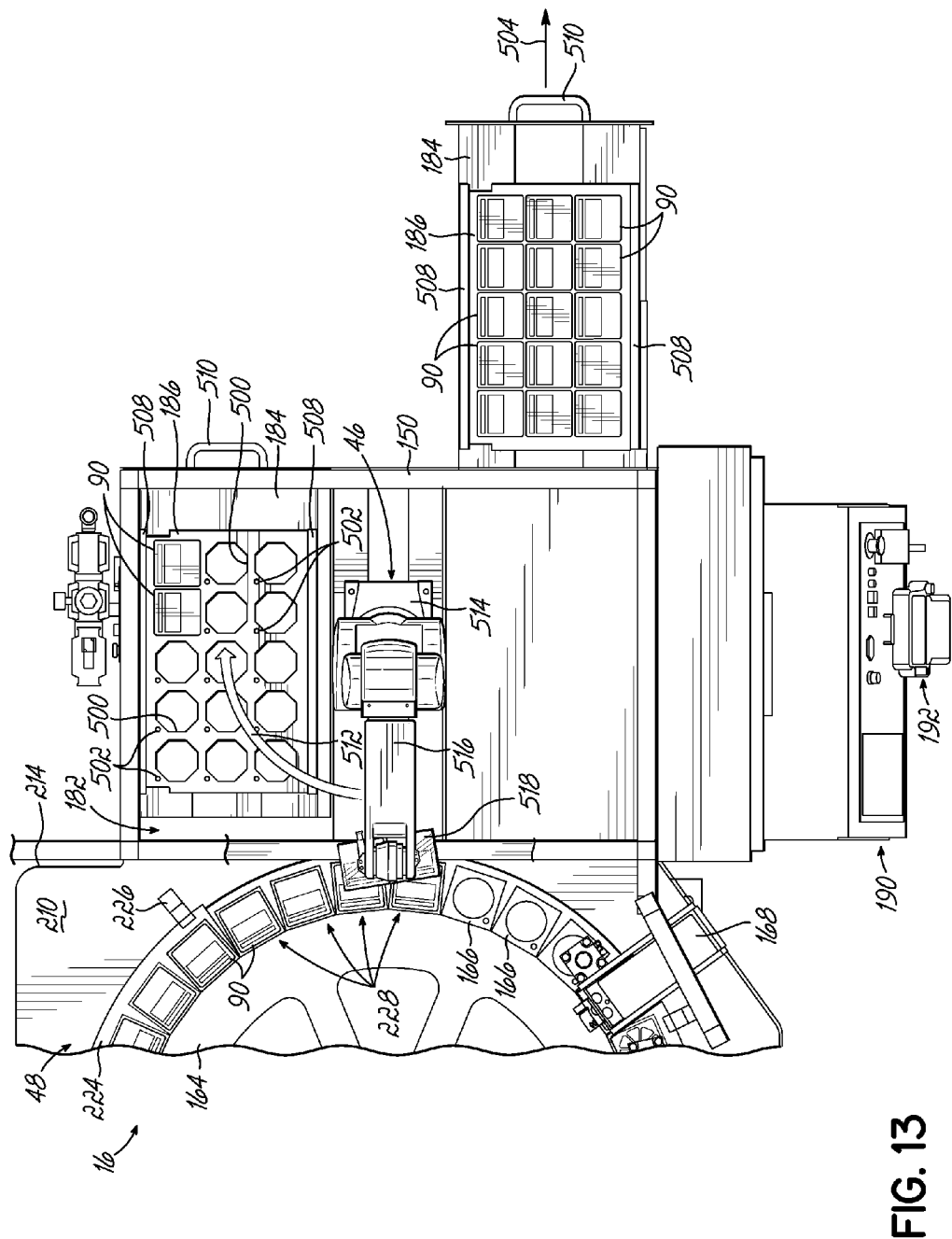
FIG. 13 is a top view of another portion of the automated packaging station of FIG. 4, showing a second robot moving filled medication packagings from the turntable assembly to a first collection tray on a tray table while a second collection tray filled with the medication packagings is removed from the tray table.

With reference to FIGS. 13 through 15B, the operation of the second robot 46 at the blister unloading station 182 is shown in further detail. As described above, the blister unloading station 182 is located along the second platform side 214 of the turntable platform 210 and is positioned at about the 5 o'clock to 7 o'clock position on the rotary dial 164 relative to the feeder base 170. As shown in FIG. 13, the elongate cover 224 terminates at a location so as to leave up to five or six stepwise locations of nests 166 on the rotary dial 164 that may be accessed by the second robot 46. Accordingly, the second robot 46 can move to pick up blister packs 90 from any of these blister unloading locations 228 as they are available, which provides some flexibility for allowing minor delays in the operation of the second robot 46. Similar to the area of operation for the first robot 44, the blister unloading station 182 defines an area of operation for the second robot 46 that is enclosed by the barrier wall 150. However, as described in detail below, the operators 156 have access to the blister unloading station via the drawers 184.

Figure 14:
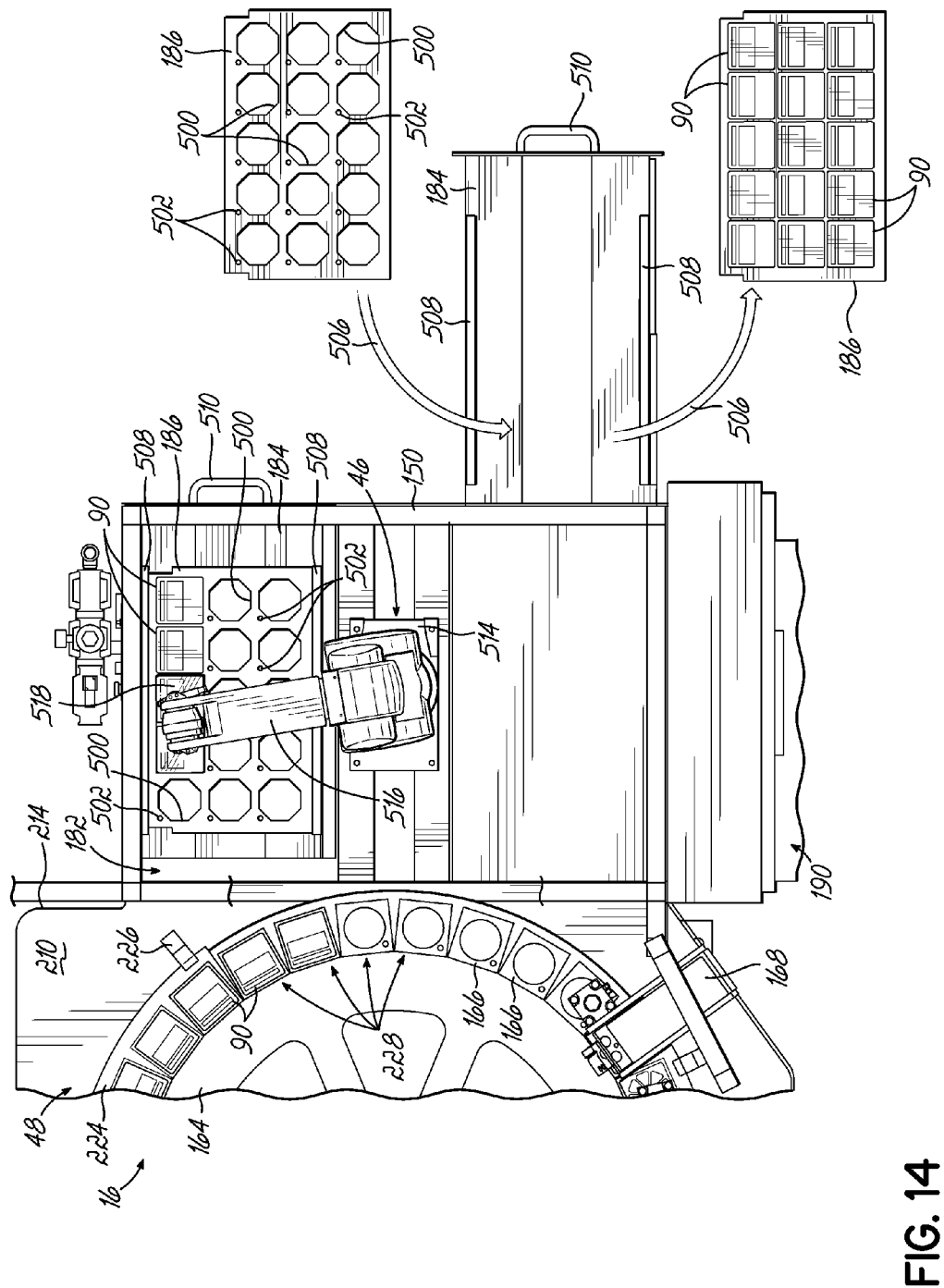
FIG. 14 is a top view similar to FIG. 13, showing the replacement of the second collection tray filled with the medication packagings with another empty collection tray.

With particular reference to FIGS. 13 and 14, the second robot 46 operates to move filled and covered blister packs 90 from the nests 166 on the rotary dial 164 to one of two trays 186 that are contained in drawers 184 on either side of the second robot 46. The particular gripping operation of the second robot 46 is described in further detail below. The trays 186 are similar to those used during a manual filling operation for the blister packs 90 and include fifteen shaped cavities 500 configured to receive the downwardly projecting compartments 94 of a blister pack 90. Thus, in the exemplary embodiment, the shaped cavities 500 define a generally octagonal shape to accommodate the octagonal array of compartments 94 on a blister pack 90. The tray 186 also includes an indexing slot 502 adjacent to each of the shaped cavities 500, the indexing slot 502 configured to receive the indexing features 106 of the blister packs 90. To this end, the second robot 46 operates to position the filled blister packs 90 in a consistent orientation and location within each of the shaped cavities 500 on the tray 186. Each tray 186 also includes identifying indicia (not shown) such as a tray barcode that may be scanned by the operators 156 to enable association of the tray 186 with the particular order of blister packs 90 being filled. This tray barcode enables downstream tracking of the trays 186 as the blister packs 90 continue to downstream verification and packaging processes outside the scope of the embodiments of the invention.

As shown in FIGS. 13 and 14, two drawers 184 are provided at the blister unloading station 182 so that the second robot 46 can continue filling one tray 186 while the other tray 186 is replaced by an operator 156. Once a tray 186 is filled with the filled blister packs 90 as shown in the bottom-most drawer 184 of FIG. 13, that drawer 184 may be pulled out of the robotic work zone 152 through the barrier wall 150 into the operator work zone 154 as shown by arrow 504. Once the drawer 184 is fully opened, the operator 156 removes the filled tray 186 and replaces it with an empty tray 186 as shown by arrows 506 in FIG. 14. The filled tray 186 is positioned on a cart or some other storage device configured to move a series of filled trays 186 to the aforementioned downstream processing locations. To ensure a generally consistent positioning of the trays 186, each drawer 184 includes alignment rails 508 that the tray 186 should be inserted between and aligned with by the operator 156. This alignment of the trays 186 allows the second robot 46 to accurately deposit the filled blister packs 90 into the shaped cavities 500. Although not shown in the Figures, the drawers 184 may also include a locking mechanism (not shown) for selectively locking the trays 186 in position in the drawers 184. With the new empty tray 186 in position on the drawer 184, the operator then pushes the drawer 184 back into the robotic work zone 152 and into the blister unloading station 182 using a handle 510 on the drawer 184. It will be understood that the machine controller 42 may be connected to sensors (not shown) adjacent the drawers 184 that verify when the drawer 184 is inserted back into the blister unloading station 182 with an empty tray 186, which effectively prevents the second robot 46 from depositing filled blister packs 90 onto a filled tray 186 or onto a pulled-out drawer 184 (the filling process will be delayed if necessary to accommodate the operator 156).

As the operator 156 works to replace the filled tray 186 as described above, the second robot 46 continues to operate to fill the other tray 186 in the uppermost drawer 184 shown in FIGS. 13 and 14. In this regard, the second robot 46 applies a suction force to grab the filled blister packs 90 from the nests 166 and moves the filled blister packs 90 as shown by arrow 512 in FIG. 13 to corresponding empty shaped cavities 500 on the tray 186. To enable this movement, the second robot 46 includes a base support 514 located between the two drawers 186 when the drawers 186 are inserted into the blister unloading station 182, a terminal arm 516 coupled to the base support 514 and configured for three dimensional articulation about the base support 514, and a gripping head 518 coupled to the terminal arm 516. Unlike the first robot 44, the second robot 46 needs to only reach a limited area within the robotic work zone 152 and uses only one gripping head 518. However, it will be understood that the second robot 46 could be reconfigured to work with multiple gripping heads or over a higher number of drawers 186 in alternative embodiments consistent with the invention. It will further be appreciated that the blister unloading station 182 may be reconfigured in other alternative embodiments with a completely automated tray system that automatically moves new trays 186 into position to be filled and then conveys those filled trays 186 to a cart for downstream processing.

Figure 15A:
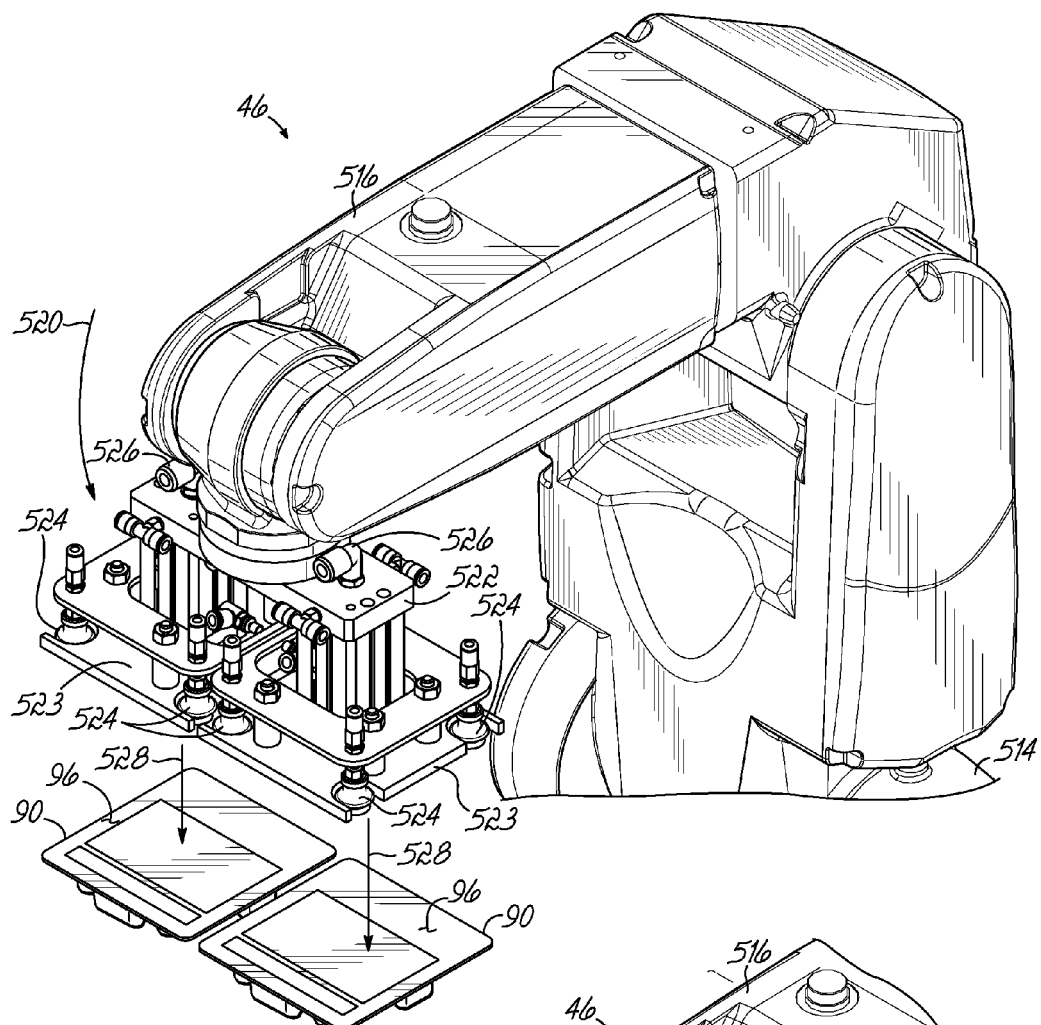
FIG. 15A is a perspective view of the second robot of FIG. 13, with a gripping head of the second robot positioned above two medication packagings on the turntable assembly.
Figure 15B:
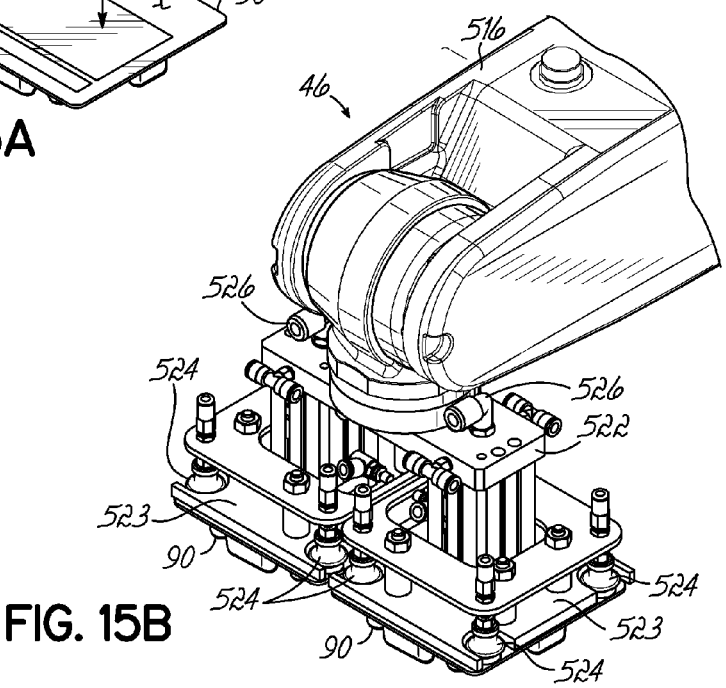
FIG. 15B is a perspective view of the second robot of FIG. 15A, showing the gripping head engaged with the two medication packagings.

With reference to FIGS. 15A and 15B, the second robot 46 is shown in further detail. More specifically, the gripping head 518 of the second robot 46 is illustrated moving to a position over two filled and covered blister packs 90, as indicated by arrow 520. The gripping head 518 of the exemplary embodiment includes a main platform 522, a pair of intermediate platforms 523 extending downwardly from the main platform 522, and a plurality of, for example, four vacuum ports 524 extending downwardly adjacent the corners of the intermediate platforms 523. It will be understood that the main platform 522 and intermediate platforms 523 may be formed as one unitary platform in other embodiments of the invention. The gripping head 518 also includes inlet ports 526 located at the main platform 522 and operatively connected to the corresponding sets of vacuum ports 524 and valving (not shown) for controlling a supply of pressurized air or vacuum to the sets of vacuum ports 524. In the exemplary embodiment, each inlet port 526 is effectively supplied with vacuum pressure by an independent source of pressurized air or vacuum. From the position shown in FIG. 15A, the terminal arm 516 moves the gripping head 518 downwardly as shown by arrows 528 so that the vacuum ports 524 engage the covers 96 at the corner regions 104 of the blister packs 90. The source of vacuum pressure from the inlet ports 526 is then applied to cause the vacuum ports 524 to hold each of the blister packs 90 simultaneously. It will be understood that the vacuum pressure applied through the vacuum ports 524 is sufficient to pick up and hold the filled blister packs 90 without being so strong as to tear off the cover 96 from the blister packs 90. With the blister packs 90 retained on the gripping head 518 as shown in FIG. 15B, the second robot 46 is ready to move the blister packs 90 to one of the trays 186 as previously described. It will be understood that the gripping head 518 can rotate to any orientation convenient for picking up two blister packs 90 and is also operable to pick up only one blister pack 90 as well by applying vacuum pressure from only one set of the vacuum ports 524 (such as when the fifteenth and final shaped cavity 500 on each tray 186 is to be filled).

Figure 16:
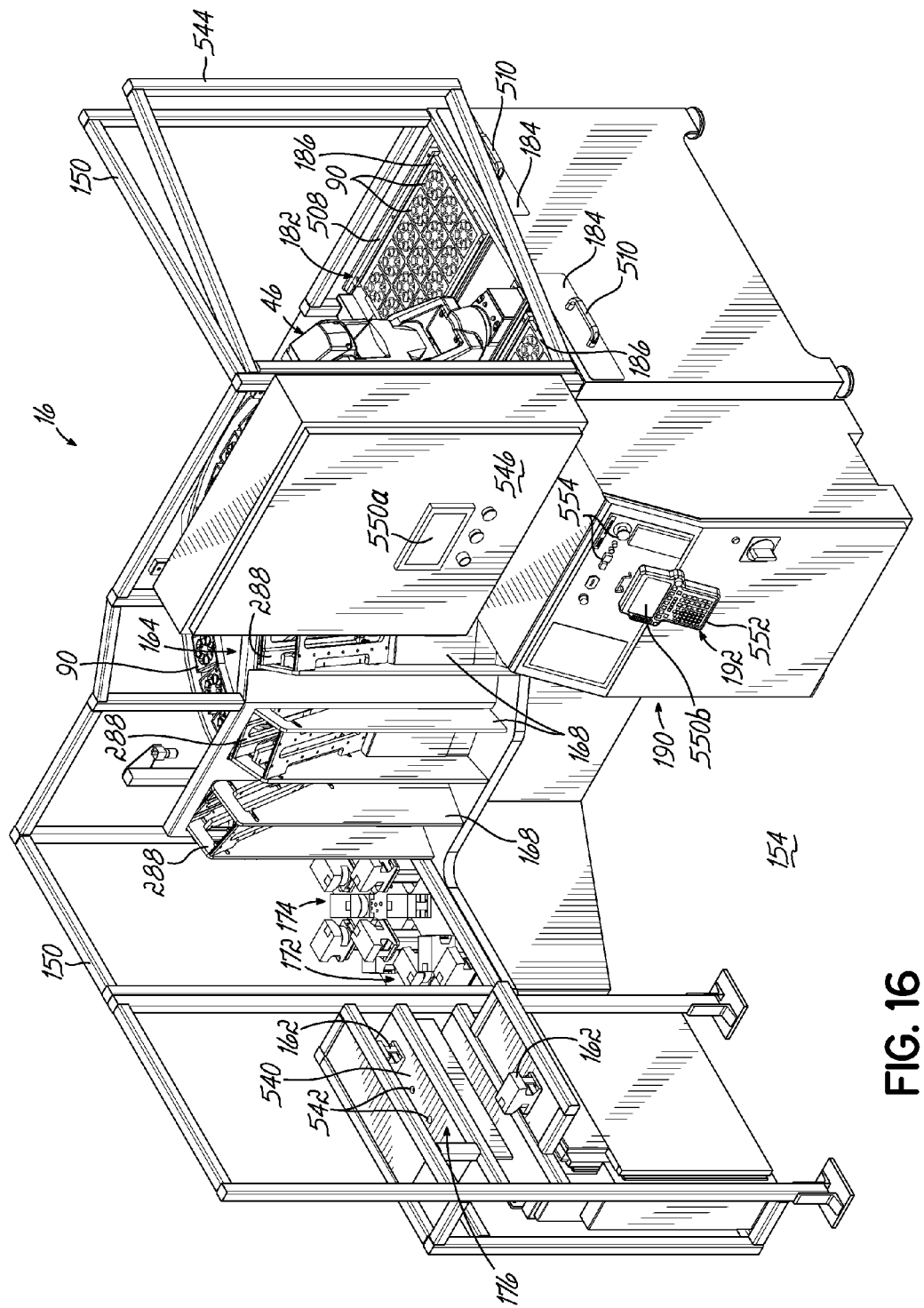
FIG. 16 is a perspective view of an operator portion of the automated packaging station of FIG. 4, the operator portion including a user interface and the replenishment window of FIG. 12L.

Now with reference to FIG. 16, the operator work zone 154 is shown in further detail. The operator work zone 154 provides access to each of the areas that the operators 156 need to interact with the previously-described machine elements held within the robotic work zone 152. To this end, the operator work zone 154 includes the refill window 176 through which cassettes 162 can be picked up and dropped off by the first robot 44 when those cassettes 162 are in need of replenishment of bulk supply. The refill window 176 may include a single opening 540 for both incoming and outgoing cassettes 162 in the barrier wall 150 as shown in FIG. 16. In this embodiment with a single opening 540, the opening 540 may include predetermined shelf locations indicated by the marks 542 shown in FIG. 16. These marks 542 allow an operator 156 to position a particular cassette 162 in a particular position so that the first robot 44 and the machine controller 42 know which medication is stored in that cassette 162 when it is moved back to the storage carousels 160. Consequently, even if multiple refilled cassettes 162 are to be placed in the refill window 176, the automated packaging station 16 retains the proper information on what medications are in each cassette 162 located within the robotic work zone 152. It will be understood that the refill window 176 may be modified in other embodiments, such as to include multiple openings through the barrier wall 150, without departing from the scope of the embodiments of the invention.

As previously described, each of the three packaging magazines 168 also extends through the barrier wall 150 into the operator work zone 154. Thus, the operators 156 have access to the open upper channel end 288 of the magazine channel 286 such that new stacks of empty blister packs 90 may be positioned in the packaging magazines 168 when necessary. The elongate apertures 294 also face towards the operator work zone 154 so that the operators 156 can periodically monitor the supply of empty blister packs 90 in each of the packaging magazines 168. The operator work zone 154 also includes access to the drawers 184 of the blister unloading station 182. As previously described, the operators 156 retrieve filled trays 186 of filled blister packs 90 from the drawers 184 and replace those filled trays 186 with empty trays 186 configured to receive the next batch of filled blister packs 90. The barrier wall 150 may include a pivotal window 544 above the drawers 184 which is closed during normal operation of the automated packaging station 16. However, this pivotal window 544 may be opened to provide easy access to the blister unloading station 182, should that become necessary for any reason (jammed/misplaced blister packs 90 in a tray 186, for example).

The machine controller 42 of the automated packaging station 16 includes the workstation 190 which includes a controller box 546 located in the operator work zone 154 and on the opposite side of the barrier wall 150 from the blister unloading station 182. The controller box 546 includes the hardware previously described in association with the machine controller 42. To this end, the controller box 546 includes the user interface 192 including an upper display screen 550a, a lower display screen 550b, a keypad 552 adjacent the lower display screen 550b for manually entering information into the control system, and a plurality of alternative control/input buttons 554 located generally between the upper and lower display screens 550a, 550b. The upper display screen 550a is configured to display a list of orders currently assigned to be filled by the automated packaging station 16, as received from the centrally located controller 12 that manages orders for multiple packaging stations 14, 16. The lower display screen 550b is configured to show interactive information regarding the control and operations of the machine elements and cassettes 162 contained within the robotic work zone 152. Thus, any operating status updates or warnings pertaining to elements such as the first and second robots 44, 46 will be provided at the lower display screen 550b. The operators 156 may monitor or review any information that is monitored by the machine controller 42 at the lower display screen 550b. The operators 156 may input commands through the keypad 552 or the alternative control/input buttons 554 to provide any additional information (e.g., which refilled cassettes 162 are placed in the refill window 176) or operating instructions to the automated elements of the automated packaging station 16. For example, one of the alternative control/input buttons 554 may be an emergency shutdown switch that immediately stops all automated actions within the robotic work zone 152 in the event of an accident or other fault observed by the operators 156.

Consequently, the previously-described arrangement of elements within the robotic work zone 152 and within the operator work zone 154 allows operators 156 to safely monitor a filling process that is completely automated with respect to the cassettes 162 holding the medications and the blister packs 90 being filled with medications for particular patients. This filling process enables a high level of speed and accuracy, with minimal human verification. Moreover, the operators 156 are only required to switch out the trays 186, restock the empty blister packs 90 in the packaging magazines 168 when necessary, and send empty or defective cassettes 162 to be refilled or repaired as necessary. Thus, any delays caused by human filling or errors are reduced to a minimum when using the automated packaging station 16. In the exemplary embodiment, for example, a full month's supply of 120 blister packs 90 for a patient can be filled in about five minutes total when using the automated packaging station 16. The methods and processes implemented by the drug packaging system 10 and by the automated packaging station 16 are described in greater detail below with reference to a number of operational flowcharts shown in the figures. Except when otherwise discussed, the following methods and processes are implemented by the exemplary embodiment of the drug packaging system 10 described in detail above.

In this regard, some embodiments of the invention may include systems and methods for dynamically sorting one or more prescriptions into a patient specific pharmacy order. The patient specific pharmacy order may include one or more patient specific drug packages to be filled with one or more drugs indicated by the one or more drug prescriptions. In some embodiments consistent with the invention, each prescription may be analyzed, and packaging instructions corresponding to the appropriate dosage of each drug to be placed in each patient specific drug package (e.g., the blister packs 90) of the patient specific pharmacy order may be generated. For example, the patient specific drug package may correspond to a time of day the patient should take the drug including morning, lunchtime, evening, bedtime, etc. In addition, the patient specific drug package may correspond to a particular day of the week, or a specific date (e.g. Jan. 1, 2012), such that the analysis and dynamic sorting may generate packaging instructions corresponding to one or more patient specific drug packages that may be specific to a time of day, day of the week, and/or a specific calendar date.

In these embodiments, one or more prescriptions of a drug prescription order may be loaded, and each prescription may include prescription data which may indicate the patient and/or a unique patient identifier, the drug type, dosage amount, the dosing instructions, and/or patient dosage preferences. In some embodiments, the one or more loaded prescriptions may be analyzed to determine the patient associated with each loaded prescription, the drug type of each prescription, the dosage amount of each prescription, and/or the dosing instructions for each prescription.

In some embodiments, analyzing the prescription data of each prescription associated with a patient prescription group may include analyzing the indicated drug type of each prescription associated with a patient prescription group to determine drug contra-indications for one or more prescriptions associated with the patient prescription group. Moreover, generating patient specific drug packaging data for the patient associated with the patient prescription group may be based at least in part on the determined drug contra-indications.

In some embodiments, analyzing the prescription data of each prescription associated with a patient prescription group may include analyzing the indicated dosage amount of each prescription associated with a patient prescription group to determine the prescribed dosage amount of each prescription associated with the patient prescription group. Furthermore, generating patient specific drug packaging data for the patient associated with the patient prescription group may be based at least in part on the determined prescribed dosage amount of each prescription.

In some embodiments, analyzing the prescription data of each prescription associated with a patient prescription group may include analyzing the indicated dosing instructions of each prescription associated with a patient prescription group to determine the prescribed dosing instructions of each prescription associated with the patient prescription group. In addition, generating patient specific drug packaging data for the patient associated with the analyzed patient prescription group may be based at least in part on the determined prescribed dosage amount of each prescription.

In some embodiments, analyzing the prescription data of each prescription associated with a patient prescription group may include analyzing the indicated patient dosage preferences of each prescription associated with a patient prescription group to determine the patient preferences regarding one or more prescriptions of the patient prescription group. Furthermore, generating patient specific drug packaging data for the patient associated with the patient prescription group may be based at least in part on the indicated patient dosage preferences of each prescription.

In some embodiments, packaging instructions corresponding to each patient specific drug package of a patient specific pharmacy order may be generated based at least in part on the patient specific packaging data. The packaging instructions may also be referred to as filling instructions herein. In some embodiments, the packaging instructions may include program code executable by a control system of a drug packaging system such that the control system may direct and/or operate the drug packaging system to distribute prescribed dosages of one or more drugs into one or more patient specific drug packages, such that a patient specific pharmacy order may be filled. In some embodiments, the packaging instructions may correspond to a manual packaging station 14. In other embodiments, the packaging instructions may correspond to an automated packaging station 16. As such, in some embodiments, the generated packaging instructions may be based at least in part on the type of packaging station 14, 16 that may be packaging the patient specific drug packages of the patient specific pharmacy order.

FIGS. 17 through 36 provide sequences of operations that may be performed by some embodiments consistent with the invention. Moreover, embodiments of the invention provided as sequences of operations for example, in FIGS. 17 through 36 may be embodied in program code resident in various memory 62 and/or storage devices 74 and may be configured to be executed by one or more processors 60 of a drug packaging system 10 consistent with some embodiments of the system. In addition, while the invention has been illustrated by a description of various embodiments and while these embodiments have been described in considerable detail, the applicant does not intend to restrict or in any way limit the scope of the appended claims to such detail. For example, the blocks of any of the flowcharts may be re-ordered, processed serially and/or processed concurrently without departing from the scope of the invention. Moreover, any of the flowcharts may include more or fewer blocks than those illustrated consistent with embodiments of the invention.

While the invention has been and hereinafter will be described in the context of fully functioning systems, those skilled in the art will appreciate that the various embodiments of the invention are capable of being distributed as a program product in a variety of forms, and that the invention applies equally regardless of the particular type of computer readable media used to actually carry out the distribution. Examples of computer readable media include, for example, non-transitory recordable type media such as volatile and nonvolatile memory devices, floppy and other removable disks, hard disk drives, USB drives, optical disks (e.g. CD-ROM's, DVD's, Blu-Ray discs, etc.), among others.

Figure 17:
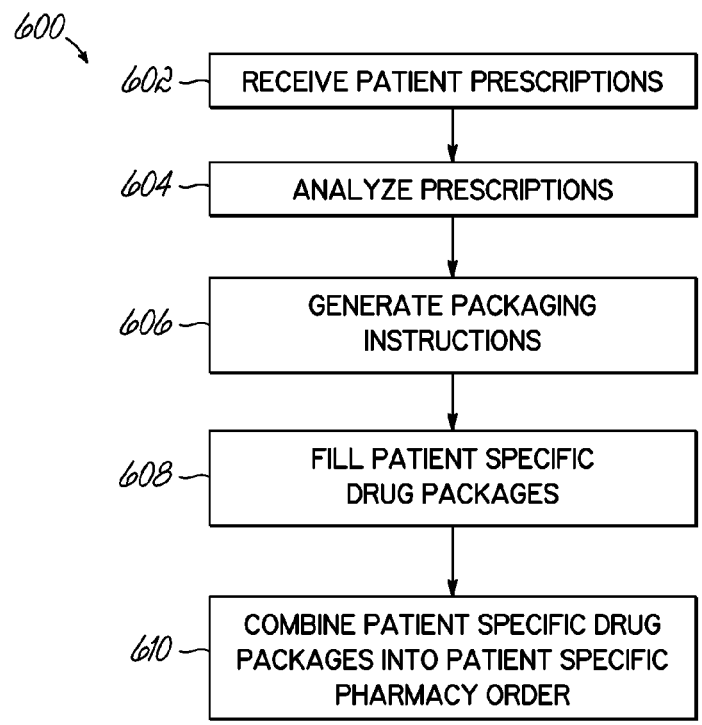
FIG. 17 is a flowchart of sequences of operations that may be performed by one or more processors of the drug packaging system of FIG. 1.

Referring to FIG. 17, flowchart 600 provides a sequence of operations that may be performed by some embodiments of a drug packaging system 10 consistent with the invention. The drug packaging system 10 receives one or more patient prescriptions (block 602). For example, referring to FIG. 1, the drug packaging system 10 may receive the one or more patient prescriptions from the input devices 72, where the input devices 72 may include a barcode scanner and the patient prescriptions may be in the format of scannable barcodes. The drug packaging system 10 may receive the one or more patient prescriptions from the input devices 72, where the input devices may include a keyboard and/or mouse, and a user may input one or more prescriptions utilizing an interface configured to communicate prescriptions and prescription data to the drug packaging system 10. In some embodiments, a drug packaging system 10 may receive one or more patient prescriptions from a remote terminal 82 configured to communicate prescriptions and prescription data to the drug packaging system 10 via the network 20. In addition, the drug packaging system 10 may be configured to receive one or more prescriptions from external resources 80, where the external resources 80 may be configured to communicate prescriptions and prescription data to the drug packaging system 10 via the network 20.

The drug packaging system analyzes the received prescriptions (block 604), and the drug packaging system generates packaging instructions based at least in part on the analyzed prescriptions (block 606). As discussed previously, the packaging instructions may indicate the specific drugs and the dosage of each drug to be placed in a patient specific drug package. For example, referring to FIG. 2A, the packaging instructions may indicate the drug and dosage of each drug to be placed in a particular compartment 94 of blister pack 90. Moreover the generated packaging instructions may include data indicating the prescribed combination of the patient specific drug packages such that a patient specific pharmacy order may be filled. The drug packaging system 10 may then fill the patient specific drug packages based on the generated packaging instructions (block 608).

The drug packaging system 10 may combine the filled patient specific drug packages into a patient specific pharmacy order based at least in part on the generated packaging instructions (block 610). For example, referring to FIGS. 1 through 3, drug packaging system 10 may receive one or more patient prescriptions, analyze the received prescriptions, and generate packaging instructions, where the packaging instructions indicate each drug and the dosage of each drug to be placed in each compartment 94 of the blister pack 90. After filling the compartments 94 of one or more blister packs 90 based on the generated packaging instructions, the drug packaging system 10 may combine the blister packs 90 based at least in part on the generated packaging instructions to complete a patient specific pharmacy order similar to the patient specific pharmacy order shown in FIG. 3.

Figure 18:
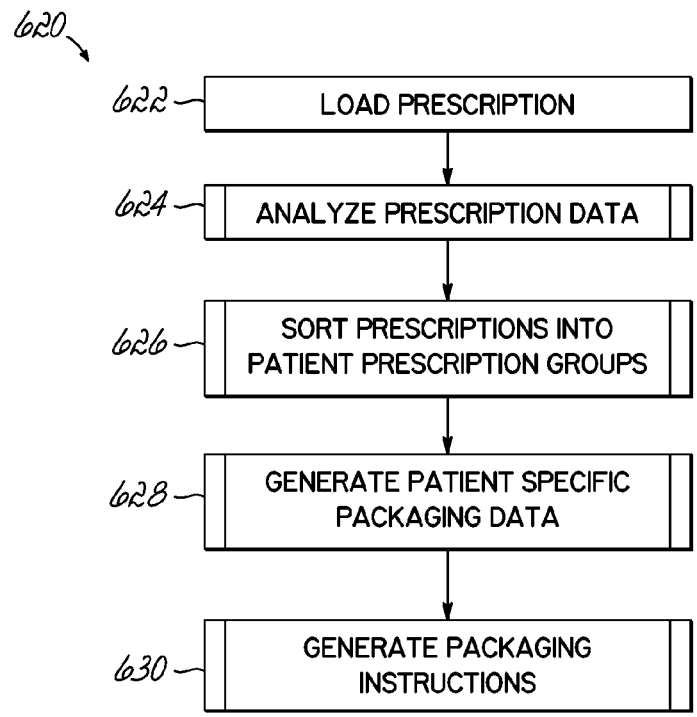
FIG. 18 is a flowchart of sequences of operations that may be performed by the drug packaging system of FIG. 1 to generate packaging instructions from prescription data.

In FIG. 18, flowchart 620 illustrates a sequence of operations that may be performed by a drug packaging system 10 consistent with some embodiments of the invention. The drug packaging system 10 loads one or more patient prescriptions (block 622). As disclosed above, the drug packaging system 10 may receive one or more patient prescriptions from a plurality of sources 72, 80, 82, and the drug packaging system 10 may load the prescriptions into memory 62 and/or storage locations 74 operatively connected to the drug packaging system 10. For example, referring to FIG. 1, the drug packaging system 10 may load the prescriptions into data structure 66, local storage 74, memory and/or data structures associated with external resources 80, and/or memory and/or data structures associated with remote terminals 82.

As discussed previously, the prescriptions may include prescription data, where the prescription data may indicate the patient and/or a unique patient identifier, the drug type, dosage amount, the dosing instructions, and/or patient dosage preferences. The drug packaging system 10 analyzes the prescription data of each prescription (block 624). The drug packaging system 10 sorts the prescriptions into patient prescription groups based at least in part on the analyzed prescription data of each prescription (block 626). Sorting the prescriptions into patient prescription groups may be utilized such that the drug packaging system 10 may receive and/or load prescriptions corresponding to a plurality of patients.

The drug packaging system 10 may generate patient specific packaging data based at least in part on the analyzed prescription data of each prescription associated with a patient prescription group (block 628). For example, in some embodiments patient specific packaging data may be based at least in part on a contra-indication between two drugs included in prescriptions associated with a patient prescription group. Moreover, in some embodiments, patient specific packaging data may be based at least in part on patient dosage preferences indicated in the prescription data or other sources, including for example, an external server including patient preference data associated with a patient. For example, prescription data for one or more prescriptions associated with a patient prescription group may indicate that the patient prefers or the prescribing physician recommends taking two lower dosage pills of a particular drug as opposed to one high dosage pill of the same drug, and as such, the generated patient specific packaging data may be based at least in part on the indicated preference.

The drug packaging system 10 may generate packaging instructions based at least in part on the generated patient specific packaging data (block 630). Referring to FIG. 1, the drug packaging system 10 may generate packaging instructions for manual packaging station 14 and/or automated packaging station 16. As such, in some embodiments, the packaging instructions may be based at least in part on the type of packaging station 14, 16 that will fill the patient specific drug packages of the patient specific pharmacy order.

Figure 19:
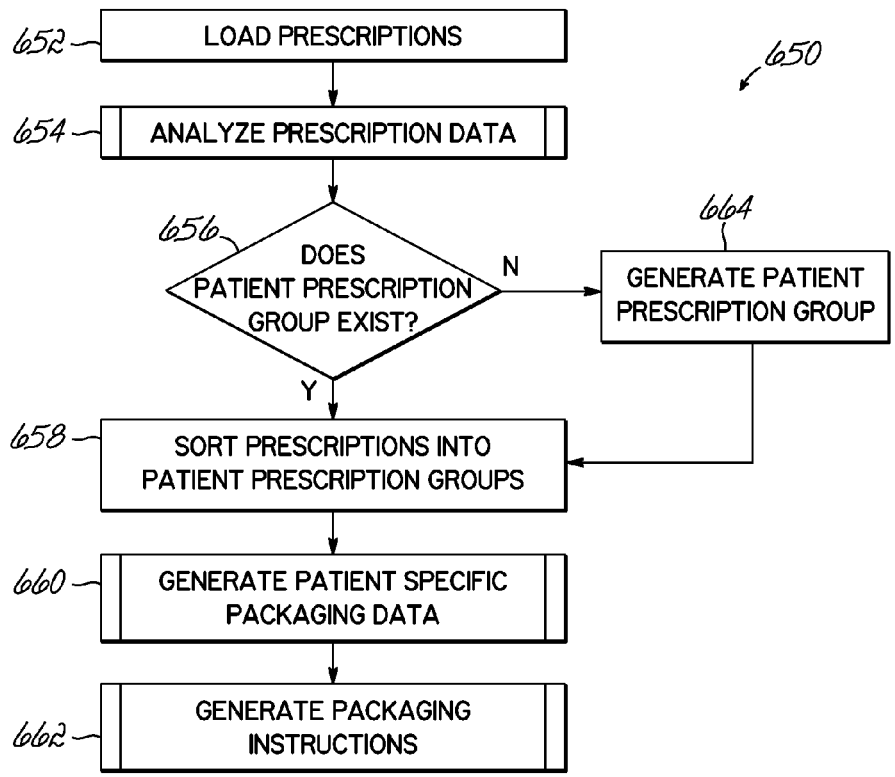
FIG. 19 is a flowchart of sequences of operations that may be performed by the drug packaging system of FIG. 1 to determine if a new prescription applies to a current patient or a new patient.

Referring now to FIG. 19, flowchart 650 illustrates a sequence of operations that may be performed by the drug packaging system 10 consistent with some embodiments of the invention. The drug packaging system 10 may load the prescriptions (block 652), and analyze the prescription data of each prescription (block 654). The drug packaging system 10 may determine whether a patient prescription group associated with a patient identified in the prescription data of each prescription exists in the drug packaging system (block 656). The patient prescription groups and associated prescriptions may be stored in memory 62 and/or storage locations 74 operatively connected to the drug packaging system 10. As such, the drug packaging system 10 may thereby operate to update a previously generated patient prescription group with new prescriptions loaded into the drug packaging system 10.

In response to determining that the patient prescription group does exist in the memory and/or storage location, the drug packaging system 10 may sort prescriptions into the patient prescription group associated with the patient identified in the prescription data of each prescription (block 658). The drug packaging system 10 may generate patient specific packaging data based at least in part on the analyzed prescription data of each prescription associated with a patient prescription group (block 660), and the drug packaging system 10 may generate packaging instructions based at least in part on the patient specific packaging data (block 662). In response to determining that the patient prescription group does not exist in the memory and/or storage location, the drug packaging system 10 may generate a patient prescription group associated with a patient identified in prescription data of a loaded prescription (block 664).

Figure 20:
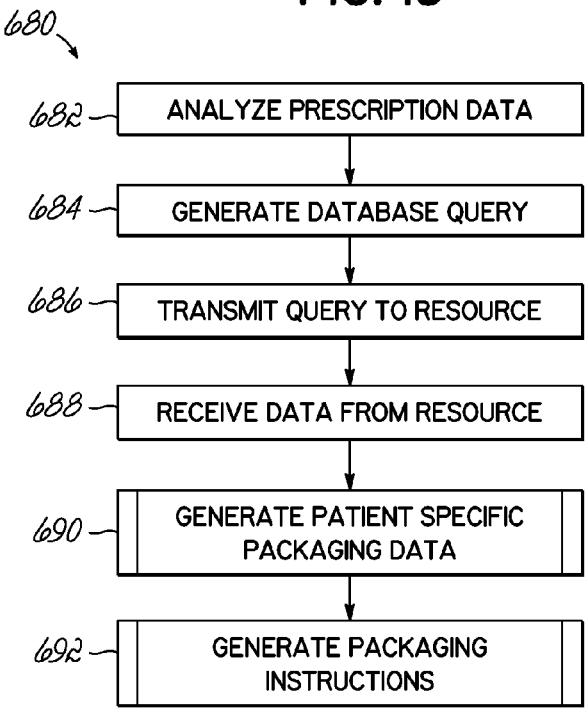
FIG. 20 is a flowchart of sequences of operations that may be performed by the drug packaging system of FIG. 1 to analyze prescription data.

Referring to FIG. 20, flowchart 680 illustrates a sequence of operations that may be performed by the drug packaging system 10. The drug packaging system 10 may analyze prescription data of one or more prescriptions (block 682), and the drug packaging system 10 may generate a database query based at least in part on the analyzed prescription data (block 684). For example, referring to FIG. 1, the analyzed prescription data may indicate the drug type of one or more prescriptions for a patient, and drug packaging system 10 may generate a database query based on the indicated drug types. The generated query may be transmitted to a resource (block 686), for example external resources 80, remote terminals 82, and/or local storage 74. The drug packaging system 10 may receive data from the queried resource (block 688), for example, the resource may return drug contra-indication data, patient preference data, patient medical data, etc. Based at least in part on the data received from the queried resource, the drug packaging system 10 may generate patient specific packaging data (block 690), and the drug packaging system 10 may generate packaging instructions based at least in part on the generated patient specific packaging data (block 692).

Figure 21A:
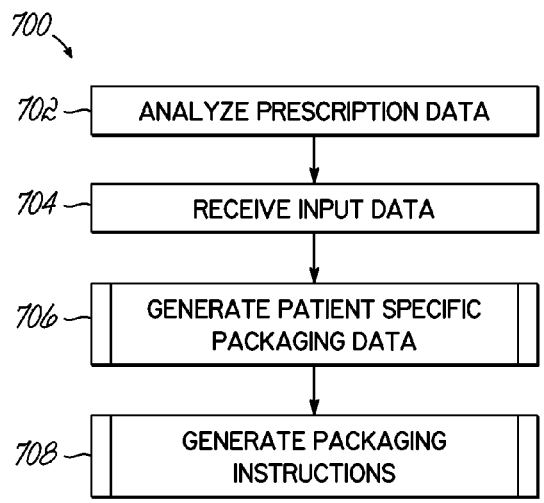
FIG. 21A is a flowchart of sequences of operations that may be performed by the drug packaging system of FIG. 1 to generate packaging instructions from other input data.

In some embodiments, the drug packaging system 10 may receive input data from one or more sources, and the patient specific drug packages (e.g., blister packs 90) may be filled with one or more drugs of prescribed dosages based at least in part on the received input data. Referring to FIG. 21A, flowchart 700 illustrates a sequence of operations that may be performed by the drug packaging system 10. In this regard, the drug packaging system 10 may analyze prescription data of each prescription for a patient (block 702). The drug packaging system 10 may receive input data from one or more sources (block 704). For example, referring to FIG. 1, drug packaging system 10 may receive input data from input devices 72, remote terminals 82, and/or external resources 80. Based at least in part on the received input data and/or the analyzed prescription data, the drug packaging system 10 may generate patient specific drug packaging data (block 706), and the drug packaging system 10 may generate packaging instructions based at least in part on the generated patient specific drug packaging data (block 708).

Figure 21B:
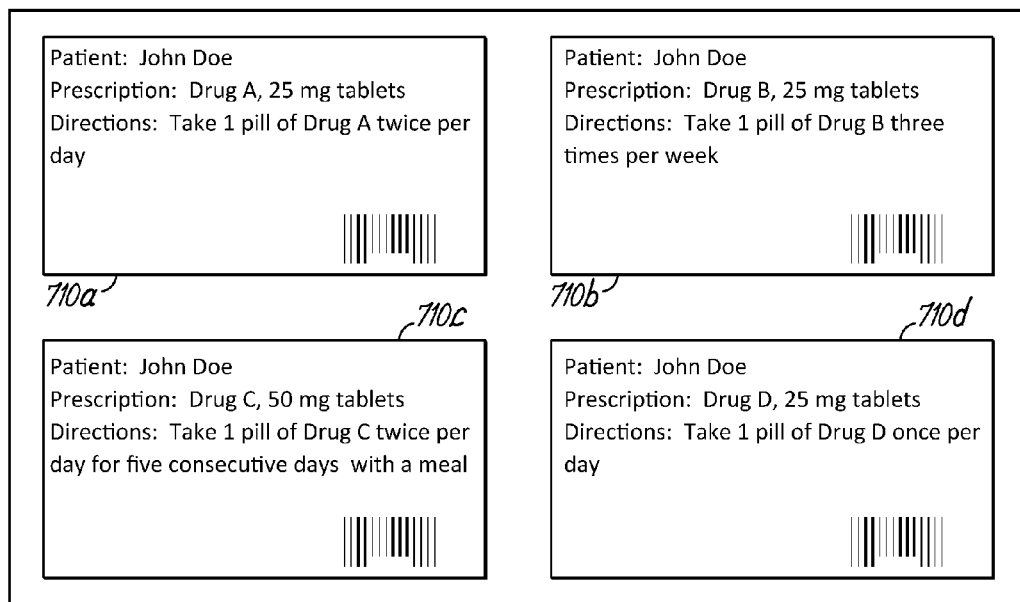
FIG. 21B is a schematic view of four prescriptions used in an exemplary operation of the drug packaging system of FIG. 1 to generate packaging instructions.

One simplified example of producing filling instructions from a series of prescriptions is shown schematically in FIGS. 21B through 21D. Referring now to FIG. 21B, four exemplary prescriptions 710a, 710b, 710c, 710d include prescription data comprising a patient name, drug type, dosing amount, and dosing instructions. Using embodiments consistent with the invention, the exemplary prescriptions 710a, 710b, 710c, 710d and the included prescription data may be analyzed and patient specific packaging data corresponding to the patient may be generated based at least in part on the drug type, dosing amount, and/or dosing instructions.

FIG. 21C provides an exemplary chart 712 which illustrates patient specific packaging data corresponding to the exemplary prescriptions 710a, 710b, 710c, 710d of FIG. 21B. As shown in FIG. 21C, patient specific packaging data may be generated by analyzing loaded prescriptions, where the patient specific packaging data indicates a patient specific drug package in which one or more different drugs are to be packaged. Chart 712 includes a plurality of blister packs 90, where each blister pack 90 includes a plurality of compartments 94. The compartments 94 are configured to hold one or more drugs that a patient is prescribed. Those skilled in the art will recognize that chart 712 is a relatively simplified example used to illustrate patient specific packaging data, where the patient specific packaging data may comprise a variety of data structures and formats readable by controllers of the drug packaging system 10.

Chart 712 illustrates patient specific packaging data for seven days of a patient specific pharmacy order, where a blister pack 90 corresponds to a specific date and time of the day (morning, lunchtime, evening, bedtime). In this exemplary embodiment, each blister pack 90 includes eight blister compartments 94. The patient specific packaging data indicates the appropriate compartment 94 of a blister pack 90 into which each unit dose 422 of a prescription should be placed. As such, chart 712 illustrates exemplary drug packaging data that may be generated from the four exemplary prescriptions of FIG. 21B.

FIG. 21D provides exemplary chart 714 which illustrates patient specific packaging data corresponding to the exemplary prescriptions of FIG. 21B. As such, chart 714 of FIG. 21D is an alternative exemplary embodiment of patient specific packaging data as compared to chart 712 of FIG. 21C. Moreover, the patient specific packaging data illustrated in chart 714 illustrates an example where the patient specific packaging data is generated based at least in part on prescription data associated with the loaded prescriptions, patient preference data received from an external resource, and/or drug contra-indication data received from an external resource. In this example, patient preference data indicates that the patient does not awaken each day in the morning time period and that the drugs of prescriptions 710c and 710d (e.g., Drug C and Drug D) of FIG. 21B may interact, and should not be taken at the same dosing time.

Based at least in part on the prescription data, the patient preference data, and the drug contra-indication data, the patient specific drug packaging data is generated. As opposed to chart 712, chart 714 includes blister packs 90 corresponding to only three times of day (lunchtime, evening, bedtime) because the patient preference data indicated that the patient does not awaken in time to take medication at the morning time slot. As such, blister packs 90 associated with the morning medication pass are not filled, and hence, patient specific packaging data is not generated for morning pass blister packs 90. Moreover, as shown in chart 714, the patient specific packaging data indicates that the drugs of prescriptions 710c and 710d (e.g., Drug C and Drug D) of FIG. 21B are not packaged to be taken by the patient at the same dosing time, because the drug contra-indication data indicated that the drugs may interact. Thus, the chart 714 of filling instructions in this alternative embodiment takes into consideration patient preferences and drug contra-indications, as well as other factors.

As such, in some embodiments, the drug packaging system 10 may load a plurality of prescriptions corresponding to a plurality of patients. In these embodiments, the drug packaging system 10 may be configured to sort the prescriptions into patient prescription groups based on the patient identified in the prescription data of each loaded prescription, such that the drug packaging system 10 may process and fill patient specific pharmacy orders for each unique patient of the plurality of patients.

Those skilled in the art will recognize that the exemplary environment illustrated in FIG. 1 is not intended to limit the invention. Indeed, those skilled in the art will recognize that other alternative hardware and/or software environments may be used without departing from the scope of the embodiments of the invention. For example, controllers 12, 18, 42 may be embodied in one or more computers configured to perform the functions described above with regard to controllers 12, 18, 42. Those skilled in the art will also recognize that the invention contemplates all types of controllers including computing systems and other programmable electronic devices configured with processors, memory and/or storage devices, including, for example, client computers, server computers, portable computers, handheld computers, embedded controllers, general purpose controllers, special purpose controllers, etc.

Once the packaging or filling instructions are generated based on the various prescription data and patient preferences as described in FIGS. 17 through 21D, the instructions are ready for delivery to the manual packaging station 14 or to the automated packaging station 16. In the example of the automated packaging station 16, the machine controller 42 and the first and second robots 44, 46 may then follow the prompts created by the automated packaging station 16 as described below to fully package the order for a patient.

With reference to the flowcharts shown in FIGS. 22 through 36, an exemplary filling process for the blister packs 90 is shown and described in detail below. In the exemplary embodiment, each order for a particular month and a particular patient will have been broken into filling instructions for 120 individual blister packs 90 (i.e., thirty days times four medication passes per day), and each order will be filled completely before moving to the next order. Thus, 120 individual blister packs 90 will be separated into eight trays 186 of fifteen each after filling. Once each of the blister packs 90 for the month has been filled with the appropriate oral medications and has been loaded into the eight trays 186 for that month, the trays 186 are delivered to post-filling packaging. This post-filling packaging may include additional loading of non-cassette dispensable medication products, additional verification by a pharmacist or certified pharmacy technician when appropriate per federal and state laws, and reprinting and application of new covers 96 to the blister packs 90 where needed. The post-filling packaging may also include collation and consolidation of the order into cartons 120a, 120b, 120c, 120d and other packaging, such as when the order includes non-blister pack medications or PRN blister packs 90, and shipping to the patient. As outlined above, it will be appreciated that more or fewer blister packs 90 and trays 186 may be used for a given "month" and the example above is shown for illustrative purposes only.

An example of a particular order may be as follows: a patient is instructed to take in the morning two pills of drug A every day; one pill of drug B on Mondays, Wednesdays, and Fridays; and one-half pill of drug C every three days. Assuming the first day of the month is a Monday, the first blister pack 90 (for Monday) should have a pill of drug A in compartment 1, a pill of drug A in compartment 2, a pill of drug B in compartment 3, and a half-pill of drug C in compartment 4. The second blister pack 90 (for Tuesday) should have a pill of drug A in compartment 1, a pill of drug A in compartment 2, and nothing in cavities 3 and 4. The third blister pack 90 (for Wednesday) should have a pill of drug A in compartment 1, a pill of drug A in compartment 2, a pill of drug B in compartment 3, and nothing in compartment 4. The fourth blister pack 90 (for Thursday) should have a pill of drug A in compartment 1, a pill of drug A in compartment 2, nothing in compartment 3, and a half-pill of drug C in compartment 4. When using the automated packaging station 16, each of these four drugs may be dispensed simultaneously as described above (e.g., in any combination of drugs necessary) into the four blister packs 90 in a matter of seconds using the feeder base 170 and the rotary dial 164.

Figure 22:
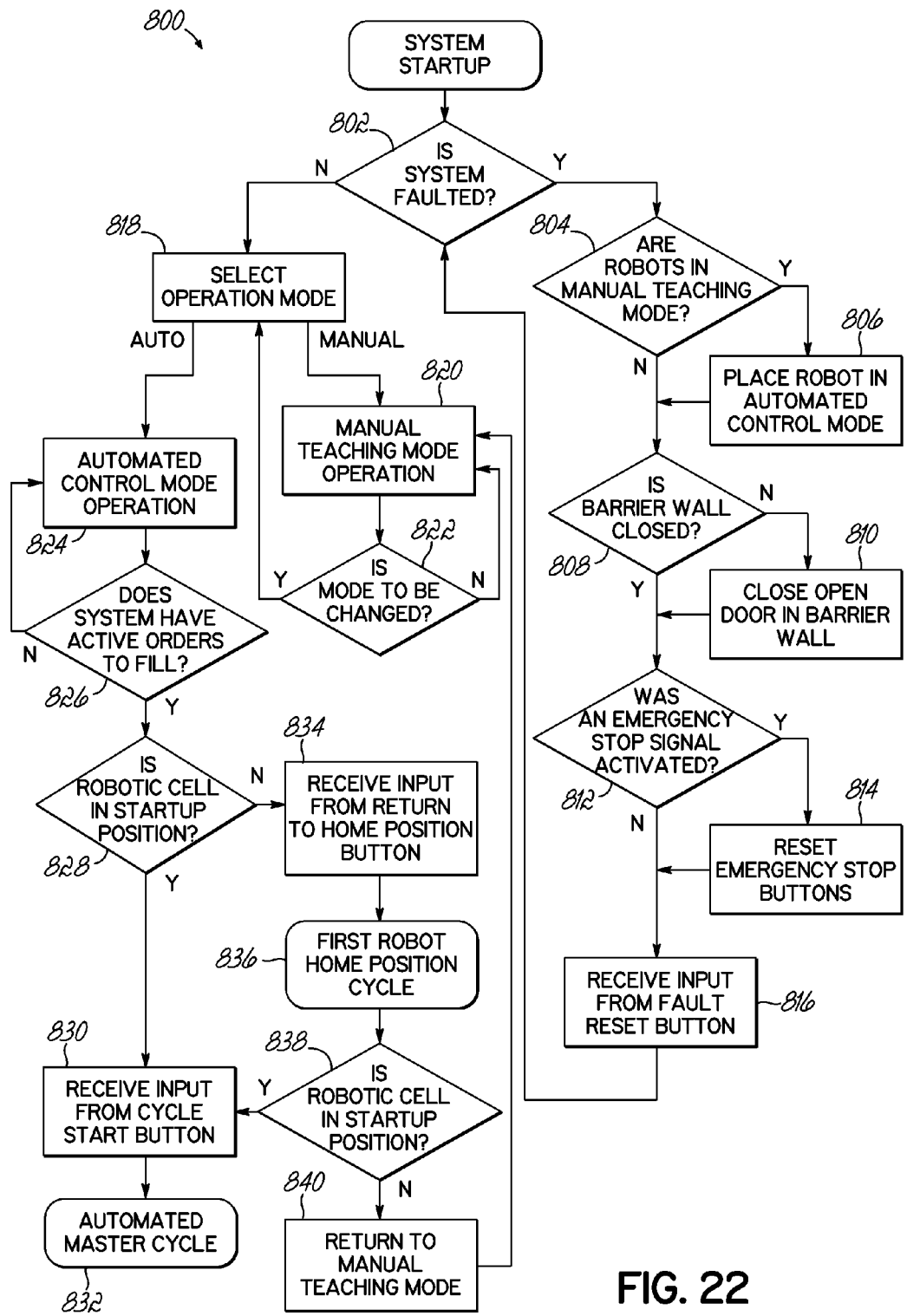
FIG. 22 is a flowchart of sequences of operations that may be performed during system startup of the automated packaging station of FIG. 4.

With reference to FIG. 22, flowchart 800 illustrates a sequence of operations that may be performed by the automated packaging station 16 during a system startup. To this end, the machine controller 42 begins by inquiring whether the system is faulted for any reason (block 802). If so, the controller 42 checks to determine if the first or second robots 44, 46 are in a manual teaching mode used for training the robots 44, 46 (block 804). If the controller 42 determines that one or both of the robots 44, 46 is in the manual teaching mode, then the controller 42 places the robot(s) 44, 46 into an automated control mode that is configured to be the normal operating mode for the robots 44, 46 (block 806). The controller 42 then checks to see if the barrier wall 150 is closed about the periphery it defines (block 808). If the barrier wall 150 is open, then the controller 42 will prompt the operators 156 to close the open doors in the barrier wall 150 (block 810). The controller 42 will then determine if an emergency stop signal was activated upon the last operation termination of the system (block 812). If an emergency stop signal was activated, then the emergency stop buttons such as those on the workstation 190 are reset (block 814). Once each of these potential faults and possibly others have been checked, the controller 42 receives input from an operator 156 at a fault reset button that operates to reset the faulted status of the system (block 816). The controller 42 then returns to checking if the system is faulted at block 802 again. In the foregoing and following description, it will be understood that the operations described may be reconfigured to be performed in any alternative order in other embodiments of the invention, and the methods of the invention are not limited by the exemplary embodiment of the order described herein.

With continued reference to FIG. 22, if the machine controller 42 determines that the system is not faulted, an operation mode is selected from the choices of automated and manual (block 818). If the manual mode is selected, the system begins operation in the previously described manual teaching mode (block 820). The controller 42 then periodically checks to see if the operational mode is to be changed (block 822). If the mode is to be changed, then the controller 42 returns to the selection step at block 818.

If, instead, the automated mode is selected, then the system begins operation in the previously described automated control mode (block 824). The controller 42 then checks if the automated packaging station 16 has any active orders to fill (block 826). If not, the controller 42 waits for such an order to come in. If an active order is ready to fill, then the controller 42 determines if the robotic cell (e.g., shorthand notation for the automated packaging station 16) is in the startup position (block 828). If the robotic cell is in the startup position, the controller 42 waits to receive input from a cycle start button actuated by the operators 156 (block 830). Once the cycle start button has been actuated, the controller 42 continues to an automated master cycle 832 series of operations described in detail with reference to FIG. 23 below. If the robotic cell is not in the startup position as block 828, the controller 42 waits to receive input from a "Return to Home Position" button that may be actuated by the operators 156 (block 834). Once this input is received, the controller 42 operates a first robot home position cycle series of operations described in detail with reference to FIG. 26 below (block 836). After this series of operations, the controller 42 detects if the robotic cell is in the startup position (block 838). If so, the controller 42 continues to block 830 as previously described. If the robotic cell is still not in the startup position, the controller 42 returns to the manual teaching mode to correct the problems preventing the robotic cell from going to the startup position (block 840).

Figure 23:
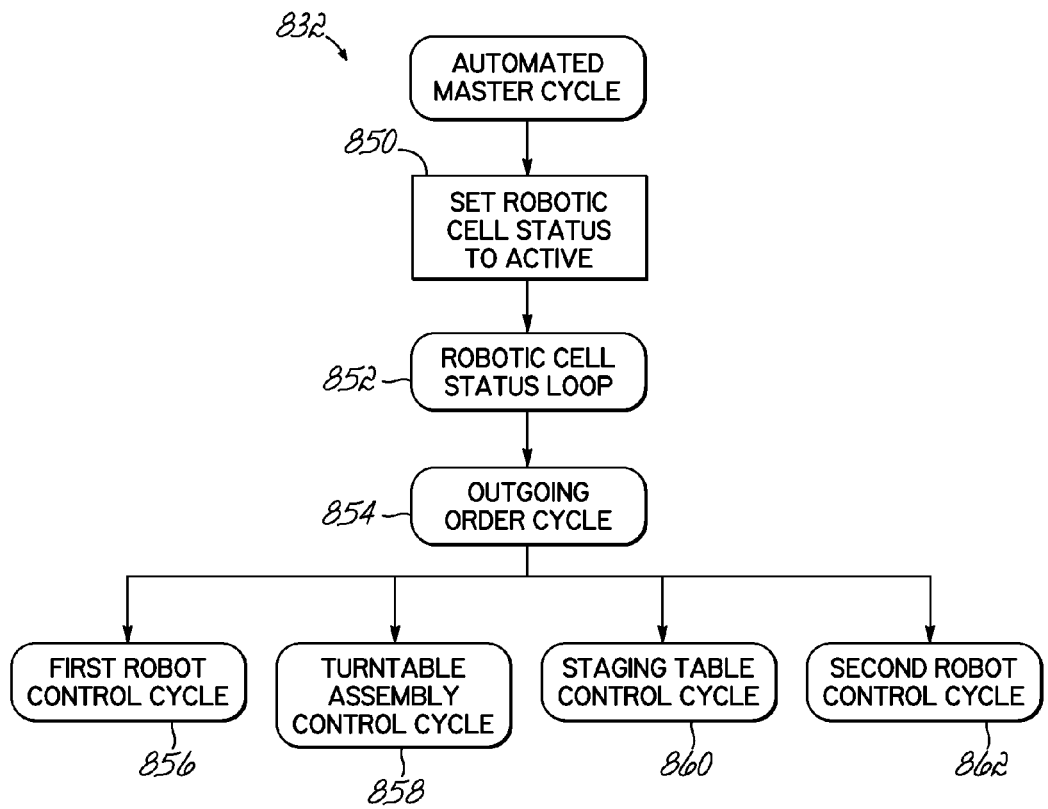
FIG. 23 is a flowchart of sequences of operations that may be performed during an automated master cycle included in the system startup flowchart of FIG. 22.

FIG. 23 illustrates a flowchart 832 including a series of operations performed during the automated master cycle of the robotic cell. In this regard, the automated master cycle 832 begins with the controller 42 setting the robotic cell status to active (block 850). The controller 42 then performs a robotic cell status loop described in further detail below with reference to FIG. 24 (block 852). The controller 42 then communicates with the offsite or central controller 12 as it performs a series of operations in an outgoing order cycle described in further detail below with reference to FIG. 25 (block 854). The outgoing order cycle selects an active order for the robotic cell to fill. Once this order has been determined, the machine control 42 operates a plurality of control cycles in parallel. These control cycles include a first robot control cycle (block 856), which is described in FIG. 27 below and is used to control operations and movements of the first robot 44; a turntable assembly control cycle (block 858), which is described in FIG. 32 below and is used to control operations of the turntable assembly 48 and associated components; a staging table control cycle (block 860), which is described in FIG. 33 below and is used to control operations of the loading and unloading staging tables 172, 174; and a second robot control cycle (block 862), which is described in FIG. 34 below and is used to control movements and operations of the second robot 46 and of the blister unloading station 182. Consequently, the automated master cycle 832 describes the primary functionality of the robotic cell during operation of the drug packaging system 10.

Figure 24:
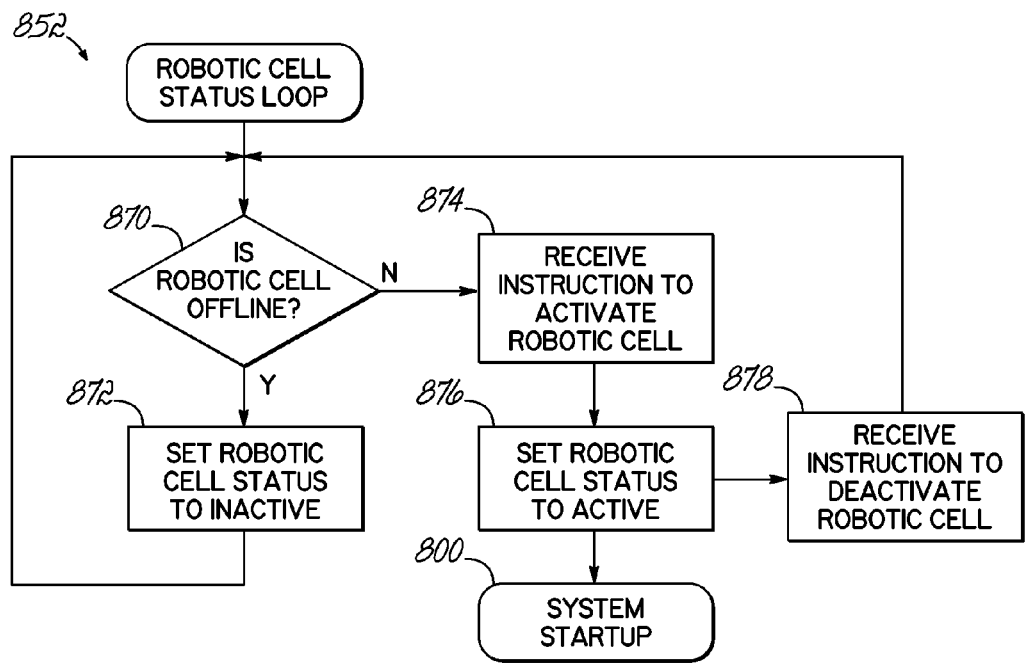
FIG. 24 is a flowchart of sequences of operations that may be performed during a robotic cell status loop included in the automated master cycle flowchart of FIG. 23.

With reference now to FIG. 24, flowchart 852 illustrates a series of operations performed during a robotic cell status loop as previously described briefly. The controller 42 determines if the robotic cell is offline (block 870). If so, the robotic cell status is set to inactive by the controller 42 (block 872). The controller 42 then periodically checks at block 870 to see if this status has changed, e.g., if the robotic cell is no longer offline. In such circumstances, the controller 42 receives an instruction from other controllers or the operators 156 to activate the robotic cell (block 874). When this instruction is received, the controller 42 sets the robotic cell status to active (block 876). The system then starts with the system startup flowchart 800 previously described to start the robotic cell. In addition, the controller 42 also waits to receive an instruction to deactivate the robotic cell (block 878). When that occurs, the controller 42 goes back to block 870 to determine if the robotic cell is offline. This cycle repeats continually during operation of the robotic cell to always communicate accurately the current status of the robotic cell, whether active or inactive.

Figure 25:
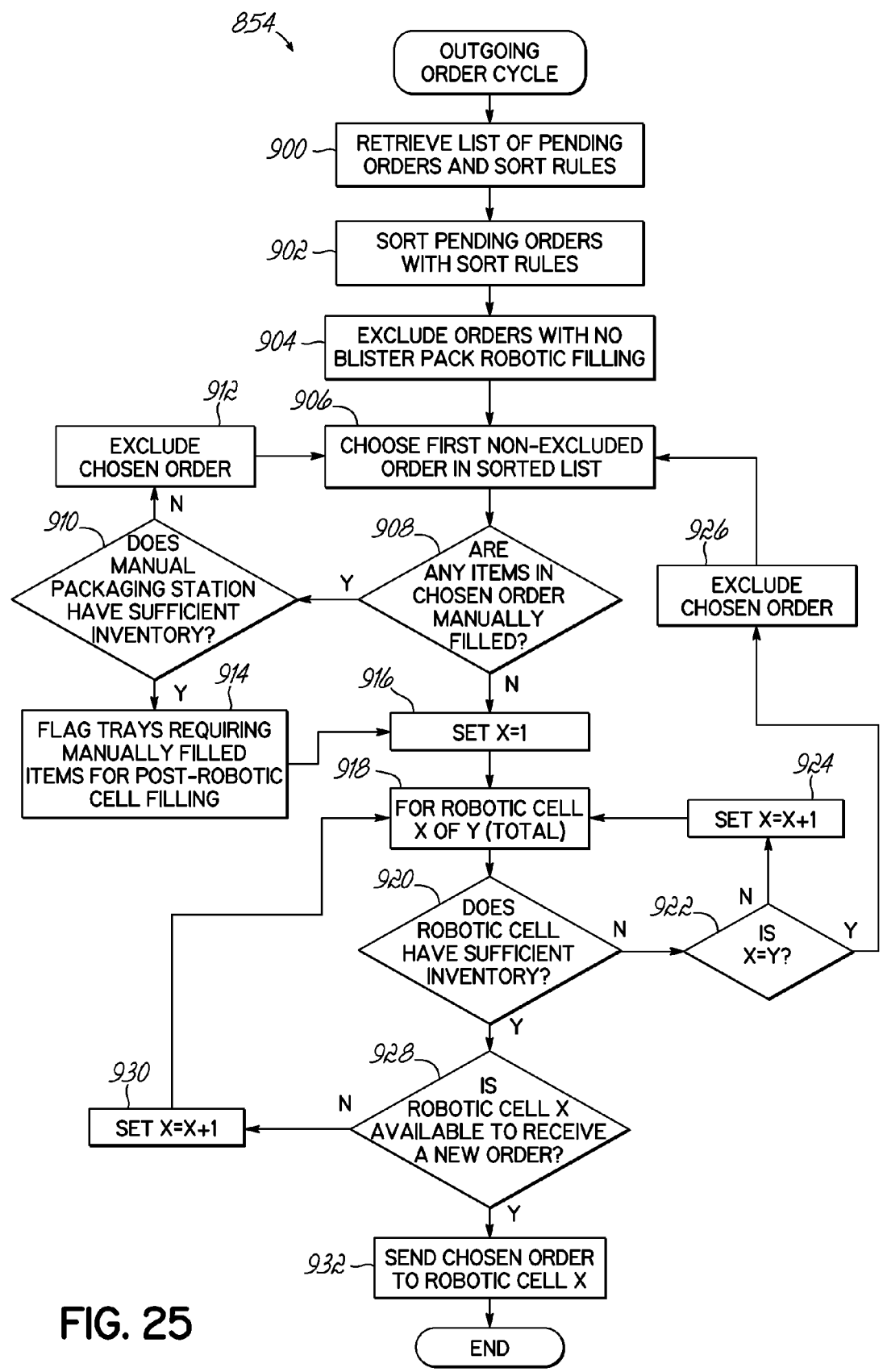
FIG. 25 is a flowchart of sequences of operations that may be performed during an outgoing order cycle included in the automated master cycle flowchart of FIG. 23.

FIG. 25 illustrates flowchart 854, which corresponds to the outgoing order cycle performed by the drug packaging system 10 and more specifically by the central controller 12 in combination with the machine controller 42. The central controller 12 retrieves a list of pending orders and sort rules (block 900). The pending orders are then sorted using these sort rules (block 902). For example, a sort rule might be defined with group by fields of: DATE_TO_SHIP, CYCLE_START_DATE, PACKAGE_TYPE, ORDER_NUMBER, and PASS_TIME. The rule might be further defined with sort by fields of: DATE_TO_SHIP (ascending), CYCLE_START_DATE (ascending), and PASS_TIME (ascending). In this case, when an order is requested, the Host Interface would take all the picks that it has received and group them so that all the picks with the same DATE_TO_SHIP, CYCLE_START_DATE, PACKAGE_TYPE, ORDER_NUMBER, and PASS_TIME are in the same group. This essentially generates a list of groups. Those groups would then be sorted by DATE_TO_SHIP, then by CYCLE_START_DATE, and then by PASS_TIME. The system will take the top group in the list, and build a list of all pick records that match the "sort by" fields of that record. In this example, it would now have a list of picks that all have the earliest DATE_TO_SHIP, then CYCLE_START_DATE, then PASS_TIME, but would be for any number of orders. It will be understood that the particular parameters and the hierarchy of parameters used to generate the sort rules may be modified in other embodiments consistent with the scope of the current invention.

Returning to FIG. 25, the central controller 12 then excludes orders with no blister pack automated filling required (block 904). The first non-excluded order in the sorted list is then chosen (block 906). The controller 12 determines if any items in the chosen order are manually filled (block 908). If so, the controller 12 checks to see if the manual packaging station 14 (or one of the available stations 14, if multiples are available) includes sufficient inventory to fill those items (block 910). If the inventory on hand is not sufficient, then the order is excluded (block 912) and the controller 12 returns to block 906 to choose the next non-excluded order. If sufficient inventory is on hand, then the trays 186 used with the manually filled items are flagged for post robotic cell filling (block 914). To this end, the controller 12 continues with the assignment process and the flagged trays 186 will be prompted for forwarding to the manual packaging station 14 following filling of the other necessary medications at the automated packaging station 16.

The controller 12 continues to block 916, which is also where the controller 12 continues to if there are no items in the chosen order that must be manually filled at block 908. At block 916, a variable X is set to be equal to 1. The controller 12 then determines for robotic cell X out of Y total robotic cells available (block 918), whether that robotic cell X has sufficient inventory to fill the necessary blister packs 90 in the chosen order (block 920). If not enough inventory is on hand at that robotic cell, the controller checks if the variable X is equal to the total number of robotic cells Y (block 922) and increments X by adding one to its value if X is not equal to Y (block 924). The controller 12 then repeats the process of checking if the robotic cell X has enough inventory at block 920. If, however, each of the robotic cells has been checked, and X=Y at block 922, then the chosen order is excluded (block 926) and the controller 12 returns to block 906 to choose the next non-excluded order. Once a robotic cell X has been determined to have sufficient inventory to fill the chosen order, the controller 12 inquires as to whether the robotic cell X is available to receive a new order (block 928). If no new orders can be received by robotic cell X, then X is incremented by one (block 930) and the controller 12 returns to block 918 to check the next robotic cell. On the contrary, if the robotic cell X can receive a new order, then the chosen order is sent to robotic cell X for filling (block 932) and the process ends or starts over. Consequently, the controller 12 operates to efficiently order and supply packaging orders to the appropriate robotic cell(s).

Figure 26:
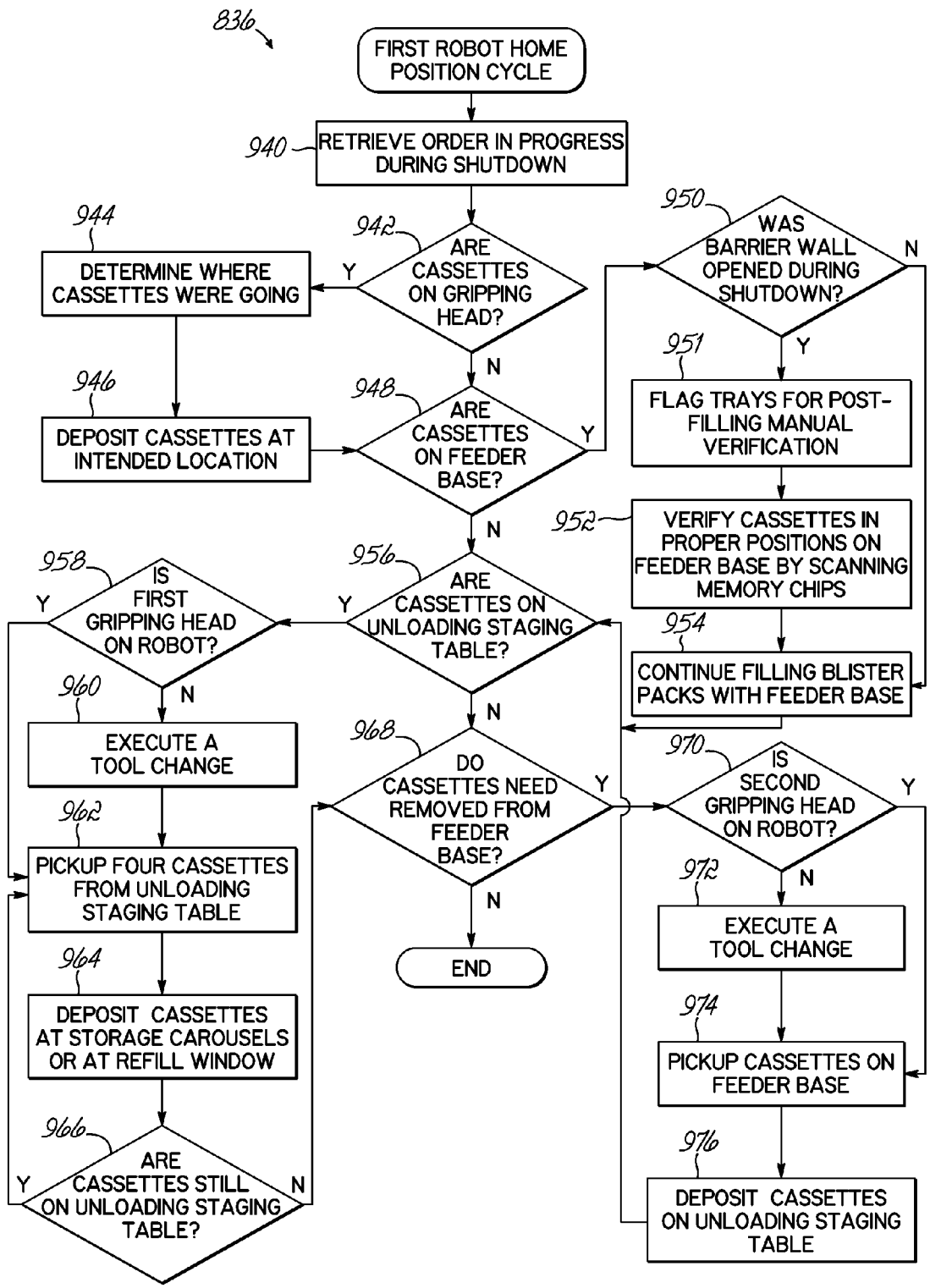
FIG. 26 is a flowchart of sequences of operations that may be performed during a first robot home position cycle included in the system startup flowchart of FIG. 22.

Now with reference to FIG. 26, flowchart 836 illustrates the first robot home position cycle, which is a series of operations designed to place the first robot 44 and associated equipment on the turntable assembly 48 in a home position. In this regard, the machine controller 42 operates to retrieve an order that was in progress during the last system shutdown, if any (block 940). The controller 42 checks to see if any cassettes 162 are located on the gripping head 470, 472 of the robot 44 (block 942). If there are cassettes 162 at that location, then the controller 42 determines where those cassettes 162 were to be deposited (block 944), and then causes the cassettes 162 to be deposited at the intended location (block 946). After this step, or in the event that there were no cassettes 162 on the gripping head 470, 472, the controller 42 determines if cassettes 162 are located on the feeder base 170 (block 948). If cassettes 162 are located on the feeder base 170, then the controller 42 checks if the barrier wall 150 was opened during the shutdown period (block 950). If the barrier wall 150 was opened, then the trays 186 are flagged for manual post-filling verification (block 951). After flagging the trays 186, the machine controller 42 verifies that the cassettes 162 are in the expected positions on the feeder base 170 (e.g., the cassettes 162 have not been reordered by an operator during shutdown) by scanning the memory chip 435 on the cassettes 162 (block 952). Following this verification, or if the barrier wall 150 was not opened during shutdown at step 950, any remaining blister packs 90 to be filled with the medications in those cassettes 162 continue to be filled at the feeder base 170 (block 954).

The controller 42 then determines if cassettes 162 are located on the unloading staging table 174 (block 956). If cassettes are located on the unloading staging table 174, the controller 42 checks whether the first gripping head 470 is on the first robot 44 (block 958). If the first gripping head 470 is not on the robot, then the controller 42 causes the first robot 44 to execute a tool change (block 960). Once the first gripping head 470 is on the first robot 44, the robot 44 picks up four cassettes 162 from the unloading staging table 174 (block 962). The first robot 44 then deposits the cassettes 162 on the storage carousels 160 or at the refill window 176 (block 964). The controller 42 then detects whether any cassettes 162 are still located on the unloading staging table 174 (block 966). If cassettes 162 are still located there, the controller 42 returns to block 962 for picking up the cassettes 162 from the unloading staging table 174. If all of the cassettes 162 have been removed, then the controller 42 determines whether any cassettes 162 need to be removed from the feeder base 170 (block 968). This determination is also made immediately after block 956 if it is detected that no cassettes 162 are on the unloading staging table 174. If no cassettes 162 need to be removed from the feeder base 170, then the first robot home position cycle ends.

However, if cassettes 162 do need to be removed from the feeder base 170, then the controller 42 checks to see if the second gripping head 472 is on the first robot 44 (block 970). If the second gripping head 472 is not on the first robot 44, then the first robot 44 executes a tool change (block 972). Once the first robot 44 has the second gripping head 472, the second gripping head 472 is used to pick up cassettes 162 from the feeder base 170 (block 974). The first robot 44 then deposits the cassettes 162 onto the unloading staging table 174 (block 976). The controller 42 then returns to block 956, where it is determined that the cassettes 162 have been placed on the unloading staging table 174 for removal.

Figure 27:
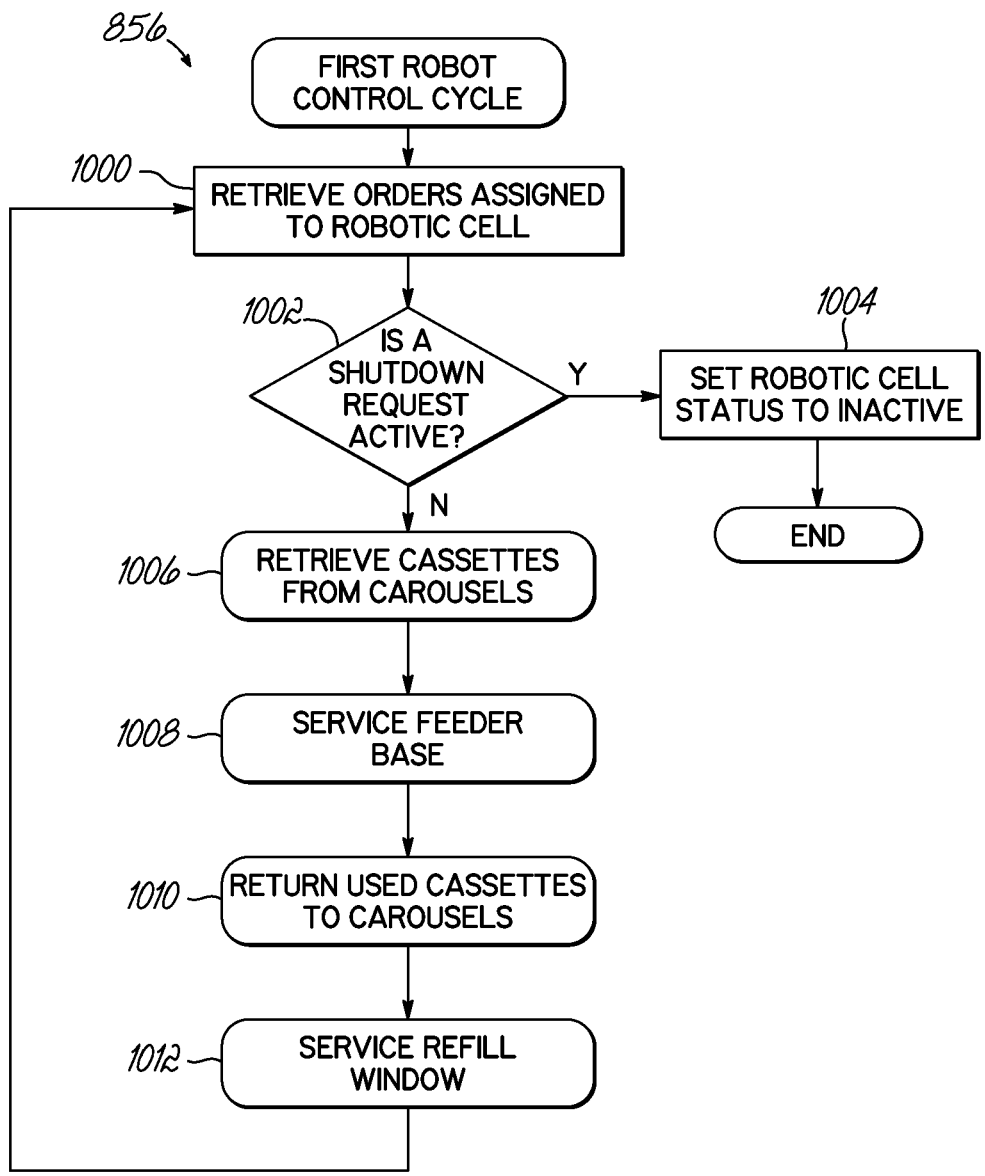
FIG. 27 is a flowchart of sequences of operations that may be performed during a first robot control cycle included in the automated master cycle of FIG. 23.

FIG. 27 illustrates flowchart 856, which shows a series of operations making up the first robot control cycle. This control cycle begins with the controller 42 retrieving orders assigned to the robotic cell (block 1000). The controller 42 determines if a shutdown request is active (block 1002). If such a shutdown request is active, then the controller 42 sets the robotic cell status to inactive (block 1004) and the control cycle ends. Otherwise, the first robot 44 follows a series of operations for retrieving cassettes 162 from the carousels 160 as described below at FIG. 28 and flowchart 1006. The first robot 44 then services the feeder base 170 according to the series of operations described below at FIG. 29 and flowchart 1008. The first robot 44 then returns used cassettes 162 to the carousels 160 according to the series of operations described below at FIG. 30 and flowchart 1010. Finally, the first robot 44 services the refill window 176 according to the series of operations described below at FIG. 31 and flowchart 1012. The controller 42 then returns to block 1000 to retrieve any more orders assigned to the robotic cell and then continue the control cycle. It will be understood that the machine controller 42 prioritizes actions so that return of refilled or repaired cassettes 162 on the refill window 176 into the robotic work zone 152 occurs as soon as possible, to avoid that action holding up other filling actions for a subsequent set of blister packs 90. This process is described in detail below, especially in conjunction with flowchart 1012 at FIG. 31.

Figure 28:
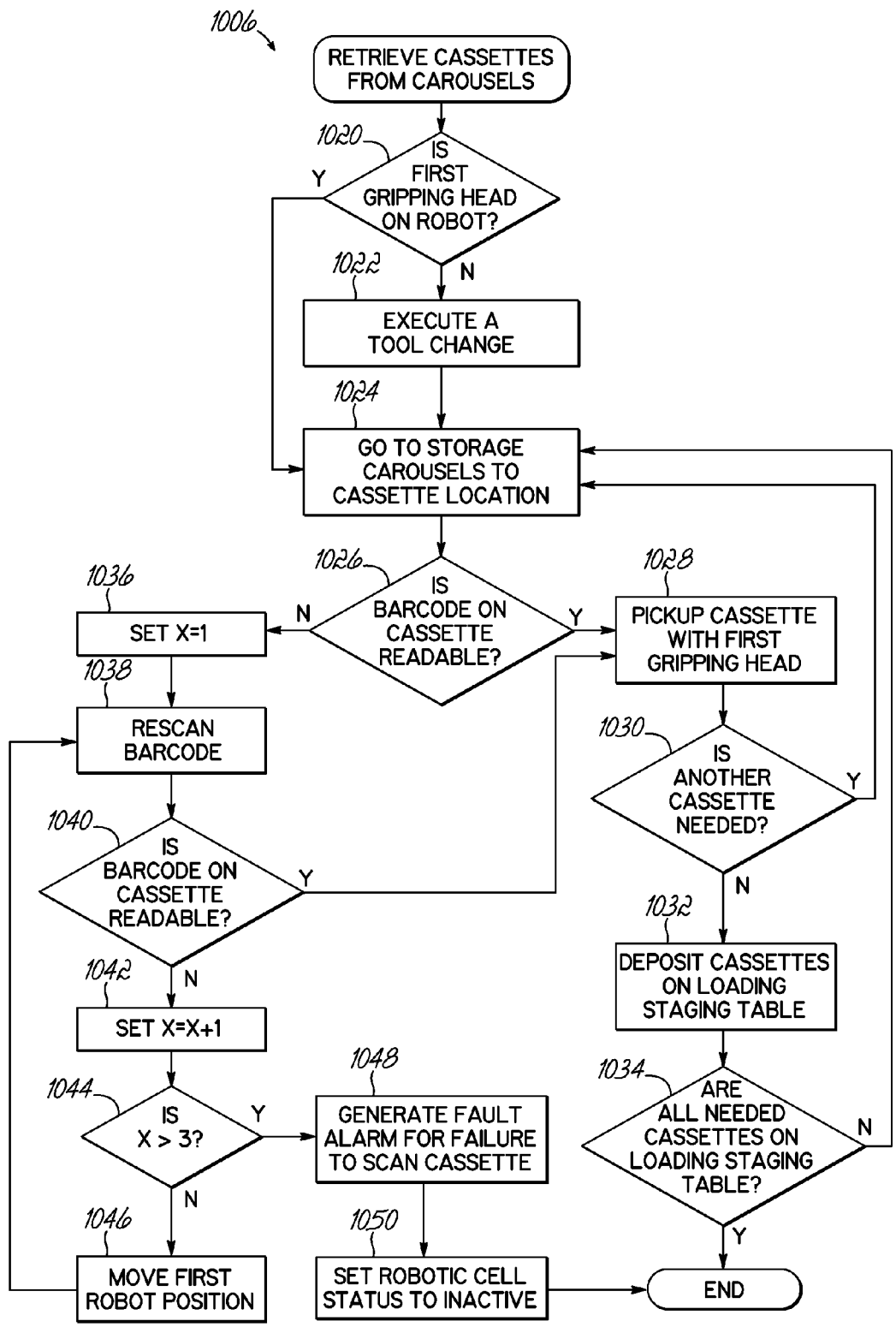
FIG. 28 is a flowchart of sequences of operations that may be performed during a retrieval of cassettes from carousels included in the first robot control cycle of FIG. 27.

With reference to FIG. 28, flowchart 1006 illustrates a series of operations performed to retrieve cassettes 162 from the storage carousels 160. The controller 42 determines if the first gripping head 470 is on the first robot 44 (block 1020). If the first gripping head 470 is not on the first robot 44, then the first robot 44 executes a tool change (block 1022). Once the first robot 44 has the first gripping head 470 equipped, the first robot 44 goes to the storage carousels 160 to the location of a cassette 162 (block 1024). The first robot 44 scans the barcode on the cassette 162 and the controller 42 determines if the barcode has been accurately read (block 1026). If the barcode is read, the first robot 44 picks up the cassette 162 with the first gripping head 470 (block 1028). The controller 42 then queries whether another cassette 162 is needed from the carousels 160 (block 1030). If another cassette 162 is necessary, the first robot 44 returns to the storage carousels 160 to the location of another cassette 162 at block 1024. If no more cassettes 162 are needed, then the first robot 44 deposits the cassettes 162 on the loading staging table 172 (block 1032). The controller 42 then determines if all needed cassettes 162 are located on the loading staging table 172 (block 1034). If more cassettes 162 are needed, the controller 42 returns to block 1024 to return the first robot 44 to the storage carousels 160 to another cassette location. If no more cassettes 162 are needed on the loading staging table 172, then the retrieval cycle ends.

Returning to the block 1026 when the barcode on the cassette 162 is scanned, the controller 42 sets a variable X equal to 1 if the barcode is not successfully read (block 1036). The first robot 44 then tries again by rescanning the barcode (block 1038). The controller 42 then determines if this rescan produced a reading of the barcode on the cassette (block 1040). If the barcode was successfully read, then the cassette 162 is picked up by the first robot 44 at block 1028 as previously described. If the barcode is still not read successfully, then X is incremented by 1 (block 1042) and the controller 42 checks to see if X is greater than 3 (block 1044). If X is not greater than 3, then the controller 42 causes the first robot 44 to shift position slightly (block 1046) and returns to block 1038 for rescanning the barcode again. If, on the other hand, X is determined to be greater than 3 at block 1044, the controller 42 generates a fault alarm for the failure to scan the cassette 162 (block 1048). The controller 42 may also check for alternative locations on the storage carousels 160 holding other cassettes 162 with the same medication at this point in some embodiments of the invention. In these circumstances, if such an alternative cassette 162 is not available, the robotic cell status is then set to inactive (block 1050) and the retrieval process ends.

Figure 29:
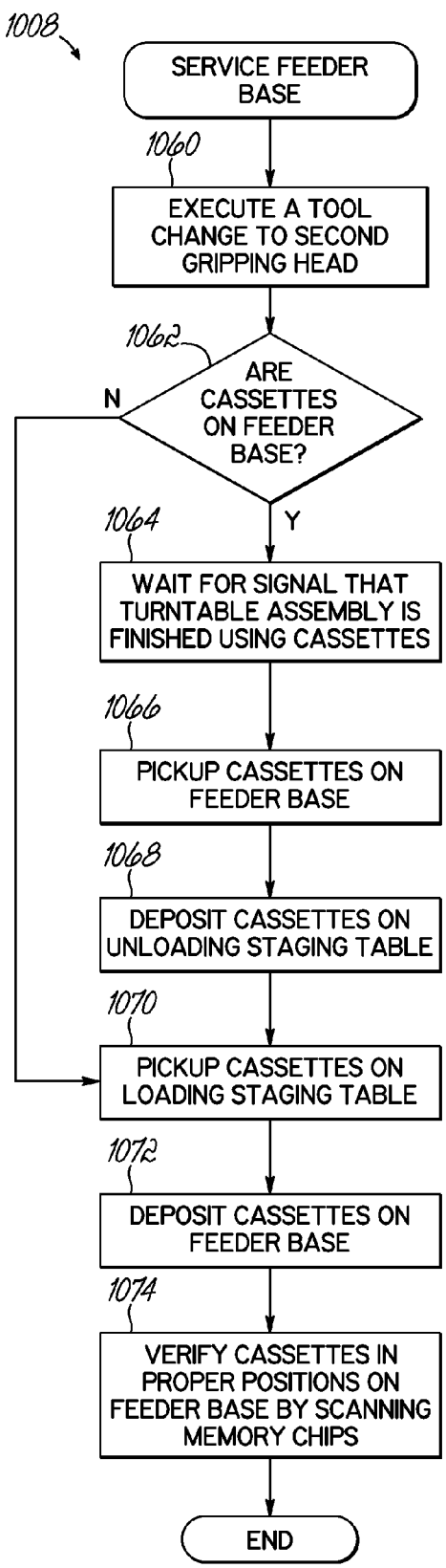
FIG. 29 is a flowchart of sequences of operations that may be performed during servicing of the feeder base included in the first robot control cycle of FIG. 27.

Turning to FIG. 29, flowchart 1008 illustrates a series of operations performed during the servicing of the feeder base 170, after the cassettes 162 have been retrieved as discussed above. This process begins by causing the first robot 44 to execute a tool change to grab the second gripping head 472 (block 1060). The controller 42 then checks if any cassettes 162 are located on the feeder base 170 already (block 1062). If cassettes 162 are located on the feeder base 170, the controller 42 waits for a signal that the turntable assembly 48 is finished using the active cassettes 162 (block 1064). Once this signal is received, the first robot 44 picks up the cassettes 162 on the feeder base (block 1066). These cassettes 162 are moved and deposited on the unloading staging table 174 (block 1068). The first robot 44 then picks up the cassettes on the loading staging table 172 (block 1070). This pick up also occurs immediately after a determination that cassettes 162 are not on the feeder base 170 at block 1062. The first robot 44 then deposits these new cassettes 162 onto the feeder base 170 (block 1072). As described in detail above, the controller 42 then actuates a polling of identification information from the memory chips 435 on the cassettes 162 at the feeder base 170 to verify accurate placement of the cassettes 162 on the appropriate actuator petals 370 (block 1074), and the servicing of the feeder base 170 ends.

Figure 30:
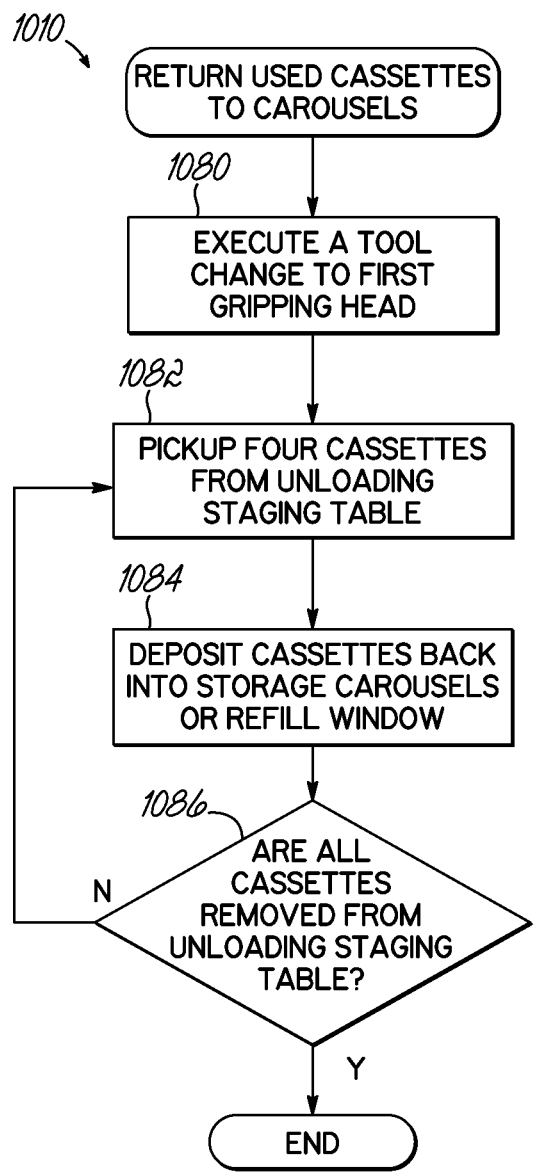
FIG. 30 is a flowchart of sequences of operations that may be performed during a return of used cassettes to carousels included in the first robot control cycle of FIG. 27.

Now with reference to FIG. 30, flowchart 1010 shows a series of operations used to return used cassettes 162 back to the storage carousels 160. The first robot 44 executes a tool change to retrieve and use the first gripping head 470 (block 1080). The first robot 44 then picks up four cassettes 162 from the unloading staging table 174 (block 1082). These cassettes 162 are deposited back into storage carousels 160 or placed at the refill window 176 if a replenishment of stock is necessary (block 1084). The controller 42 then checks to see if all of the cassettes 162 have been removed from the unloading staging table 174 (block 1086). If all of the cassettes 162 have not been removed, the first robot 44 picks up the remaining cassettes 162 from the unloading staging table 174 by returning to block 1082. Once all of the cassettes 162 have been removed, this series of operations ends.

Figure 31:
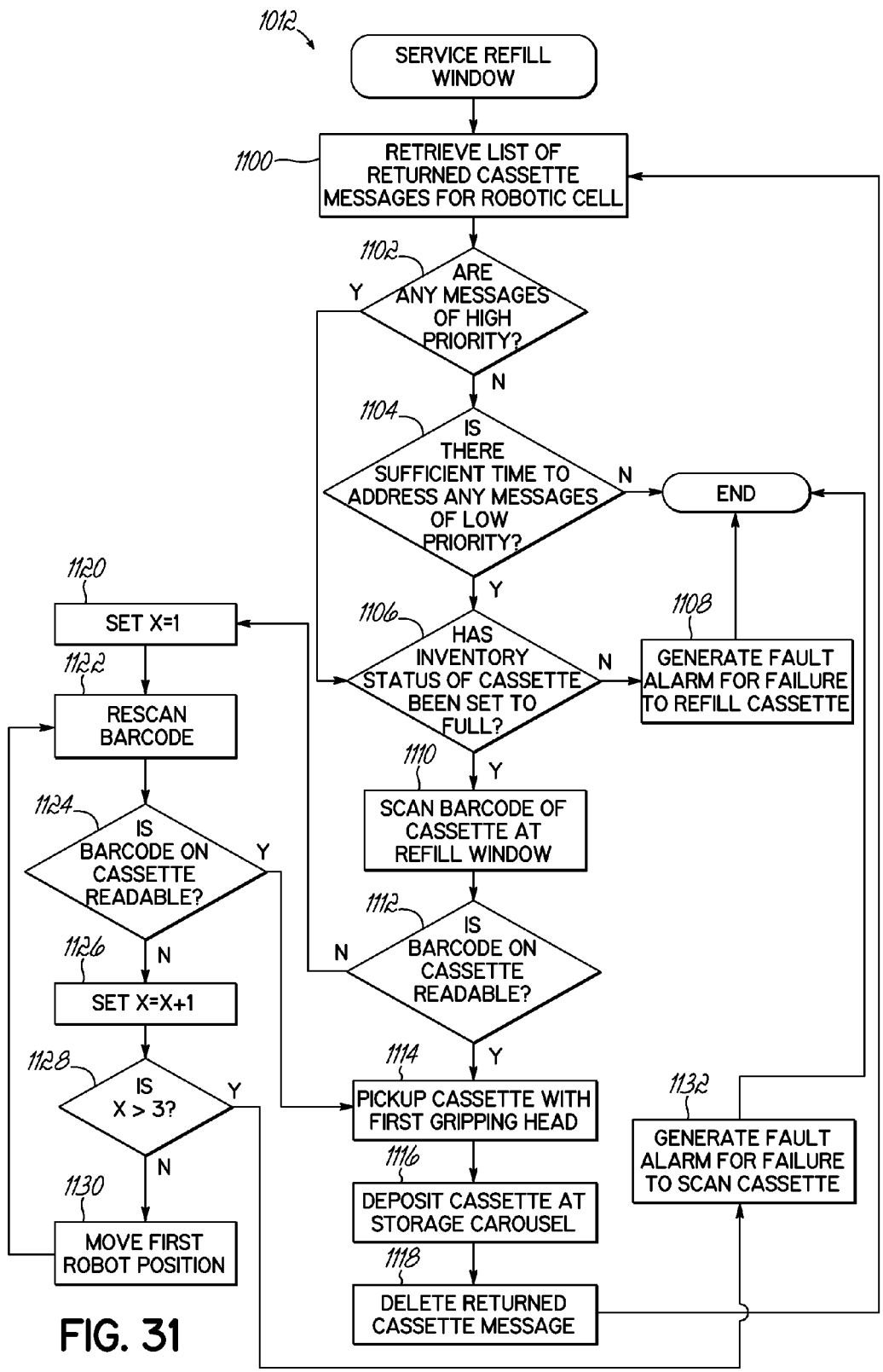
FIG. 31 is a flowchart of sequences of operations that may be performed during servicing of the refill window included in the first robot control cycle of FIG. 27.

FIG. 31 illustrates flowchart 1012, which describes a series of operations for servicing the refill window 176 with the first robot 44. To this end, the controller 42 retrieves a list of returned cassette messages for the robotic cell (block 1100). These messages indicate when a refilled cassette 162 is ready to be picked up again at the refill window 176. As noted above, the controller 42 continually prioritizes the series of actions of the first robot 44 so that picking up these cassettes 162 can be conducted as soon as possible. To this end, the controller 42 checks to see if any of the messages are deemed high priority (block 1102). If none of the messages are high priority, the controller 42 determines if there is sufficient time to address any of the messages of low priority (block 1104). If there is sufficient time or if any messages were deemed to be high priority, then the controller 42 determines if the inventory status of the cassette 162 has been set to full, which indicates the refill has been completed (block 1106). If this inventory status is not set to full, then the controller 42 generates a fault alarm for failure to refill the cassette 162 (block 1108) and the servicing ends. Likewise, if none of the messages are high priority and not enough time is present to address low priority messages, then this series of operations ends.

Assuming that the inventory status of the cassette 162 is instead determined to be full at block 1106, the first robot 44 scans the barcode of the cassette 162 at the refill window 176 (block 1110). The controller 42 determines if the barcode on the cassette 162 was readable (block 1112). If the barcode is read, then the first robot 44 picks up the cassette 162 with the first gripping head 470 (block 1114). The cassette 162 is then deposited back at the storage carousels 160 (block 1116). The returned cassette message pertaining to this refill is deleted by the controller 42 following this deposit back to the carousels 160 (block 1118), and the controller 42 returns to block 1100 to again retrieve the list of returned cassette messages for this robotic cell.

On the other hand, if the barcode is not successfully read at block 1112, the controller 42 sets a variable X equal to 1 (block 1120). The barcode is then rescanned by the first robot 44 (block 1122). The controller 42 again determines if the barcode was successfully scanned (block 1124). If the barcode is successfully read this time, then the first robot 44 picks up the cassette 162 with the first gripping head 470 as described above in block 1112. If the barcode is still not successfully read, then X is incremented by 1 (block 1126) and the controller 42 determines if X is greater than 3 (block 1128). If X is not greater than 3, then the first robot 44 moves in position slightly (block 1130) and attempts to rescan the barcode again as described in block 1122 above. If, instead, X is greater than 3 at block 1128, then the controller 42 generates a fault alarm indicating the failure to scan the cassette 162 (block 1132) and this series of operations ends.

Figure 32:
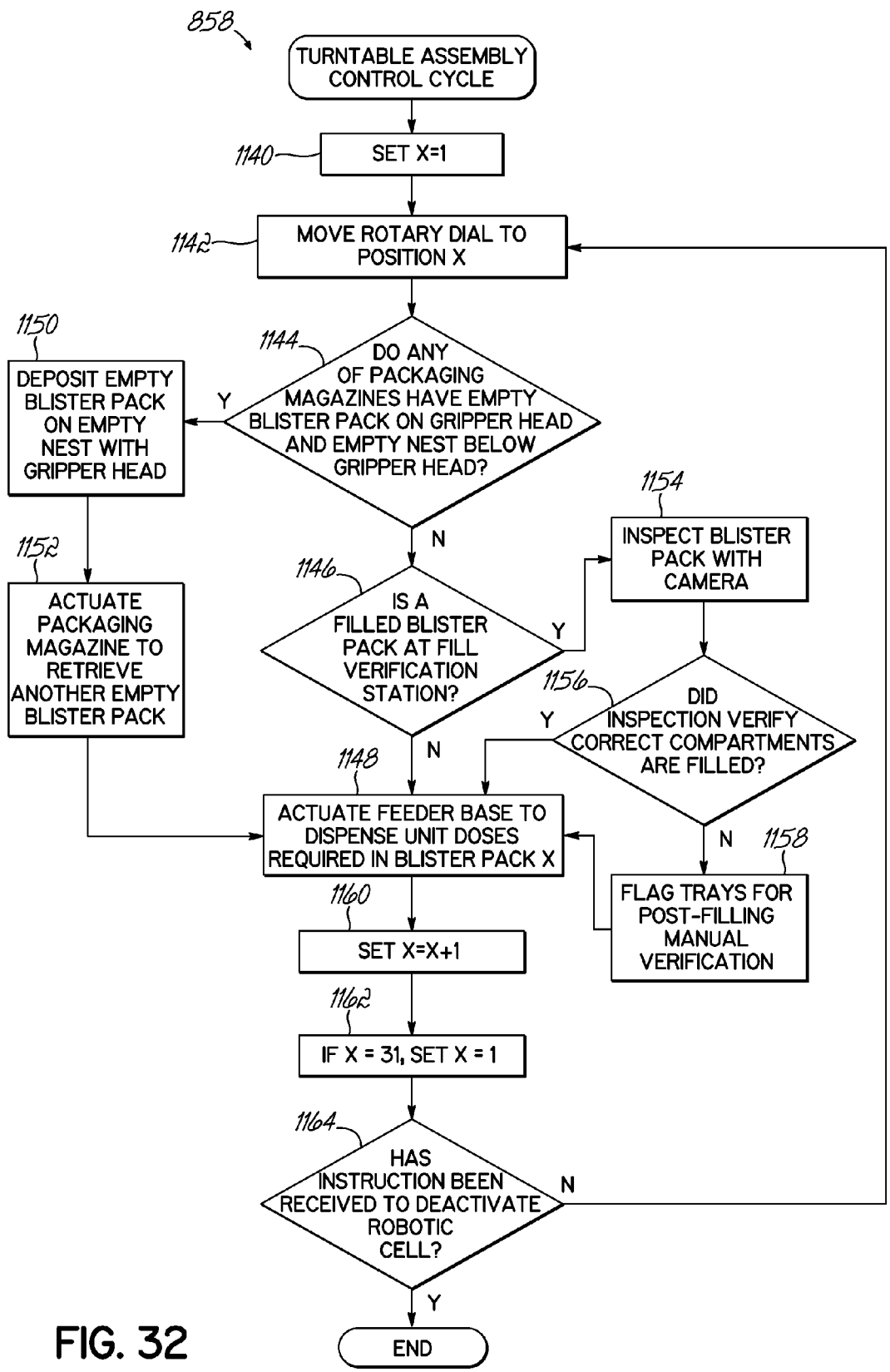
FIG. 32 is a flowchart of sequences of operations that may be performed during a turntable assembly control cycle included in the automated master cycle of FIG. 23.

FIG. 32 illustrates flowchart 858, which includes the series of operations defining the turntable assembly control cycle. The controller 42 begins this control cycle by setting variable X equal to 1 (block 1140). The rotary dial 164 is then moved to position X (block 1142). The controller 42 determines if any of the packaging magazines 168 have an empty blister pack 90 loaded on the gripping head 312 and an empty nest 166 located below the gripping head 312 (block 1144). If none of the packaging magazines 168 fit this state, then the controller 42 determines if a filled blister pack 90 is located at the fill verification station 220 (block 1146). If no filled blister pack 90 is at the fill verification station 220, then the feeder base 170 actuates to dispense unit doses required in the blister pack X (block 1148). Meanwhile, if any of the packaging magazines 168 are determined to have an empty blister pack 90 loaded and an empty nest 166 below the gripping head 312 at block 1144, the empty blister pack 90 is deposited on the empty nest 166 (block 1150). The packaging magazine 168 is then actuated to retrieve another empty blister pack 90 to prepare for the next cycle of the turntable assembly 48 (block 1152), and then the feeder base 170 is actuated at block 1148 as previously described.

If a filled blister pack 90 is detected to be at the fill verification station 220 at block 1146, then the blister pack 90 is inspected with the camera (block 1154). The controller 42 then checks if the inspection verified that the correct compartments 94 are filled (block 1156). If the inspection verifies the correct filling, then the controller 42 continues to actuate the feeder base 170 at block 1148 as previously described. If the inspection does not verify a correct fill, then the trays 186 are flagged for post-filling manual verification (block 1158). After the feeder base 170 is actuated at block 1148, the variable X is incremented by 1 (block 1160). If X is equal to 31, then X is reset to 1 to account for the complete cycle of 30 blister packs 90 being completed (block 1162). Although not described in detail in this flowchart 858, the controller 42 operates to leave one of the nests 166 empty between sets of blister packs 90 so that this empty nest 166 can be positioned underneath the feeder base 170 during replacement of cassettes 162 on the feeder base 170, as described in detail above. The controller 42 then verifies if an instruction has been received to deactivate the robotic cell (block 1164). If such an instruction has not been received, the control cycle returns to block 1142 to move the rotary dial 164 to the next position X. If the instruction to deactivate the robotic cell has been received, then the control cycle ends.

Figure 33:
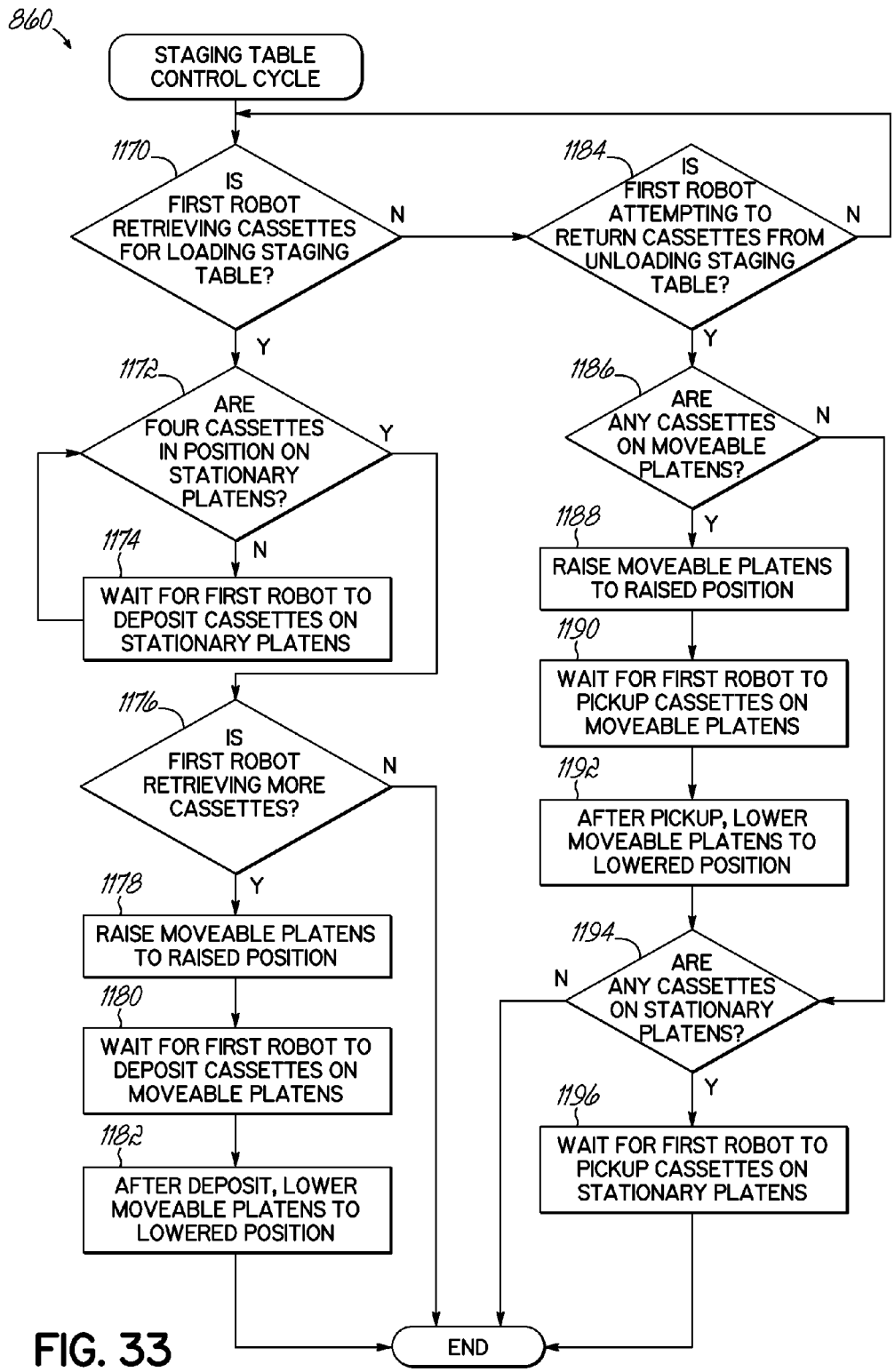
FIG. 33 is a flowchart of sequences of operations that may be performed during a staging table control cycle included in the automated master cycle of FIG. 23.

Referring to FIG. 33, flowchart 860 shows the series of operations combining to form the staging table control cycle. This control cycle includes the controller 42 determining if the first robot 44 is retrieving cassettes 162 for the loading staging table 172 (block 1170). If cassettes 162 are being retrieved for the loading staging table 172, then the controller 42 checks to see if four cassettes 162 are already in position on the stationary platens 450 (block 1172). If no cassettes 162 are in position on the stationary platens 450, then the controller 42 waits for the first robot 44 to deposit cassettes 162 onto the stationary platens 450 (block 1174). If it is determined that the stationary platens 450 have already received cassettes 162, then the controller 42 determines if the first robot 44 is retrieving more cassettes 162 for the loading staging table 172 (block 1176). If not, then this control cycle ends. If the first robot 44 is obtaining more cassettes 162, however, then the loading staging table 172 raises the moveable platens 452 to the raised position (block 1178). The controller 42 then waits for the first robot 44 to deposit cassettes 162 onto the raised, moveable platens 452 (block 1180). Once this deposit occurs, the loading staging table 172 lowers the moveable platens 452 back to the lowered position to bring all of the cassettes 162 on the loading staging table 172 back to the same height (block 1182). The control cycle then ends.

Alternatively, if the controller 42 determines at block 1170 that the first robot 44 is not retrieving cassettes 162 for the loading staging table 172, the controller 42 inquires about whether the first robot 44 is instead attempting to return cassettes 162 from the unloading staging table 174 back to the storage carousels 160 (block 1184). If not, then the controller 42 returns to block 1170 to check whether the first robot 44 is retrieving cassettes 162 for the loading staging table 172. Therefore, the controller 42 loops between these two inquiries until one of the staging tables 172, 174 is actively being worked upon. When it is determined that the first robot 44 is attempting to return cassettes 162 from the unloading staging table 174, the controller 42 first determines if any cassettes 162 are located on the moveable platens 452 (block 1186). If there are cassettes 162 on these moveable platens 452, then the unloading staging table 174 raises these moveable platens 452 to the raised position (block 1188). The controller 42 then waits for the first robot 44 to pick up the cassettes 162 from the moveable platens 452 (block 1190). Once this pick up occurs, the unloading staging table 174 lowers the moveable platens 452 back to the lowered position (block 1192). Once no cassettes 162 are located on the moveable platens 452 and the moveable platens 452 are in the lowered position, the controller moves on to determine if any cassettes 162 are on the stationary platens 450 (block 1194). If not, then the control cycle ends. If cassettes 162 are on the stationary platens 450 though, then the controller 42 waits for the first robot 44 to pick up the cassettes 162 on the stationary platens 450 before the control cycle ends (block 1196).

Figure 34:
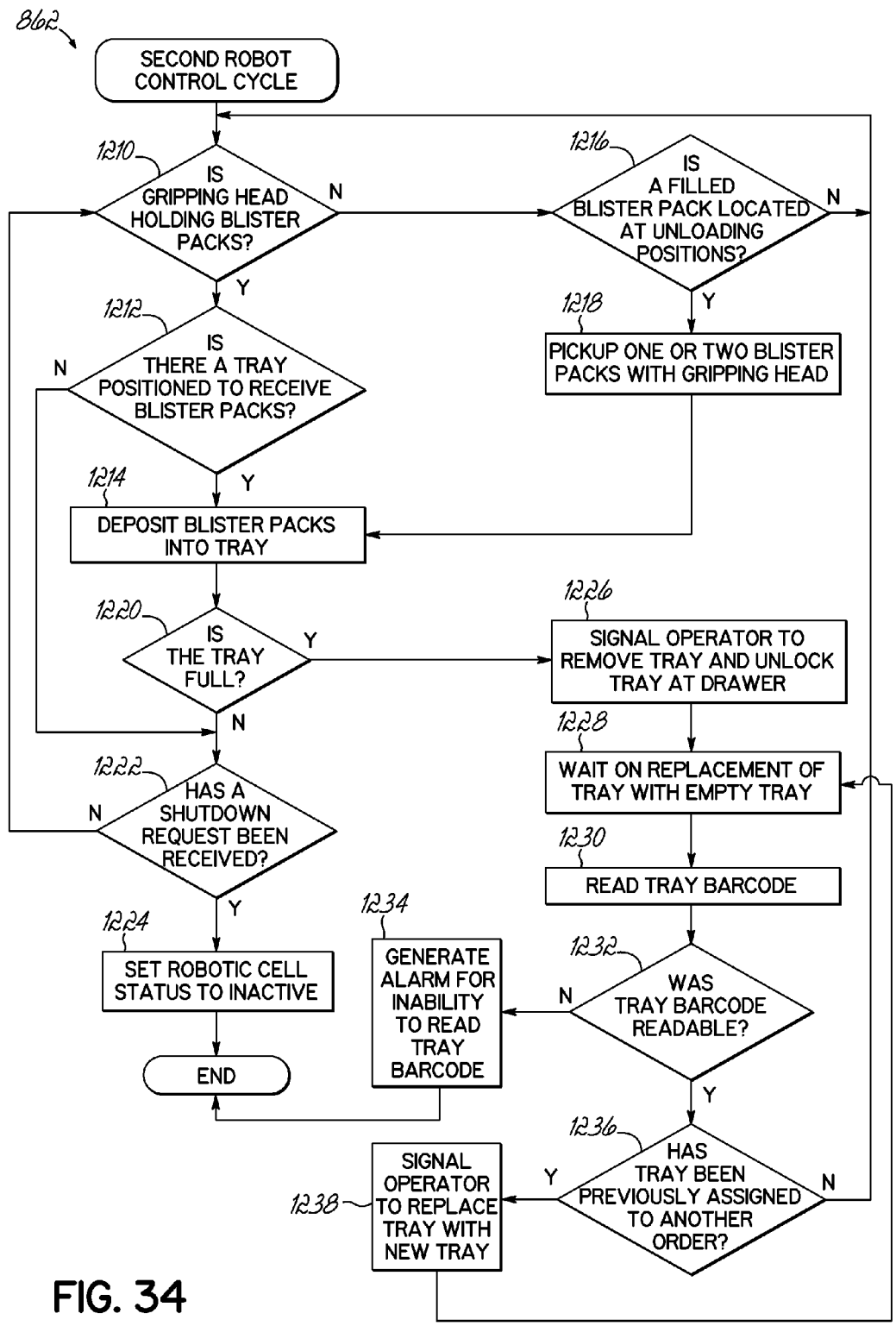
FIG. 34 is a flowchart of sequences of operations that may be performed during a second robot control cycle included in the automated master cycle of FIG. 23.

FIG. 34 shows flowchart 862, which illustrates a series of operations making up the second robot control cycle. This control cycle begins with the controller 42 determining if the gripping head 518 of the second robot 46 is holding blister packs 90 currently (block 1210). If blister packs 90 are currently being held by the gripping head 518, then the controller 42 determines if there is a tray 186 positioned to receive the blister packs 90 (block 1212). If there is a tray 186 in position, then the second robot 46 deposits the blister packs 90 into the tray 186 (block 1214). Returning to block 1210, if blister packs 90 are not being currently held by the gripping head 518, then the controller determines if a filled blister pack 90 is located at one of the blister unloading positions 228 on the rotary dial 164 (block 1216). If no blister packs 90 are awaiting pickup, then the control cycle loops back to block 1210 to check again if any blister packs 90 are on the gripping head 518. Thus, the second robot control cycle is operative to wait until something actionable is occurring with blister packs 90 at the blister unloading station 182. If there are filled blister packs 90 waiting for retrieval at the unloading positions 228 on the rotary dial 164, then the second robot 46 picks up one or two blister packs 90 from the rotary dial 164 with the gripping head 518 (block 1218) and then deposits those blister packs 90 into the tray 186 at block 1214 as previously described.

Once blister packs 90 have been deposited into the tray 186, the controller 42 checks to see if the tray 186 is full (block 1220). If the tray 186 is not full (or if there was no tray 186 as determined in block 1212), then the controller 42 checks to see if a shutdown request has been received (block 1222). If such a request has been received, then the controller 42 sets the robotic cell status to inactive (block 1224) and the control cycle ends. If no such request to shutdown has been received, then the controller 42 returns to block 1210 to monitor whether the gripping head 518 is holding blister packs 90 again.

At block 1220, if it is determined that the tray 186 is now full, the controller 42 signals the operators 156 to remove the tray 186 and unlocks any locking mechanism that would be holding the drawer 184 or tray 186 in position (block 1226). The controller 42 then waits on the replacement of the tray 186 with an empty tray 186 (block 1228). Once the tray 186 has been replaced, the tray barcode is scanned (block 1230). The controller 42 then determines if the barcode scan was successful in reading the barcode on the tray 186 (block 1232). If the scan was not successful, then the controller 42 generates an alarm for the inability to read the tray barcode (block 1234) and the control cycle ends. On the other hand, if the scan was successful, then the controller 42 determines if the tray 186 had been previously assigned to another active order (block 1236). If the tray 186 had been previously assigned to another active order, making the tray 186 unavailable for the current order, then the controller 42 signals the operators 156 to replace the tray 186 with a new tray 186 (block 1238) and then goes back to block 1228 to wait on the replacement of the tray 186 as previously described. However, if the tray 186 is determined to be free from previous assignments, then the tray 186 is accepted and the control cycle returns to block 1210 for continuing the process of unloading blister packs 90 into the tray(s) 186.

Figure 35A:
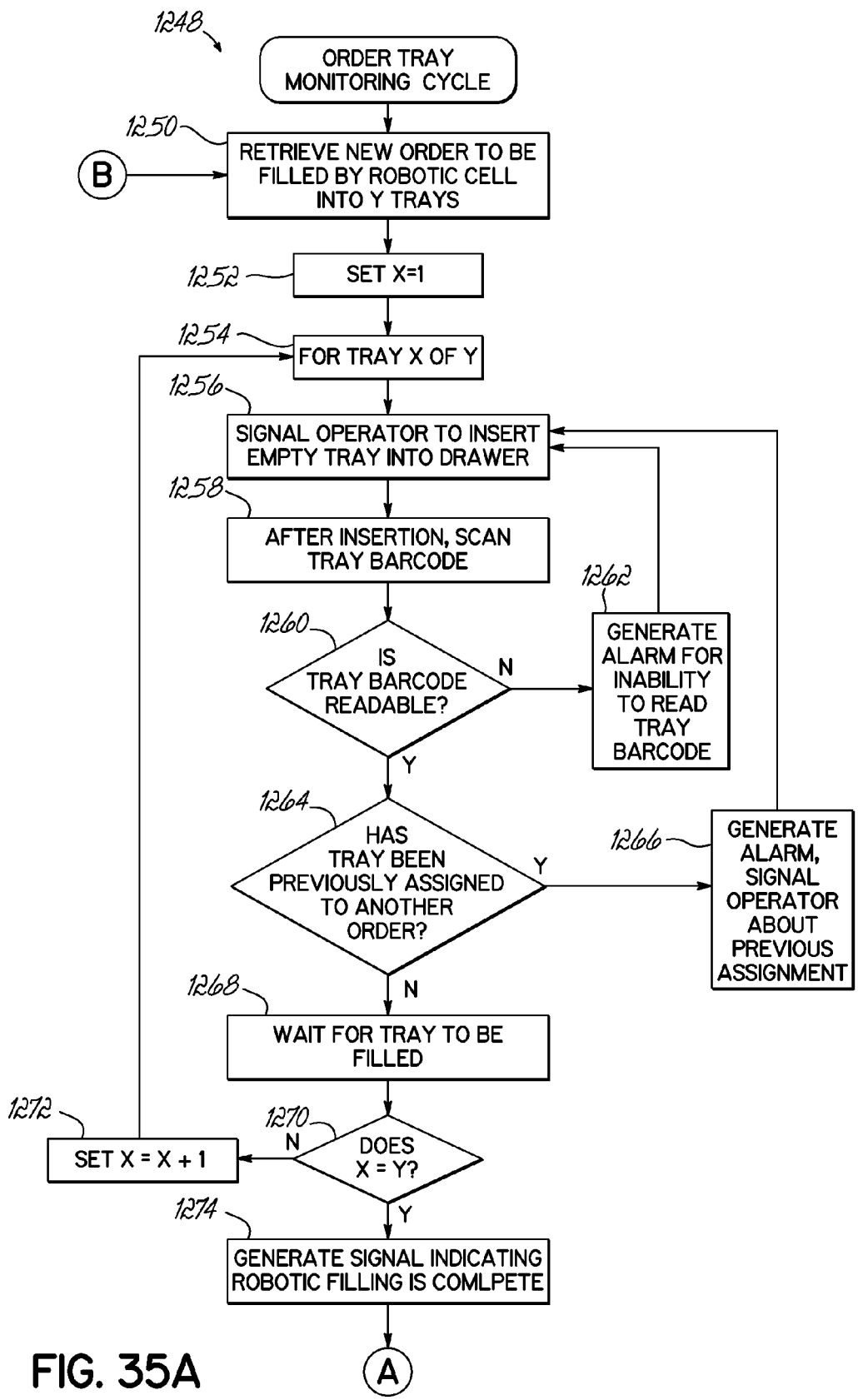
FIG. 35A is a flowchart of sequences of operations that may be performed during an order tray monitoring cycle used with the automated packaging station of FIG. 4.
Figure 35B:
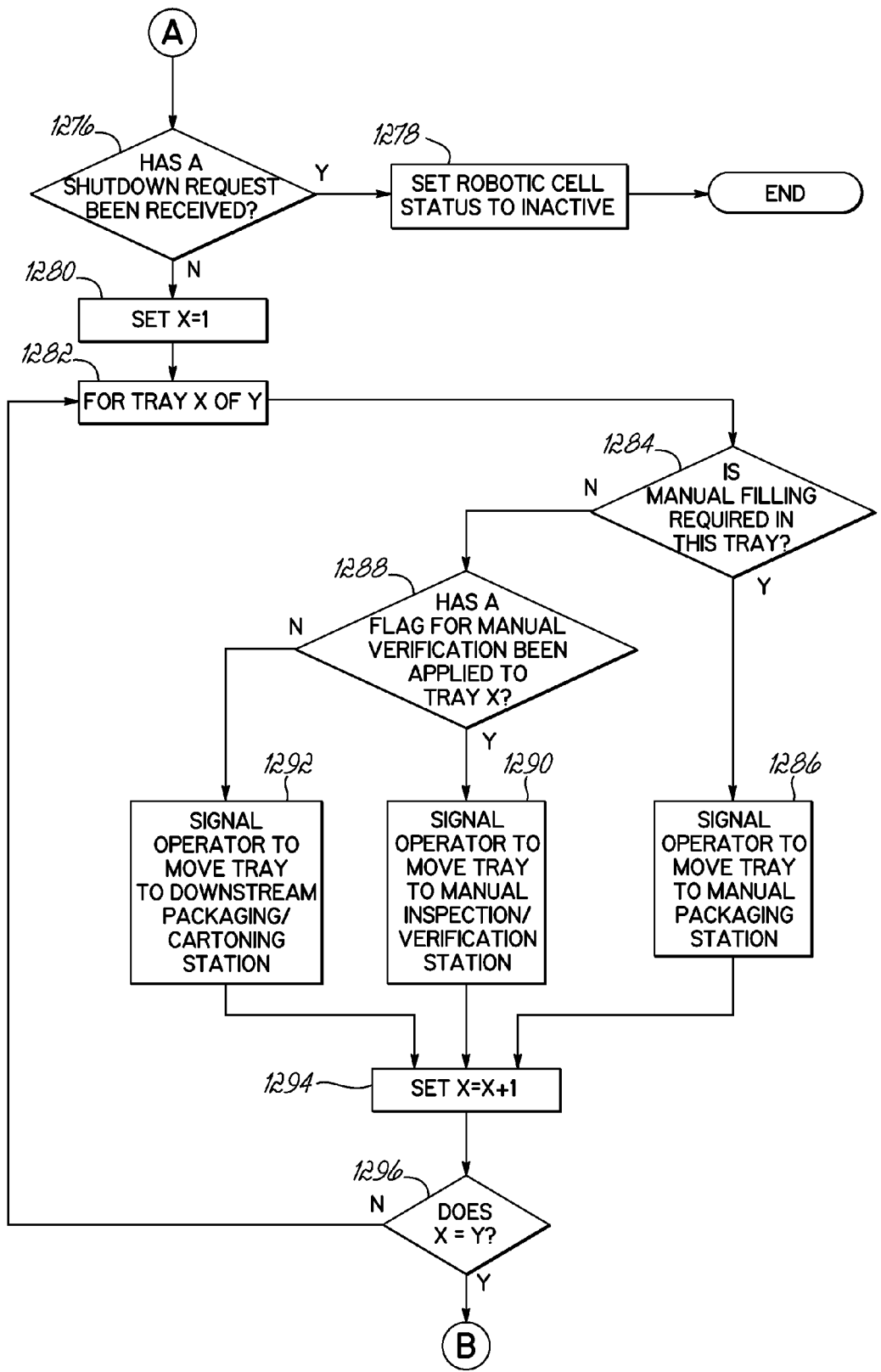
FIG. 35B is the continuation of the flowchart of sequences of operations shown in FIG. 35A.

FIGS. 35A and 35B depict flowchart 1248, which is a series of operations used in an order tray monitoring cycle configured to track all of the trays 186 of a particular patient order being filled by the drug packaging system 10, and particularly the operations associated with the packaging that occurs at the automated packaging station 16. This process is interrelated with the second robot control cycle previously described. To this end, the monitoring cycle begins with the controller 42 retrieving a new order to be filled into a number of trays 186 designated by the variable Y (block 1250). The controller 42 then sets a variable X equal to 1 (block 1252).

For tray X of the Y total trays (block 1254), the controller 42 signals the operators 156 to insert an empty tray 186 into the drawer 184 at the blister unloading station 182 (block 1256). After this insertion of a new tray 186, the barcode on the tray 186 is scanned (block 1258). The controller 42 then determines if the tray barcode was readable (block 1260). If the barcode was not readable, then the controller 42 generates an alarm for the inability to read the tray barcode (block 1262) and returns to signal the operator 156 once more to insert an empty tray 186 into the drawer 184 at block 1256. If the tray barcode was successfully read, then the controller 42 determines if the tray 186 has been previously assigned to another active order (block 1264). If such a previous assignment is detected, then the controller 42 generates an alarm and/or a signal to the operators 156 regarding the previous assignment of the tray 186 (block 1266) and then returns to block 1256 to signal the operator 156 to enter another empty tray 186 into the drawer 184. If the tray 186 had not been assigned to another active order, the controller 42 waits for the tray 186 to be filled (block 1268). Once this tray 186 is filled, the controller 42 determines if the variables X and Y equal each other, which would indicate that the last tray 186 had been filled for the order (block 1270). If X is not equal to Y, then X is incremented by 1 (block 1272) and the controller 42 returns to block 1254 to begin the process for the new tray X of Y.

On the other hand, if X=Y, then the controller 42 generates a signal indicating that automated filling is completed for this order (block 1274). The controller 42 then checks to see if a shutdown request has been received (block 1276). If such a shutdown request has been received, then the controller 42 sets the robotic cell status to inactive (block 1278) and the monitoring cycle ends. If no shutdown request has been received, then the controller 42 resets the variable X to 1 (block 1280). For tray X of Y total trays 186 (block 1282), the controller 42 proceeds to determine if manual filling is required in the tray (block 1284). If manual filling of certain medications is required in a given tray 186, then the controller 42 signals the operator 156 to move the tray 186 to the manual packaging station 14 (block 1286). If no manual filling is required for this particular tray, the controller 42 checks to see if any flags for manual verification have been applied to tray X (block 1288). If such flag(s) have been applied, then the controller 42 signals the operator 156 to move the tray 186 to a manual inspection and verification station (block 1290). If no such flags for manual verification were applied to the tray 186, then the controller 42 signals the operator 156 to move the tray 186 to downstream packaging and cartoning stations (block 1292). Regardless of which signal is provided to instruct the operator 156 where to forward the tray 186 to (blocks 1286, 1290, and 1292), the controller 42 increments X by 1 (block 1294) and determines if X=Y, which would indicate the end of the trays 186 for that order (block 1296). If X is not equal to Y, then the controller 42 returns to block 1282 to evaluate the next tray X of Y. If X=Y, then this order is completed and the controller 42 returns to block 1250 to retrieve a new order as described in detail above.

Figure 36:
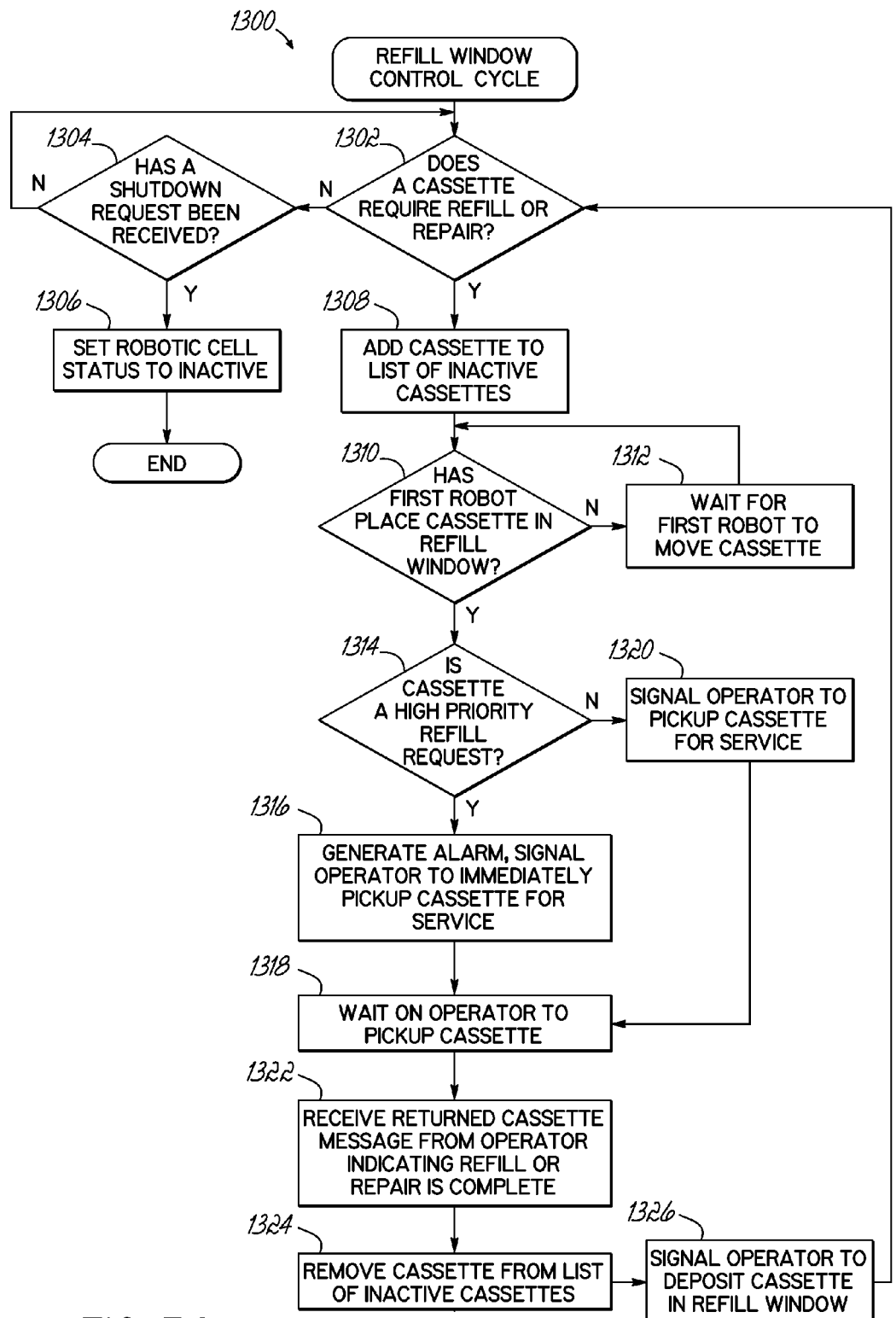
FIG. 36 is a flowchart of sequences of operations that may be performed during a refill window control cycle used with the automated packaging station of FIG. 4.

With reference to FIG. 36, flowchart 1300 provides a series of operations used during a refill window control cycle. This control cycle is related to the first robot control cycle described above, especially with regards to the servicing of the refill window 176 by the first robot 44 described in flowchart 1012. The refill window control cycle begins with the controller 42 determining whether a cassette 162 requires refill or repair (block 1302). If no cassettes 162 require refill or repair, then the controller 42 checks to see if a shutdown request has been received (block 1304). If such a shutdown request has been received, the controller 42 sets the robotic cell status to inactive (block 1306) and the control cycle ends. If no shutdown request has been received, then the controller 42 returns to block 1302 to check again if a cassette 162 requires refill or repair.

If it is determined that a cassette 162 does require repair or refilling, then this cassette 162 is added to the list of inactive cassettes by the controller 42 (block 1308). The controller 42 then checks to see if the first robot 44 has placed the cassette 162 into the refill window 176 (block 1310). If the cassette 162 has not yet been placed in the refill window 176, the controller 42 waits for the first robot 44 to move the cassette 162 (block 1312). Once the first robot 44 has placed the cassette 162 on the refill window 176, the controller 42 determines if the cassette 162 is subject to a high priority refill request (block 1314). If the cassette 162 is subject to a high priority request, such as when the current filling order is waiting on the refill, the controller 42 generates an alarm and/or signals an operator 156 to immediately pick up the cassette 162 for service (block 1316). The controller 42 then waits for the operator 156 to pick up the cassette 162 (block 1318). If the cassette 162 was not subject to a high priority request at block 1314, then the controller 42 signals the operator 156 to pick up the cassette 162 for service when possible (block 1320). Once again, the controller 42 waits after this signaling at block 1318 for the operator 156 to pick up the cassette 162.

After the cassette 162 has been picked up, the controller 42 receives a returned cassette message from the operator 156 indicating that the refill or repair of the cassette 162 is completed (block 1322). The cassette 162 is then removed from the list of inactive cassettes 162 by the controller 42 (block 1324). Additionally, the controller 42 signals the operator 156 to deposit the cassette 162 in the refill window 176 if not done already (block 1326). The control cycle then returns to block 1302 to determine once more if a cassette 162 needs refill or repair. Simultaneously, the first robot 44 is signaled to retrieve the returned cassette as previously described.

In summary, the previously described multiple series of operations in the flowcharts enable the simultaneous control of the various elements of the automated packaging station 16. Therefore, the orders may be continuously filled one after another as long as the automated packaging station 16 has orders to fill and adequate inventory of bulk supply medications to fill the blister packs 90 needed. Furthermore, any potential problems with the automated filling are detected and flagged for manual (human) verification and correction, if required. The drug packaging system 10 therefore improves the efficiency and accuracy of the medication filling process, especially with regard to providing patients with customized packages containing multiple medications for each medicine pass in a day as well as for PRN ("take as needed") medication purposes.

It will be understood that the various steps of the prescription organization and filling processes described above may be reordered or reconfigured as required in other embodiments of a filling process and apparatus. The particular layout of the automated packaging station 16 may further be modified as desired, such as for more efficient movement of cassettes 162. The processes described herein are also not limited to the flowchart representations, but those flowcharts are an exemplary embodiment.

References herein to directional terms such as "vertical", "horizontal", "upper", "lower", "raise", "lower", etc. are made by way of example, and not by way of limitation, to establish a frame of reference. It is understood by persons of ordinary skill in the art that various other frames of reference may be equivalently employed for purposes of describing the embodiments of the invention.

It will be understood that when an element is described as being "attached", "connected", or "coupled" to or with another element, the element can be directly connected or coupled to the other element or, instead, one or more intervening elements may be present. In contrast, when an element is described as being "directly attached", "directly connected", or "directly coupled" to another element, there are no intervening elements present. When an element is described as being "indirectly attached", "indirectly connected", or "indirectly coupled" to another element, there is at least one intervening element present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising."

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A method for filling packagings with at least one medication, comprising:
   receiving filling instructions for an order, including an allocation of medications to a plurality of the packagings, each packaging adapted to receive at least one of the medications to be taken by a patient at a specified time or as needed, and each packaging including a body with a plurality of separated compartments for separately holding different medications; and
   operating an automated packaging station to fill the plurality of the packagings for the order, wherein operating the automated packaging station further includes:
      positioning a plurality of cassettes containing the medications needed for the order onto a feeder base at a single filling location, the feeder base including a plurality of chutes extending between the cassettes and the plurality of separated compartments of a packaging located at the filling location;
      moving each of the plurality of packagings to the filling location; and
      actuating at least one of the plurality of cassettes at the feeder base simultaneously and according to the filling instructions when each packaging is located at the filling location, thereby simultaneously depositing each of the medications needed for that packaging into corresponding separated compartments of that packaging, the plurality of chutes in the feeder base directly passing each dispensed unit dose into a corresponding one of the plurality of separated compartments.

2. The method of claim 1, wherein receiving filling instructions for the order further comprises:
   analyzing a plurality of prescriptions for the patient; and
   generating the filling instructions based at least in part on the analyzed prescriptions.

3. The method of claim 2, wherein generating the filling instructions further comprises:
   receiving a dosage schedule for each medication from the plurality of prescriptions;
   allocating each medication from the plurality of prescriptions to the plurality of packagings based on the dosage schedule for each medication;
   identifying any undesirable drug contra-indications between multiple medications allocated to the same packaging; and
   if an undesirable drug contra-indication between multiple medications is present in any of the packagings, modifying the allocation of the conflicting medications to different packagings to avoid the undesirable drug contra-indication.

4. The method of claim 3, wherein generating the filling instructions further comprises:
   receiving administration time preferences for the patient from the patient or from a physician; and
   modifying the allocation of medications to the plurality of packagings based on the administration time preferences.

5. The method of claim 1, wherein receiving filling instructions further comprises:
   retrieving a list of pending orders for a plurality of patients;
   excluding from the list of pending orders any orders that do not require filling at the automated packaging station;
   sorting the list of pending orders to establish a priority for which pending order should be filled first;
   checking whether the automated packaging station has sufficient inventory of the medications needed to fill the pending order that should be filled first; and
   if the automated packaging station has sufficient inventory for the first pending order, assigning that first pending order to be filled at the automated packaging station by providing the filling instructions for the first pending order to a machine controller.

6. A method for filling packagings with at least one medication, comprising:
   receiving filling instructions for an order, including an allocation of medications to a plurality of the packagings, each packaging adapted to receive at least one of the medications to be taken by a patient at a specified time or as needed; and
   operating an automated packaging station to fill the plurality of the packagings for the order, wherein operating the automated packaging station further includes:
      positioning a plurality of cassettes containing the medications needed for the order onto a feeder base at a single filling location;

moving each of the plurality of packagings to the filling location; and actuating at least one of the plurality of cassettes at the feeder base simultaneously and according to the filling instructions when each packaging is located at the filling location, thereby simultaneously depositing each of the medications needed for that packaging into that packaging, and wherein the automated packaging station includes storage carousels containing cassettes with bulk supplies of medications, a turntable assembly including the feeder base at the filling location, and a first robot configured to selectively collect the cassettes, and wherein positioning the plurality of cassettes and moving each of the plurality of packagings further comprises:

moving the plurality of cassettes with the first robot between the storage carousels and the turntable assembly; and moving the turntable assembly with an indexed movement configured to sequentially position each of the plurality of packagings at the filling location.

7. The method of claim 6, wherein each packaging includes a plurality of compartments, the feeder base includes a plurality of chutes extending between the cassettes and the plurality of compartments of a packaging located at the filling location, and actuating at least one of the plurality of cassettes at the feeder base further comprises:

simultaneously actuating a dispense mechanism of each cassette containing a unit dose of medication that is to be received in a compartment of the packaging at the filling location; and directing each dispensed unit dose simultaneously through the plurality of chutes into the plurality of compartments.

8. The method of claim 6, wherein the turntable assembly further includes a loading staging table and an unloading staging table each located adjacent to the feeder base, and moving the plurality of cassettes with the first robot between the storage carousels and the turntable assembly further comprises:

retrieving a first set of cassettes from the storage carousels;
depositing the first set of cassettes onto the loading staging table;
moving a second set of cassettes from the feeder base onto the unloading staging table;
moving the first set of cassettes from the loading staging table onto the feeder base;
retrieving the second set of cassettes from the unloading staging table; and
returning the second set of cassettes to the storage carousels.

9. The method of claim 8, wherein the plurality of packagings is divided into multiple sets of packagings configured to receive different pluralities of medications, and wherein operating the automated packaging station further comprises:

repeating the movement of packagings to the filling location and the actuation of at least one of the plurality of cassettes while the second set of cassettes is located on the feeder base for one of the sets of packagings; and
repeating the movement of packagings to the filling location and the actuation of at least one of the plurality of cassettes while the first set of cassettes is located on the feeder base for another of the sets of packagings.

10. The method of claim 9, wherein the retrieval and deposit or return steps performed by the first robot are performed simultaneous to the actuation of the feeder base to dispense medications into the packagings, such that the next set of cassettes is located on the loading staging table and ready to replace the currently used set of cassettes when the feeder base is finished depositing medications with the currently used set of cassettes.

11. The method of claim 8, wherein the first robot is configured to hold cassettes with a first gripping head operable to hold up to four cassettes and with a second gripping head operable to hold up to eight cassettes, and moving the plurality of cassettes with the first robot between the storage carousels and the turntable assembly further comprises:

using the first gripping head to move the cassettes between the storage carousels and the loading and unloading staging tables; and
using the second gripping head to move the cassettes between the feeder base and the loading and unloading staging tables.

12. The method of claim 11, wherein each of the loading and unloading staging tables includes a plurality of stationary platens to receive cassettes and a plurality of moveable platens to receive cassettes, and moving cassettes to and from the feeder base and the storage carousels with the first robot further comprises:

moving the plurality of moveable platens between raised and lowered positions to selectively provide access to only four cassettes at a time when the first gripping head is used by the first robot; and
keeping the plurality of moveable platens generally coplanar with the plurality of stationary platens to provide access to up to eight cassettes at a time when the second gripping head is used by the first robot.

13. The method of claim 6, wherein the automated packaging station further includes a refill window accessible to the first robot and to human operators, and operating the automated packaging station further comprises:

detecting that at least one cassette requires refill of bulk supply or repair;
moving the at least one cassette requiring refill or repair to the refill window from the storage carousels or from the turntable assembly using the first robot;
signaling the human operator to prompt removal of the at least one cassette from the refill window for refilling or repair.

14. The method of claim 13, wherein when the at least one cassette has been refilled or repaired and positioned back in the refill window, operating the automated packaging station further comprises:

retrieving the at least one cassette with the first robot; and
depositing the at least one cassette back into the storage carousels or onto the turntable assembly.

15. The method of claim 6, wherein the turntable assembly further includes a rotary dial including a plurality of nests each configured to receive one of the plurality of packagings, and operating the automated packaging station further comprises:

rotating each nest underneath at least one packaging magazine configured to position an empty packaging onto the nest;
rotating each nest containing a packaging underneath the feeder base to receive the medications from the cassettes at the feeder base; and
rotating each nest to an unloading station at which a second robot is stationed to remove filled packagings from the nests.

16. The method of claim 15, wherein the plurality of packagings is divided into multiple sets of packagings configured to receive different pluralities of medications, and wherein operating the automated packaging station further comprises:

positioning each empty packaging of a first set of the packagings onto consecutive nests rotating around the rotary dial with the at least one packaging magazine;

leaving one nest empty on the rotary dial before positioning each empty packaging of a second set of the packagings onto consecutive nests rotating around the rotary dial; and rotating the empty nest into the filling location during exchange and positioning of a next plurality of cassettes onto the feeder base such that any medications accidentally dispensed during this positioning are not deposited into a packaging.

17. The method of claim 15, wherein operating the automated packaging station further comprises:

rotating each filled packaging in the nests through a fill verification station configured to verify the deposit of medications by the feeder base; and rotating each filled packaging through a printer assembly configured to apply a sealing cover to the packaging.

18. The method of claim 17, wherein operating the automated packaging station further comprises:

rotating each filled packaging in the nests through a product verification station configured to verify the identity of medications deposited into the packagings using laser spectroscopy.

19. The method of claim 17, wherein operating the automated packaging station further comprises:

rotating each of the plurality of packagings from the filling location to an additional filling location associated with an alternative loading mechanism at the turntable assembly, the alternative loading mechanism operating to deposit non-cassette dispensable medications into packagings requiring such non-cassette dispensable medications.

20. The method of claim 19, wherein operating the automated packaging station further comprises:

rotating each filled packaging in the nests through another fill verification station configured to verify the deposit of medications by the alternative loading mechanism.

21. The method of claim 17, wherein the printer assembly is operable to print patient identification and product identification information in the form of machine readable indicia and human readable labels on the covers, and operating the automated packaging station further comprises:

determining if the deposit of medications into one of the packagings is verified to be correct;

printing patient identification and product identification information on the cover for that packaging if the deposit of medications is verified to be correct; and modifying the printing of patient identification and product identification information on the cover for that packaging to indicate that downstream inspection is required if the deposit of medications is not verified to be correct.

22. The method of claim 15, wherein each of the at least one packaging magazines includes a magazine channel for receiving a stack of empty packagings and a gripping head assembly, and operating the automated packaging station further comprises:

grabbing one empty packaging from the magazine channel with the gripping head assembly;

rotating the gripping head assembly so that the empty packaging faces toward a nest without a packaging; and positioning the empty packaging into the nest with the gripping head assembly.

23. The method of claim 15, wherein the automated packaging station further includes the unloading station, which includes the second robot and at least two drawers configured to receive trays for receiving filled packagings, and operating the automated packaging station further comprises:

moving filled packagings from the rotary dial to the trays with the second robot;

sensing that one of the trays is filled with packagings; and prompting a human operator to open the drawer and replace the filled tray with an empty tray adapted to receive additional packagings from the second robot.

24. An automated packaging station for filling packagings with at least one medication, comprising:

a robotic work zone enclosed by a barrier wall;

a plurality of storage carousels in the robotic work zone, the storage carousels holding cassettes each containing a bulk supply of a medication;

a turntable assembly in the robotic work zone, the turntable assembly including a single filling location and a feeder base configured to receive a plurality of cassettes from the storage carousels, the feeder base also configured to actuate simultaneous dispensing of medications from at least one of the plurality of cassettes into each of the packagings when located at the filling location;

a first robot in the robotic work zone and configured to selectively move cassettes between the storage carousels and the turntable assembly;

a machine controller having a processor and a memory; and program code resident in the memory and configured to be executed by the processor to receive filling instructions for an order and to operate the elements in the robotic work zone according to the filling instructions to fill the packagings with the at least one medication.

25. The automated packaging station of claim 24, further comprising:

program code resident in the memory and configured to be executed by the processor to retrieve a list of pending orders for a plurality of patients, exclude any orders that do not require automated filling of medications, prioritize the list of non-excluded orders, check whether the robotic work zone has enough inventory to fill the most highly prioritized order in the list, and assign the order to be filled in the robotic work zone if the robotic work zone has sufficient inventory to fill the order.

26. The automated packaging station of claim 24, wherein each packaging includes a plurality of compartments, the feeder base includes a plurality of chutes extending between the compartments of the packaging at the filling location and the plurality of cassettes, and the feeder base includes a plurality of actuator petals configured to simultaneously actuate the dispensing of unit doses from any selected combination of the plurality of cassettes through the corresponding plurality of chutes and into the plurality of compartments.

27. The automated packaging station of claim 26, wherein each of the plurality of actuator petals further includes a memory chip interface configured to receive cassette identification information from a memory chip on each cassette, thereby verifying the correct placement of the plurality of cassettes on the plurality of actuator petals.

28. The automated packaging station of claim 24, further comprising:

a loading staging table located on the turntable assembly adjacent to the feeder base; and an unloading staging table located on the turntable assembly adjacent to the feeder base, wherein each of the loading and unloading staging tables includes a plurality of platens configured to receive the plurality of cassettes either before or after placement on the feeder base.

29. The automated packaging station of claim 28, wherein the plurality of platens on each of the loading and unloading staging tables further includes a plurality of stationary platens and a plurality of moveable platens configured to move with respect to the stationary platens between a generally coplanar relationship with the stationary platens to a raised position above the stationary platens.

30. The automated packaging station of claim 29, wherein the first robot further includes a first gripping head configured to hold up to four cassettes for movement between the storage carousels and the staging tables, the first robot includes a second gripping head configured to hold up to eight cassettes for movement between the staging tables and the feeder base, and the moveable platens are configured to move to the raised position only when the first robot is using the first gripping head.

31. The automated packaging station of claim 24, further comprising:
a refill window communicating between the robotic work zone and an operator work zone located outside the barrier wall, wherein the first robot is configured to move cassettes requiring refill of bulk stock or repair between the refill window and the robotic work zone so that an operator can work on the cassettes in the operator work zone.

32. The automated packaging station of claim 24, wherein the turntable assembly further includes a rotary dial with a plurality of nests each configured to receive one of the packagings, the rotary dial coupled to a motor configured to apply an indexed rotation of the nests to and from the filling location.

33. The automated packaging station of claim 32, further comprising:
at least one packaging magazine located at the turntable assembly and including a magazine channel configured to receive a stack of empty packagings and a gripping head assembly configured to selectively move one of the empty packagings from the magazine channel to one of the plurality of nests on the rotary dial.

34. The automated packaging station of claim 33, wherein the at least one packaging magazine includes at least one of an angled projection and an alignment pin configured to force each empty packagaing in the magazine channel to have a known orientation, and each nest on the rotary dial includes an indexing feature configured to confirm the known orientation of the empty packaging when positioned on the rotary dial.

35. The automated packaging station of claim 32, further comprising:
an alternative loading mechanism located at the turntable assembly and configured to deposit non-cassette dispensable medications into packagings located at an additional filling location along the rotary dial; and
at least one fill verification station located above the rotary dial and configured to verify the deposit of medications by the feeder base or the alternative loading mechanism.

36. The automated packaging station of claim 32, further comprising:
a product verification station located above the rotary dial and configured to verify the identity of medications deposited into the packagings using laser spectroscopy.

37. The automated packaging station of claim 32, further comprising:
a printer assembly located above the rotary dial at the turntable assembly, the printer assembly configured to print information on a sealing cover and apply that sealing cover to a filled packaging at the printer assembly.

38. The automated packaging station of claim 37, further comprising:
an unloading station located at the rotary dial of the turntable assembly downstream in the direction of rotation from the printer assembly, the unloading station including at least two drawers configured to receive trays for holding filled packagings and a second robot operable to move filled packagings from the rotary dial to the trays in the drawers.

39. The automated packaging station of claim 24, further comprising:
an operator work zone located outside the barrier wall; and
a user interface in the operator work zone and configured to enable interaction between operators in the operator work zone and the elements within the robotic work zone via commands to the machine controller.

* * * * *